US 11,422,072 B2

(12) United States Patent
Kubota et al.

(10) Patent No.: US 11,422,072 B2
(45) Date of Patent: Aug. 23, 2022

(54) SPECIMEN SMEARING APPARATUS, SPECIMEN SMEARING METHOD, SMEAR SAMPLE PREPARING APPARATUS, AND SMEAR SAMPLE PREPARING METHOD

(71) Applicant: SYSMEX CORPORATION, Kobe (JP)

(72) Inventors: Shogo Kubota, Kobe (JP); Seiya Shinabe, Kobe (JP); Hiroyuki Koga, Kobe (JP); Noriyuki Nakanishi, Kobe (JP); Yuichiro Ohmae, Kobe (JP); Toshihisa Tanaka, Kobe (JP); Tetsuya Oda, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 190 days.

(21) Appl. No.: 16/934,918

(22) Filed: Jul. 21, 2020

(65) Prior Publication Data

US 2020/0348214 A1   Nov. 5, 2020

Related U.S. Application Data

(63) Continuation of application No. 15/906,456, filed on Feb. 27, 2018, now Pat. No. 10,801,929, which is a
(Continued)

(30) Foreign Application Priority Data

Aug. 31, 2015 (JP) .............................. JP2015-171204
Apr. 28, 2016 (JP) .............................. JP2016-092071

(51) Int. Cl.
*G01N 1/00* (2006.01)
*G01N 1/28* (2006.01)
(Continued)

(52) U.S. Cl.
CPC ............. *G01N 1/2813* (2013.01); *G01N 1/28* (2013.01); *G01N 1/30* (2013.01); *G01N 1/312* (2013.01);
(Continued)

(58) Field of Classification Search
None
See application file for complete search history.

(56) References Cited

U.S. PATENT DOCUMENTS 4,319,542 A    3/1982   Ojima et al.
5,270,012 A   12/1993   Kanamori et al.
(Continued)

FOREIGN PATENT DOCUMENTS

CN   101464237 A    6/2009
CN   101900720 A   12/2010
(Continued)

OTHER PUBLICATIONS

The Chinese Rejection Decision dated Oct. 9, 2021 in a corresponding Chinese patent application No. 201680050083.2.
(Continued)

*Primary Examiner* — Jyoti Nagpaul
(74) *Attorney, Agent, or Firm* — Crowell & Moring LLP

(57) ABSTRACT

Disclosed is a specimen smearing apparatus including: a slide supplying section configured to supply a glass slide yet to be processed; a first processing section configured to perform a first process on the glass slide, the first processing section being disposed in a first direction with respect to the slide supplying section, the first direction being a far direction of an apparatus body of the specimen smearing apparatus; a second processing section configured to perform on the glass slide a second process which is different from the first process, the second processing section being disposed in a second direction with respect to the first processing
(Continued)

section, the second direction being a left-right direction of the apparatus body and orthogonal to the first direction; and a first drying processing section disposed in a third direction with respect to the second processing section, the third direction being a near direction of the apparatus body and opposite to the first direction, the first drying processing section configured to dry a specimen on the glass slide on which the first process and the second process have been performed, wherein one of the first processing section and the second processing section is configured to perform a smearing process for smearing a specimen on the glass slide.

20 Claims, 35 Drawing Sheets

Related U.S. Application Data continuation of application No. PCT/JP2016/072052, filed on Jul. 27, 2016.

(51) Int. Cl.
  G01N 1/30 (2006.01)
  G01N 35/04 (2006.01)
  G01N 33/48 (2006.01)
  G01N 35/00 (2006.01)
  G01N 1/31 (2006.01)

(52) U.S. Cl.
  CPC ....... *G01N 33/48* (2013.01); *G01N 35/00029* (2013.01); *G01N 35/0099* (2013.01); *G01N 35/04* (2013.01); *G01N 2035/00039* (2013.01); *G01N 2035/00138* (2013.01)

(56) References Cited

U.S. PATENT DOCUMENTS

| 5,356,595 | A  | 10/1994 | Kanamori et al. |
| 6,319,470 | B1 | 11/2001 | Lefevre et al.  |
| 2006/0029519 | A1 | 2/2006 | Nakaya et al. |
| 2006/0051241 | A1 | 3/2006 | Higuchi et al. |
| 2012/0201721 | A1 | 8/2012 | Yamasaki |
| 2014/0295562 | A1 | 10/2014 | Wakamiya et al. |
| 2015/0093754 | A1 | 4/2015 | Asao et al. |

FOREIGN PATENT DOCUMENTS

| CN | 104515865 | 4/2015 |
| EP | 0 417 006 | 3/1991 |
| EP | 2 853 900 | 4/2015 |
| JP | S56-011337 A | 2/1981 |
| JP | 02-140447 U | 11/1990 |
| JP | 04-021951 U | 2/1992 |
| JP | H08-271390 A | 10/1996 |
| JP | H08-316289 A | 11/1996 |
| JP | 2000-74803 A | 3/2000 |
| JP | 2003-302408 A | 10/2003 |
| JP | 2005-181245 A | 7/2005 |
| JP | 2006-78296 A | 3/2006 |
| JP | 2009-145261 A | 7/2009 |
| JP | 2012-159480 A | 8/2012 |
| JP | 2014-194390 A | 10/2014 |
| JP | 2014-239038 | 11/2014 |
| JP | 2015-068669 A | 4/2015 |
| JP | 2016-099324 A | 5/2016 |
| WO | WO2015/165019 | 11/2015 |
| WO | WO 2017/038323 A1 | 3/2017 |

OTHER PUBLICATIONS

The Chinese Office Action dated Apr. 26, 2021 in a counterpart Chinese patent application No. 201680050083.2.
The Communication pursuant to Article 94(3) EPC dated Aug. 12, 2020 in a counterpart European patent application No. 16841355.7.
The Chinese Office Action dated Apr. 7, 2020 in a counterpart Chinese patent application No. 201680050083.2.
The extended European search report dated Mar. 19, 2019 in a counterpart European patent application No. 16841355.7.
International Search Report, dated Oct. 18, 2016, in International Application No. PCT/JP2016/072052.
Extended European search report dated May 3, 2022 in a counterpart European patent application No. 22154972.8.

FIG. 27

| SPECIMEN ID | | | | | |
|---|---|---|---|---|---|
| | | ☐ READ BAR CODE | | | |

SPECIMEN CONTAINER

| NORMAL ▽ | ☑ OPEN MEASUREMENT | NUMBER OF SHEETS | CASSETTE | |
|---|---|---|---|---|
| SMEARING CONDITION | | 1 | NOT DESIGNATED | CHANGE |
| 5.35 ≤ HCT(%) < 40  ▽ | | 2 | CASSETTE 1 | |

OK  CANCEL

930

SPECIMEN SMEARING APPARATUS, SPECIMEN SMEARING METHOD, SMEAR SAMPLE PREPARING APPARATUS, AND SMEAR SAMPLE PREPARING METHOD

CROSS REFERENCE TO RELATED APPLICATIONS

This application is a continuation of U.S. patent application Ser. No. 15/906,456 filed on Feb. 27, 2018, which is a continuation of International Application PCT/JP2016/072052 filed on Jul. 27, 2016, which claims benefit of Japanese patent applications JP 2015-171204 filed on Aug. 31, 2015 and JP 2016-092071 filed on Apr. 28, 2016, all of which are incorporated herein by reference in their entireties.

FIELD OF THE INVENTION

The present invention relates to a specimen smearing apparatus, a specimen smearing method, a smear sample preparing apparatus, and a smear sample preparing method.

BACKGROUND

A specimen smearing apparatus is an apparatus that applies, on a glass slide, a specimen to be subjected to microscopy. The specimen smearing apparatus includes many processing sections in order to perform a printing process, a smearing process, a drying process, and the like, on a glass slide. In the specimen smearing apparatus, transportation of glass slides among processing sections is complicated, and thus, the size of the specimen smearing apparatus tends to be increased.

For example, Japanese Laid-Open Patent Publication No. 2009-145261 discloses a specimen smearing apparatus which includes: a slide supplying section configured to supply a glass slide; a first transportation section and a second transportation section each configured to transport the glass slide; a smearing section configured to smear a specimen on the glass slide; a specimen drying section configured to dry the specimen smeared on the glass slide; and a printing part configured to perform printing on the glass slide. When two horizontal directions orthogonal to each other are defined as an X direction and a Y direction, the first transportation section transports in the Y direction the glass slide supplied from the slide supplying section, to deliver the glass slide to the second transportation section. The second transportation section transports the received glass slide to a smearing section at one side in the X direction, and then, transports in an opposite direction the glass slide having been subjected to a smearing process, thereby to transport the glass slide to a specimen drying section at the other side in the X direction. The second transportation section further transports the glass slide having been subjected to a specimen drying process, to the printing part at the other side in the X direction.

In Japanese Laid-Open Patent Publication No. 2009-145261, a T-shaped transport route is formed by the first transportation section and the second transportation section, and a glass slide is transported in the Y direction from the slide supplying section, and then is transported so as to reciprocate in the X direction.

Thus, in such a conventional specimen smearing apparatus as in Japanese Laid-Open Patent Publication No. 2009-145261 described above, since many processing sections are provided, the transport route for the glass slide is complicated due to reciprocation of the glass slide in the same route, which results in a large apparatus. Thus, in order to reduce the installation space in a hospital, a test institution, or the like, it is desired to simplify the transport route for the glass slide, to downsize the specimen smearing apparatus.

In addition, with respect to a specimen smearing apparatus, for example, various types of work are performed by a user, such as: setting a glass slide yet to be processed, to the specimen smearing apparatus; taking-out a glass slide for which a smearing process has been completed; setting a glass slide on which the user performed smearing; and taking-out a glass slide for which staining has been completed. A specimen smearing apparatus that enables the user to easily perform such various types of work is desired.

SUMMARY OF THE INVENTION

The scope of the present invention is defined solely by the appended claims, and is not affected to any degree by the statements within this summary.

A specimen smearing apparatus according to a first aspect of the present invention includes: a slide supplying section configured to supply a glass slide yet to be processed; a first processing section configured to perform a first process on the glass slide, the first processing section being disposed in a first direction with respect to the slide supplying section, the first direction being a far direction of an apparatus body of the specimen smearing apparatus; a second processing section configured to perform on the glass slide a second process which is different from the first process, the second processing section being disposed in a second direction with respect to the first processing section, the second direction being a left-right direction of the apparatus body and orthogonal to the first direction; and a first drying processing section disposed in a third direction with respect to the second processing section, the third direction being a near direction of the apparatus body and opposite to the first direction, the first drying processing section configured to dry a specimen on the glass slide on which the first process and the second process have been performed, wherein one of the first processing section and the second processing section is configured to perform a smearing process for smearing a specimen on the glass slide.

A specimen smearing method according to a second aspect of the present invention is a specimen smearing method for smearing a specimen on a glass slide, the method including: transporting in a first direction a glass slide yet to be processed, from a supply position at which to supply the glass slide, and performing a first process on the glass slide; transporting the glass slide on which the first process has been performed, in a second direction orthogonal to the first direction, from a processing position for the first process, and performing on the glass slide a second process which is different from the first process; and transporting the glass slide on which the second process has been performed, in a third direction opposite to the first direction, from a processing position for the second process, and performing a drying process for drying the specimen on the glass slide on which the first process and the second process have been performed, wherein one of the first process and the second process is a smearing process for smearing the specimen on the glass slide.

A smear sample preparing apparatus according to a third aspect of the present invention includes: a slide supplying section configured to supply a glass slide; a smearing processing section configured to perform a smearing process of a specimen on the glass slide supplied by the slide supplying section; a staining processing section configured to perform a staining process on the glass slide on which the smearing process has been performed by the smearing processing section; a slide setting section capable of having set therein a first storage container configured to store a glass slide; and a first transportation section configured to transport a glass slide from a taking-out position on a transport route extending from the smearing processing section to the staining processing section, to the first storage container set in the slide setting section.

A smear sample preparing method according to a fourth aspect of the present invention is a smear sample preparing method of performing: a smear-stain mode in which a smearing process of a specimen is performed on a glass slide, the glass slide on which the smearing process has been performed is transported to a staining processing section, a staining process is performed on the glass slide, and the glass slide on which the staining process has been performed is transported to a storage container; and a smear mode in which a smearing process of a specimen is performed on a glass slide, the glass slide on which the smearing process has been performed is transported to a storage container without being transported to the staining processing section.

BRIEF DESCRIPTION OF THE DRAWINGS

FIG. 27 is a diagram showing an operation condition input screen in the smear-stain mode;

DETAILED DESCRIPTION OF THE PREFERRED EMBODIMENTS

Hereinafter, embodiments are described with reference to the drawings.

First Embodiment (Overview of Specimen Smearing Apparatus)

An overview of a specimen smearing apparatus 100 according to a first embodiment is described with reference to FIG. 1.

The specimen smearing apparatus 100 is an apparatus for smearing a specimen on a glass slide 10. The specimen is a biological specimen taken from a test specimen (subject), and is blood, urine, or cells, for example.

Figure 1:
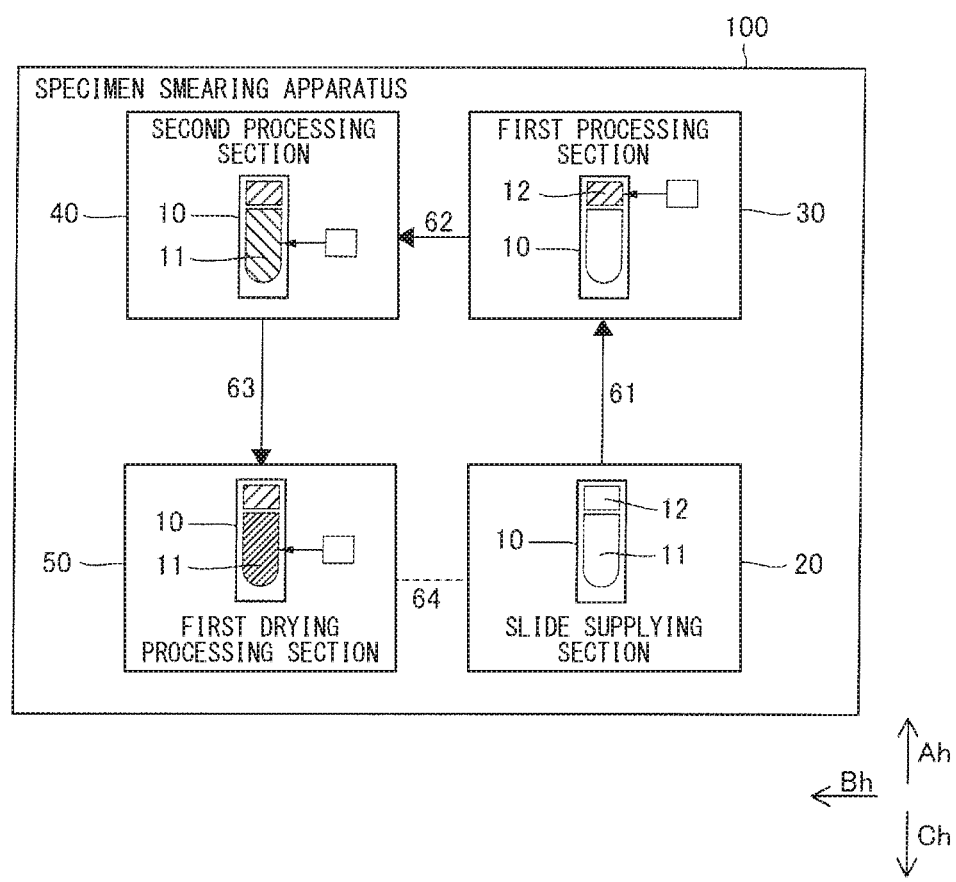
FIG. 1 is a schematic diagram showing the overview of a specimen smearing apparatus according to one embodiment.

As shown in FIG. 1, the specimen smearing apparatus 100 includes a slide supplying section 20, a first processing section 30, a second processing section 40, and a first drying processing section 50.

The glass slide 10 is a plate-like member having a rectangular shape, for example. The glass slide 10 includes: for example, a smear region 11 in which a specimen is smeared; and a printing region 12 for indicating various types of information such as specimen information. The smear region 11 is formed in a center portion in the longitudinal direction, in a predetermined range extending in the longitudinal direction, for example. The printing region 12 is formed in a one-end portion in the longitudinal direction so as to be separated from the smear region 11, for example. The printing region 12 is a portion treated so as to be printable as a result of the glass slide 10 being coated by use of a resin material, for example. In the printing region 12, a specimen number, a date, a bar code, a two-dimensional code, or the like can be printed.

The slide supplying section 20 has a function of supplying a glass slide 10 yet to be processed. The slide supplying section 20 can store a plurality of the glass slides 10. In the specimen smearing apparatus 100, each glass slide 10 supplied from the slide supplying section 20 is transported to the first processing section 30, the second processing section 40, and the first drying processing section 50 in this order. The glass slide 10 is subjected to respective processes performed by the first processing section 30, the second processing section 40, and the first drying processing section 50 in this order.

The first processing section 30 is configured to perform a first process on the glass slide 10. The second processing section 40 is configured to perform a second process which is different from the first process, on the glass slide 10. One of the first processing section 30 and the second processing section 40 is configured to perform a smearing process for smearing a specimen on the glass slide. That is, one of the first process and the second process is the smearing process. The process performed by the other of the first processing section 30 and the second processing section 40 is not limited in particular. The other of the first process and the second process is the printing process for performing printing on the glass slide 10, for example. FIG. 1 shows one example in which one of the first processing section 30 and the second processing section 40 performs the smearing process, and the other of the first processing section 30 and the second processing section 40 performs the printing process. The printing process is a process of printing various types of information such as specimen information, in the printing region 12 on the surface of the glass slide 10. The printing process onto the printing region 12 can be performed by a known printing part such as a thermal transfer printer or an ink jet printer, for example. The smearing process is a process of applying a specimen in the smear region 11 on the surface of the glass slide 10. The specimen is smeared in an amount and an application thickness that are appropriate for microscopy using the glass slide 10. For the smearing process, a smearing method (so-called wedge method) using a smearing member such as a spreader glass, or another smearing method can be employed.

Although FIG. 1 shows one example in which the printing process is performed by the first processing section 30, the first processing section 30 may perform the smearing process. The first processing section 30 is disposed in a first direction with respect to the slide supplying section 20. The first direction is the far direction of the apparatus body. Herein, that the first processing section 30 is disposed in the first direction with respect to the slide supplying section 20 means that the first processing section 30 and the slide supplying section 20 overlap each other in a projection view in the first direction. In other words, viewed from the first direction, the first processing section 30 and the slide supplying section 20 are disposed at positions where the first processing section 30 and the slide supplying section 20 overlap each other. The glass slide 10 supplied from the slide supplying section 20 is transported in the first direction toward the far side of the apparatus body, to be located at a processing position of the first processing section 30. In FIG. 1, the first direction is indicated as an Ah direction.

Although FIG. 1 shows one example in which the smearing process is performed by the second processing section 40, the second processing section 40 may perform the printing process. The second processing section 40 is disposed in a second direction orthogonal to the first direction, with respect to the first processing section 30. The second direction is the left-right direction of the apparatus body. Herein, that the second processing section 40 is disposed in the second direction with respect to the first processing section 30 means that the second processing section 40 and the first processing section 30 overlap each other in a projection view in the second direction. The glass slide 10 having been processed by the first processing section 30 is transported in the second direction extending toward one side in the left-right direction of the apparatus body, to be located at a processing position of the second processing section 40. In FIG. 1, the second direction is indicated as a Bh direction.

The first drying processing section 50 is configured to dry the specimen on the glass slide 10 on which the first process and the second process have been performed. The drying process is a process of forcedly blowing air to the smear region 11 on the surface of the glass slide 10, for example. In this case, the first drying processing section 50 includes a fan, a blower, or the like. The first drying processing section 50 is disposed in a third direction opposite to the first direction, with respect to the second processing section 40. The third direction is a near direction of the apparatus body. Herein, that the first drying processing section 50 is disposed in the third direction with respect to the second processing section 40 means that the first drying processing section 50 and the second processing section 40 overlap each other in a projection view in the third direction. The glass slide 10 having been processed by the second processing section 40 is transported in the third direction extending toward the near side of the apparatus body, to be located at a processing position of the first drying processing section 50. In FIG. 1, the third direction is indicated as a Ch direction.

The first direction, the second direction, and the third direction are directions in a plane that is substantially parallel to the installation surface on which the specimen smearing apparatus 100 is installed. The installation surface can be considered as a substantially horizontal surface, and thus, in short, the first to third directions are directions in a horizontal plane.

With this configuration, the glass slide 10 supplied from the slide supplying section 20 is sequentially transported to the first direction, the second direction, and the third direction, and is subjected to the respective processes. The transport route for the glass slide 10 includes a route 61 in the first direction, a route 62 in the second direction, and a route 63 in the third direction. Roughly speaking, the slide supplying section 20, the first processing section 30, the second processing section 40, and the first drying processing section 50 are disposed at corner portions of a quadrangle region formed by the route 61, the route 62, the route 63, and an imaginary line 64 which connects the slide supplying section 20 and the first drying processing section 50. The transport routes 61 to 63 for the glass slide 10 correspond to a route extending along three sides of the quadrangle region. The length of each of the route 61, the route 62, and the route 63 is set in accordance with the apparatus configuration. In FIG. 1, the route 61 and the route 63 are indicated as having the same length. However, the route 61 and the route 63 may have different lengths. Each of the route 61, the route 62, and the route 63 is not necessarily a straight-line route, and may be a curved route or a branched route. Even in such a case, since the positional relationship of the processing sections is already determined, the transport route for the glass slide 10 is, roughly speaking, a route extending along the route 61, the route 62, and the route 63.

Thus, in the specimen smearing apparatus 100, the glass slide 10 can be sequentially transported in the first direction Ah, the second direction Bh, and the third direction Ch in the order of the slide supplying section 20, the first processing section 30, the second processing section 40, and the first drying processing section 50. That is, a configuration can be realized in which the slide supplying section 20, the first processing section 30, the second processing section 40, and the first drying processing section 50 are disposed, in a plan view, at corner portions of a quadrangle region formed by the route 61, the route 62, the route 63, and the imaginary line 64, such that the glass slide 10 is sequentially transported in a reversed U-shape, along the sides of the quadrangle region. Accordingly, different from a configuration in which many processing sections are arranged on a straight-line route and the glass slide 10 is caused to reciprocate, the glass slide 10 only have to be transported in the reversed U-shape along the forward direction without being returned in the reverse direction, and thus, the transport route can be simplified. In addition, since the slide supplying section 20 and the processing sections (30, 40, and 50) are disposed at the respective corner portions of the quadrangle region, the installation space can be efficiently used. As a result, the transport route for the glass slide 10 can be simplified by arranging the slide supplying section 20 and the processing sections (30, 40, and 50) in a compact manner, whereby the specimen smearing apparatus 100 can be downsized.

The user performs work of setting unprocessed glass slides 10 to the slide supplying section 20, for example. For example, the user performs work of taking-out, from the first drying processing section 50, a glass slide 10 for which the smearing process, the printing process, and the drying process have been ended. Since the slide supplying section 20 and the first drying processing section 50 for which the user performs work are provided at the same near side in the specimen smearing apparatus 100, the work region at the user side in the specimen smearing apparatus 100 can be intensively located at the near side of the apparatus body. As a result, the user can more easily perform his/her work.

Further, the first processing section 30 and the second processing section 40 are each provided with movement mechanisms for the printing part including a print head, a dropping part for dropping a specimen, and a smearing member such as a spreader glass, for example, and thus, tend to have a greater height dimension in the specimen smearing apparatus 100 than other processing sections. Therefore, for example, in a case where the first processing section 30 and the second processing section 40 are arranged alongside each other in the first direction Ah, the processing section at the near side is in the way when the user performs work, and the easiness of access to the processing section at the far side is decreased. In contrast to this, according to the configuration in which the first processing section 30 and the second processing section 40 are arranged alongside each other in the second direction Bh which is the left-right direction as described above, the user can easily perform work on the first processing section 30 and the second processing section 40, such as replacement of a print ribbon, replacement of a spreader glass, and the like.

As a result, according to the configuration described above, the specimen smearing apparatus 100 can be downsized by simplifying the transport route for the glass slide 10, and the user can more easily perform his/her work. That is, the specimen smearing apparatus 100 being compact in size and having high usability can be provided.

(Configuration Example of Smear Sample Preparing Apparatus)

Hereinafter, with reference to FIG. 2 and the figures thereafter, a configuration example is described in which the specimen smearing apparatus 100 shown in FIG. 1 is applied to a specimen smearing section of a smear sample preparing apparatus 300. The smear sample preparing apparatus 300 is an apparatus for performing a smearing process of smearing a specimen on a glass slide 10 and for performing a specimen staining process on the glass slide 10 having the specimen smeared thereon. The specimen is blood, for example.

<Overall Configuration>

Figure 2:
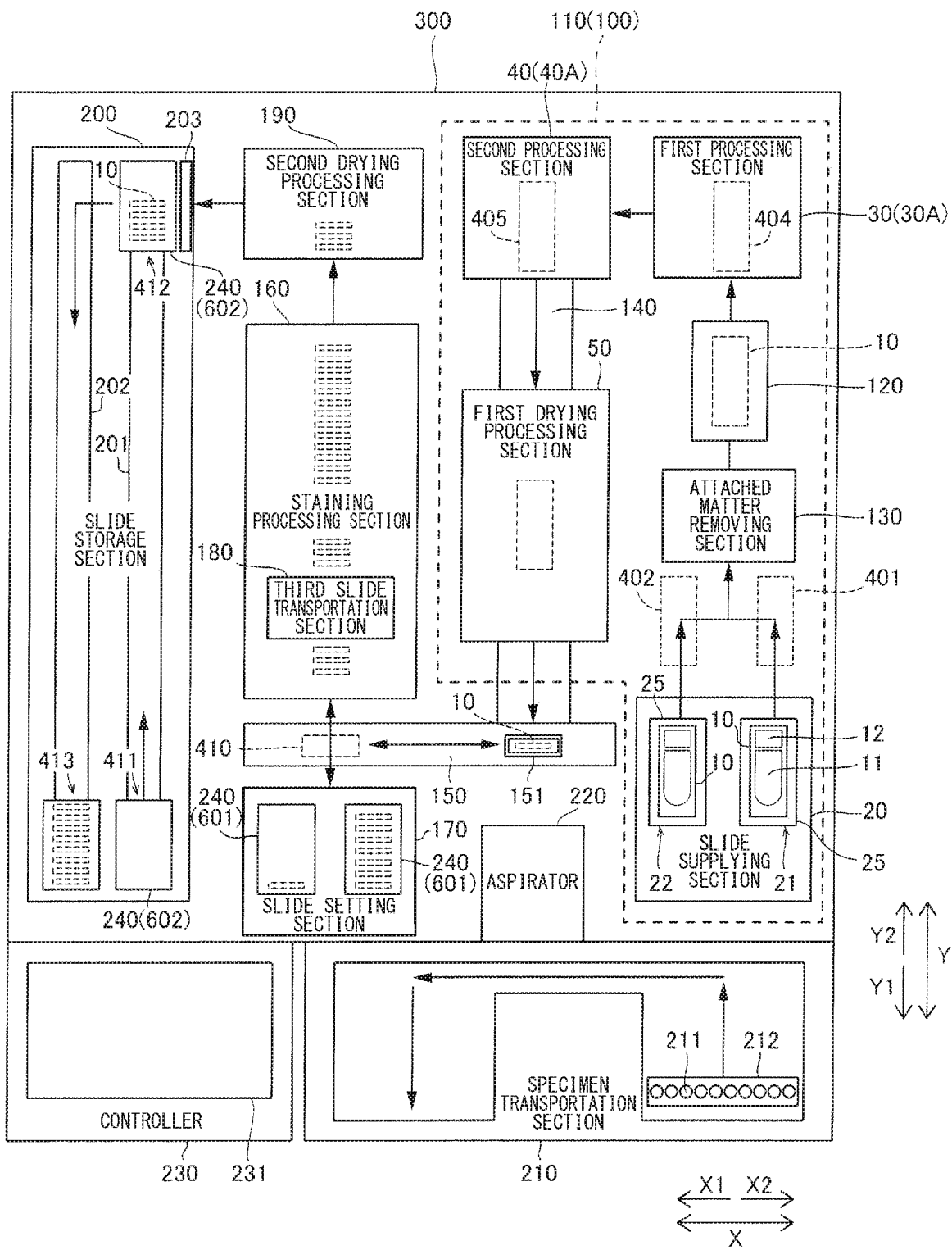
FIG. 2 is a plan view for describing one example of an overall configuration of a smear sample preparing apparatus.

In the configuration example shown in FIG. 2, the specimen smearing apparatus 100 which includes the slide supplying section 20, the first processing section 30, the second processing section 40, and the first drying processing section 50 shown in FIG. 1 is provided as a smearing section 110 of the smear sample preparing apparatus 300. In the configuration example shown in FIG. 2, the smearing section 110 further includes a first slide transportation section 120, an attached matter removing section 130, and a sending-out mechanism 140. In addition, in the configuration example shown in FIG. 2, the smear sample preparing apparatus 300 includes a second slide transportation section 150, a staining processing section 160, a slide setting section 170, a third slide transportation section 180, a second drying processing section 190, and a slide storage section 200. In the configuration example shown in FIG. 2, the smear sample preparing apparatus 300 further includes a specimen transportation section 210, an aspirator 220, and a controller 230.

In the following, two directions orthogonal to each other in a plane that is parallel to the installation surface of the smear sample preparing apparatus 300 (i.e., in a horizontal plane) is defined as an X direction and a Y direction, respectively. In the example shown in FIG. 2, the smear sample preparing apparatus 300 has a quadrangular outer shape along the X direction and the Y direction in a plan view. The X direction is defined as the left-right direction of the smear sample preparing apparatus 300, and the Y direction is defined as the depth direction of the smear sample preparing apparatus 300. A Y1 direction side is the near side of the apparatus, and a Y2 direction side is the far side of the apparatus. In addition, an up-down direction orthogonal to the horizontal surface is defined as a Z direction. In the configuration example in FIG. 2, an example is shown in which the first direction is aligned with the Y2 direction, the second direction is aligned with the X1 direction, and the third direction is aligned with the Y1 direction.

The specimen transportation section 210 is disposed at the nearest side in the smear sample preparing apparatus 300. In the specimen transportation section 210, a plurality of specimen containers 211 each containing a specimen are set, and each of the specimen containers 211 set therein is transported to a predetermined taking-in position. With respect to the specimen containers 211, the specimen transportation section 210 transports a rack 212 holding a plurality of the specimen containers 211, for example. The aspirator 220 aspirates a liquid specimen such as blood or urine from a specimen container 211 having been transported to the taking-in position by the specimen transportation section 210. The aspirator 220 supplies the aspirated specimen to the smearing section 110.

In the configuration example shown in FIG. 2, the slide supplying section 20 includes a first supplying section 21 and a second supplying section 22. The slide supplying section 20 may include one, or three or more supplying sections. With respect to the slide supplying section 20, many unused glass slides 10 having no specimen smeared thereon can be stored in each of the first supplying section 21 and the second supplying section 22. The glass slides 10 are each stored flat such that the smear surface thereof faces upward, in the first supplying section 21 and the second supplying section 22. The slide supplying section 20 is configured to hold each glass slide 10 such that the longitudinal direction of the glass slide 10 is aligned with the Y direction (the first direction and the third direction) and the short direction of the glass slide 10 is aligned with the X direction (the second direction).

The first supplying section 21 and the second supplying section 22 have a substantially identical configuration. The first supplying section 21 and the second supplying section 22 are arranged alongside each other in the X direction. Each of the first supplying section 21 and the second supplying section 22 can supply the glass slides 10 one by one, by causing each glass slide 10 accommodated therein and not yet being subjected to smearing, to move in the Y2 direction.

In the configuration example shown in FIG. 2, the first slide transportation section 120 is provided so as to transport the glass slide 10, by moving at least among the slide supplying section 20, the first processing section 30, and the second processing section 40. That is, the first slide transportation section 120 functions as a transportation section that is used in common among the slide supplying section 20, the first processing section 30, and the second processing section 40. Accordingly, compared with a case where a dedicated transportation section is individually provided for each of the slide supplying section 20, the first processing section 30, and the second processing section 40, the apparatus configuration can be simplified and downsized. A configuration may be employed in which the transportation of the glass slide 10 among the slide supplying section 20, the first processing section 30, and the second processing section 40 may be performed by separate slide transportation sections.

The first slide transportation section 120 can transport one glass slide 10, with the glass slide 10 held on the upper face of the first slide transportation section 120, for example. The first slide transportation section 120 can receive a glass slide 10 from the first supplying section 21. The first slide transportation section 120 can receive a glass slide 10 from the second supplying section 22. The first slide transportation section 120 can move in the horizontal direction (the X-Y directions). The first slide transportation section 120 can cause the held glass slide 10 to move in the up-down direction (the Z direction). The first slide transportation section 120 can transport the held glass slide 10 to the processing position of each of the attached matter removing section 130, the first processing section 30, and the second processing section 40. The first slide transportation section 120 transports the glass slide 10 received from the slide supplying section 20, to the attached matter removing section 130, the first processing section 30, and the second processing section 40 in this order. The glass slide 10, in a state of being held by the first slide transportation section 120, is subjected to a predetermined process in each of the attached matter removing section 130, the first processing section 30, and the second processing section 40. The first slide transportation section 120 may be able to hold a plurality of the glass slides. The first slide transportation section 120 may be able to move in the X-Y directions and unable to move in the Z direction.

In the configuration example shown in FIG. 2, the first slide transportation section 120 transports the glass slide 10, with the longitudinal direction of the glass slide 10 aligned with the first direction (the Y2 direction) and with the short direction of the glass slide 10 aligned with the second direction (the X direction). Accordingly, the transport route for the glass slide 10 in the second direction (the X direction) which is the left-right direction of the smear sample preparing apparatus 300 can be shortened. That is, the route between the first processing section 30 and the second processing section 40 can be shortened. As a result, the outer dimension in the left-right direction (the X direction) of the apparatus can be reduced. This makes it possible to easily ensure the installation space in the left-right direction, which is important in a use mode in which the smear sample preparing apparatus 300 and relating apparatuses are arranged in the left-right direction.

The attached matter removing section 130 has a function of removing attached matters attached to the surface of the glass slide 10. The attached matter removing section 130 performs an attached matter removing process on the glass slide 10 in a state of being held on the upper face of the first slide transportation section 120. For example, the attached matter removing section 130 is connected to a pressure source not shown and discharges air, thereby being able to blow off attached matters in the smear region 11 and the printing region 12 of the glass slide 10. The attached matters are small foreign bodies such as glass powder and dust, for example.

In the configuration example shown in FIG. 2, the first processing section 30 is implemented as a printing processing section which performs a printing process as the first process. The first processing section 30 can print various types of information such as specimen information, onto the printing region 12 of the glass slide 10. The first processing section 30 performs printing on the glass slide 10 in a state of being held on the upper face of the first slide transportation section 120.

In the configuration example shown in FIG. 2, the second processing section 40 is implemented as a smearing processing section which performs a smearing process as the second process. The second processing section 40 can smear a specimen onto the smear region 11 of the glass slide 10. The second processing section 40 performs smearing of a specimen onto the glass slide 10 in a state of being held on the upper face of the first slide transportation section 120.

In the configuration example shown in FIG. 2, the first processing section 30 and the second processing section 40 are disposed so as to be adjacent to each other in the second direction (the X1 direction).

In the configuration example shown in FIG. 2, the first slide transportation section 120 is configured to transport a first glass slide 10 from the first processing section 30 to the second processing section 40, and then, to receive a next second glass slide 10 from the slide supplying section 20. The first glass slide and the second glass slide mean, of two glass slides 10 sequentially transported by the first slide transportation section 120, a preceding glass slide and a subsequent glass slide, respectively. Accordingly, for example, when compared with a case where the first slide transportation section 120 transports a glass slide 10 to the first drying processing section 50, the transport route for the first slide transportation section 120 can be suppressed from becoming longer than necessary. Thus, even in a case where the first slide transportation section 120 which is used in common among the slide supplying section 20, the first processing section 30, and the second processing section 40 is provided, the time period after the first glass slide 10 has been transported to the second processing section 40 until the next second glass slide 10 is transported to the first processing section 30 can be shortened.

In the configuration example shown in FIG. 2, the sending-out mechanism 140 has a function of sending out the glass slide 10 having been transported to the second processing section 40, to the first drying processing section 50. Thus, when the first slide transportation section 120 transports the glass slide 10 to the second processing section 40 and then the process at the second processing section 40 is completed, the glass slide 10 can be promptly transported to the first drying processing section 50 by the sending-out mechanism 140 provided separately from the first slide transportation section 120. The sending-out mechanism 140 causes the glass slide 10 having been transported to the second processing section 40, to move in the Y1 direction (the third direction), thereby to locate the glass slide 10 at the processing position of the first drying processing section 50.

The first drying processing section 50 has a function of receiving from the second processing section 40 the glass slide 10 having a specimen smeared thereon, and of blowing air to the smear region 11 of the glass slide 10. The first drying processing section 50 can dry, by blowing air, the specimen smeared on the glass slide 10.

In the configuration example shown in FIG. 2, the sending-out mechanism 140 is configured to further send out the glass slide 10 having been sent out to the first drying processing section 50, from the first drying processing section 50 to the second slide transportation section 150. The sending-out mechanism 140 causes the glass slide 10 having been transported to the first drying processing section 50, to move in the Y1 direction (the third direction), thereby to deliver the glass slide 10 to the second slide transportation section 150 as a third transportation section.

The second slide transportation section 150 is disposed at the Y1 direction side (the third direction side) of the first drying processing section 50 and the staining processing section 160, and is provided so as to extend in the X direction. The second slide transportation section 150 is configured to transport, in the X1 direction (the second direction), the glass slide 10 from the first drying processing section 50 to a taking-out position 410 between the staining processing section 160 and the slide setting section 170. The second slide transportation section 150 has an accommodation part 151 for accommodating the glass slide 10, and can cause the accommodation part 151 to move in the X direction. The second slide transportation section 150 receives in the accommodation part 151 the glass slide 10 in a state of being laid substantially parallel to the installation surface, brings the glass slide 10 into a state of standing substantially perpendicularly to the installation surface, and then, transports the glass slide 10 to the taking-out position 410. Thus, at the taking-out position 410, the glass slide 10 is held in a state in which the smear surface thereof stands along the up-down direction (the Z direction). The glass slide 10 transported to the taking-out position 410 is transported to the staining processing section 160 or the slide setting section 170.

The staining processing section 160 is configured to stain the specimen smeared on the glass slide 10. The staining processing section 160 is arranged alongside the first drying processing section 50, at the second direction side (the X1 direction side) with respect to the first drying processing section 50, and is configured to receive the glass slide 10 transported in the second direction from the first drying processing section 50. Accordingly, the transport route for the glass slide 10 from the slide supplying section 20, via the first processing section 30, the second processing section 40, and the first drying processing section 50, to the staining processing section 160 can be formed as a route (see FIG. 3) that meanders in the order of the first direction (the Y2 direction), the second direction (the X1 direction), the third direction (the Y1 direction), and the second direction (the X1 direction). In this case, various types of processing sections arranged in the first direction and the third direction can be disposed in a shape of a plurality of columns in the second direction, and thus, occurrence of wasted space can be suppressed. As a result, even when the staining processing section 160 is provided, increase in the size of the apparatus can be suppressed.

The staining processing section 160 is provided so as to extend in the Y direction. The staining processing section 160 includes a staining chamber which stores a staining liquid, and a washing chamber which stores a washing liquid. In the staining processing section 160, a staining process and a washing process are performed in the staining chamber and the washing chamber, respectively, on a smeared glass slide 10.

The slide setting section 170 is disposed at the third direction side (the Y1 direction side) of the staining processing section 160, and is configured to hold the glass slide 10 such that the glass slide 10 can be taken therein and out therefrom. In the slide setting section 170, two first storage containers 601 each capable of storing a plurality of the glass slides 10 can be set. As the first storage container 601, a slide storage container 240 (see FIG. 13) described later can be used. The slide setting section 170 includes the slide storage container 240 and holds the glass slides 10 in the slide storage container 240.

The third slide transportation section 180 can transport the glass slide 10 among the staining processing section 160, the slide setting section 170, and the taking-out position 410. The third slide transportation section 180 can move, in each of the X direction, the Y direction, and the Z direction, at height positions above the staining processing section 160, the slide setting section 170, and the taking-out position 410, for example. Thus, the third slide transportation section 180 can grip and take out the glass slide 10 disposed at each of the staining processing section 160, the slide setting section 170, and the taking-out position 410, and can transport the glass slide 10 to each of the staining processing section 160, the slide setting section 170, and the taking-out position 410. The taking-out position 410 can be a position between the staining processing section 160 and the slide setting section 170. Accordingly, the taking-out position 410 can be a position that is near both of the staining processing section 160 and the slide setting section 170, and thus, the glass slide 10 can be efficiently transported from the taking-out position 410 to both of the staining processing section 160 and the slide setting section 170.

With the configuration in which the third slide transportation section 180 transports the glass slide 10 among the staining processing section 160, the slide setting section 170, and the taking-out position 410, the smear sample preparing apparatus 300 can cause the glass slide 10 having been subjected to the printing process and the smearing process in the smearing section 110, to be transported not only from the taking-out position 410 to the staining processing section 160, but also from the taking-out position 410 to the slide setting section 170. In addition, the smear sample preparing apparatus 300 can cause a glass slide 10 having a specimen smeared thereon and manually set by the user in the slide setting section 170, to be transported from the slide setting section 170 to the staining processing section 160. Accordingly, in addition to the operation in a normal mode in which the printing process, the smearing process, and the staining process are performed, it becomes possible to perform an operation in a smear mode in which a glass slide 10 having been subjected to the printing process and the smearing process in the smearing section 110 is sent out to the slide setting section 170 without being subjected to the staining process, and an operation in a stain mode in which a glass slide 10 having a specimen smeared thereon and manually set by the user in the slide setting section 170 is subjected to the staining process by the staining processing section 160, to be sent out to the slide storage section 200. Since various operations according to the need of the user can be performed, the convenience of the apparatus is improved. Since the slide setting section 170 is disposed at the near side of the staining processing section 160, the user can perform the setting work and collecting work of the slide storage container 240 with respect to the slide setting section 170, or the setting work and collecting work of the glass slide 10 with respect to the slide storage container 240, at the near side of the apparatus, as in the case of the slide supplying section 20. Thus, the user can further easily perform his/her work, and the usability of the smear sample preparing apparatus 300 is further improved.

It should be noted that, in the configuration example shown in FIG. 2, the slide supplying section 20 and the slide setting section 170 are each arranged at the first direction (the Y2 direction) side with respect to the specimen transportation section 210. In the case of the configuration example shown in FIG. 2, the slide supplying section 20 and the slide setting section 170 are adjacent to the specimen transportation section 210 at the first direction (the Y2 direction side) side with respect to the specimen transportation section 210. Accordingly, the slide supplying section 20 and the slide setting section 170 can be arranged alongside each other at a position near the specimen transportation section 210 which is disposed at the near side of the apparatus. Thus, the portion where the user preforms work can be intensively located at the near side of the apparatus. Thus, the positions for the setting work of a specimen container 211 to the specimen transportation section 210, the setting work of a new glass slide 10 to the slide supplying section 20, the taking-out work or setting work of a glass slide 10 having a specimen smeared thereon with respect to the slide setting section 170 can be intensively located at positions near the near side of the apparatus. Accordingly, the user can easily perform his/her work, and thus, the convenience of the apparatus is improved.

In the configuration example shown in FIG. 2, the third slide transportation section 180 can transport the glass slide 10 not only to the staining processing section 160, the slide setting section 170, and the taking-out position 410, but also to the second drying processing section 190 and the slide storage section 200. The transportation of the glass slide 10 to the second drying processing section 190 and the slide storage section 200 may be performed by a transportation section different from the third slide transportation section 180.

In the configuration example shown in FIG. 2, the second drying processing section 190 is arranged alongside the staining processing section 160, at the first direction side (the Y2 direction side) with respect to the staining processing section 160. The second drying processing section 190 receives the glass slide 10 transported in the first direction from the staining processing section 160. Accordingly, the transport route for the glass slide 10 from the slide supplying section 20, via the first processing section 30, the second processing section 40, the first drying processing section 50, and the staining processing section 160, to the second drying processing section 190 can be formed as a route (see FIG. 3) that meanders in the order of the first direction (the Y2 direction), the second direction (the X1 direction), the third direction (the Y1 direction), the second direction (the X1 direction), and the first direction (the Y2 direction). In this case, various types of processing sections arranged in the first direction and the third direction can be disposed in a plurality of columns in the second direction, and thus, occurrence of wasted space can be suppressed. As a result, even when the second drying processing section 190 is provided, increase in the size of the apparatus can be suppressed. In the configuration example shown in FIG. 2, the second drying processing section 190 and the staining processing section 160 are disposed adjacent to each other in the first direction (the Y2 direction).

The second drying processing section 190 has a function of drying, by blowing air, the glass slide 10 having been subjected to staining in the staining processing section 160, for example. The second drying processing section 190 delivers the dried glass slide 10 to the slide storage section 200.

The slide storage section 200 has a function of receiving and storing the glass slide 10 for which the processes have ended. In the configuration example shown in FIG. 2, the slide storage section 200 is arranged alongside the second drying processing section 190, at the second direction side (the X1 direction side) with respect to the second drying processing section 190, and receives the glass slide 10 transported in the second direction from the second drying processing section 190. Accordingly, the transport route for the glass slide 10 from the slide supplying section 20, via the first processing section 30, the second processing section 40, the first drying processing section 50, the staining processing section 160, and the second drying processing section 190, to the slide storage section 200 can be formed as a route (see FIG. 3) that meanders in the order of the first direction (the Y2 direction), the second direction (the X1 direction), the third direction (the Y1 direction), the second direction (the X1 direction), the first direction (the Y2 direction), and the second direction (the X1 direction). In this case, various types of processing sections arranged in the first direction and the third direction can be disposed in a plurality of columns in the second direction, and thus, occurrence of wasted space can be suppressed. As a result, even when the slide storage section 200 is provided, increase in the size of the apparatus can be suppressed.

In the slide storage section 200, a plurality of second storage containers 602 can be set. As the second storage container 602, the slide storage container 240 described later (see FIG. 13) can be used. That is, the slide storage section 200 includes the slide storage container 240, and holds the glass slides 10 in the slide storage container 240. In the slide storage section 200, an empty slide storage container 240 set at a setting position 411 is moved in the first direction (the Y2 direction) to a storing position 412. The storing position 412 is a position adjacent at the second direction side to the second drying processing section 190. The third slide transportation section 180 causes the glass slide 10 to move from the second drying processing section 190 in the second direction, and sets the glass slide 10 for which the processes have ended, into the slide storage container 240 at the storing position 412. In the slide storage section 200, the slide storage container 240 accommodating the glass slide 10 is moved in the X1 direction and then in the Y1 direction, to be located at a collecting position 413. The setting position 411 and the collecting position 413 are positions arranged alongside the slide supplying section 20 and the slide setting section 170 in the X direction. The user can take out the slide storage container 240 disposed at the setting position 411.

In the configuration example shown in FIG. 2, the slide storage section 200 includes a first transport path 201 and a second transport path 202. The first transport path 201 causes the slide storage container 240 to move in the first direction (the Y2 direction), from the setting position 411 at which the slide storage container 240 for storing the glass slides 10 is set, to the storing position 412 at which the glass slides 10 from the second drying processing section 190 are stored in the slide storage container 240. The second transport path 202 causes the slide storage container 240 storing the glass slides 10 at the storing position 412, to move in the third direction (the Y1 direction), to the collecting position 413 arranged alongside the setting position 411, at the second direction (the X1 direction) side with respect to the setting position 411. Accordingly, the slide storage container 240 before and after the glass slides 10 are stored can be transported in the first direction (the Y2 direction) and the third direction (the Y1 direction). Thus, the width in the second direction (the X1 direction) of the slide storage section 200 can be suppressed. Due to the configuration in which the setting position 411 and the collecting position 413 are disposed at the near side (the third direction side) of the apparatus body, the setting work and collecting work of the slide storage container 240 in the slide storage section 200 can be performed at the near side of the apparatus, as in the case of the slide supplying section 20. Thus, the user can further easily perform his/her work, and the usability of the smear sample preparing apparatus 300 is further improved.

The first transport path 201 and the second transport path 202 are each a belt conveyance mechanism, for example, and each extend linearly in the Y direction (the first direction and the third direction). The first transport path 201 and the second transport path 202 can each transport a slide storage container 240 set on the belt, along the Y direction and independently of each other, by means of a motor not shown. In the configuration example shown in FIG. 2, the slide storage section 200 includes a laterally-sending part 203. The laterally-sending part 203 causes the slide storage container 240 storing the glass slides 10 to move from the first transport path 201 to the second transport path 202. The laterally-sending part 203 can move in the second direction (the X1 direction). The laterally-sending part 203 comes into contact with the slide storage container 240 disposed at the storing position 412, to cause the slide storage container 240 to move in the second direction (the X1 direction) to the second transport path 202.

The controller 230 includes a CPU and a memory not shown, and controls operation of each section of the smear sample preparing apparatus 300. The controller 230 includes an output unit 231. The output unit 231 is a display unit such as a liquid crystal monitor, for example. The output unit 231 may be a printer.

With this configuration, the smear sample preparing apparatus 300 performs the processes of the printing process, the specimen smearing process, and the staining process on the glass slide 10, thereby being able to automatically prepare a smear sample.

<Transport Route for Glass Slide>

Figure 3:
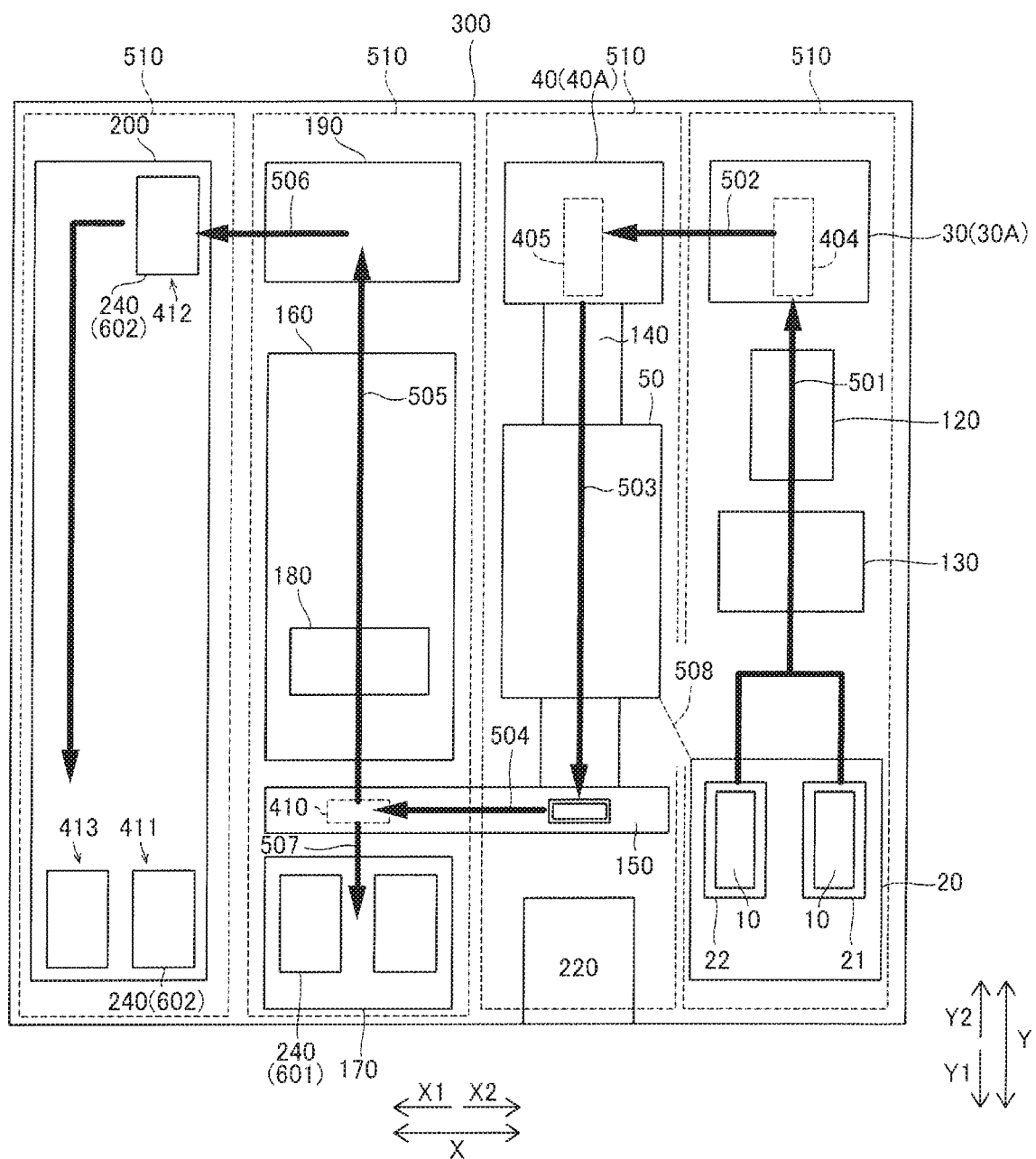
FIG. 3 is a diagram showing a transport route of a glass slide in the smear sample preparing apparatus shown in FIG. 2.

As shown in FIG. 3, the transport route for the glass slide 10 from the slide supplying section 20 to the slide storage section 200 extends along a route 501 in the first direction (the Y2 direction), a route 502 in the second direction (the X1 direction), a route 503 in the third direction (the Y1 direction), a route 504 in the second direction (the X1 direction), a route 505 in the first direction (the Y2 direction), and a route 506 in the second direction (the X1 direction). In a case where the staining process is not performed, the transport route from the slide supplying section 20 to the slide setting section 170 is a route that extends along a route 507 in the third direction (the Y1 direction) after the route 504. The transportation of the glass slide 10 is completed only in the forward direction, without being reversed. In the example shown in FIG. 3, roughly speaking, the slide supplying section 20, the first processing section 30, the second processing section 40, and the first drying processing section 50 are respectively disposed at corner portions of the quadrangle region formed by the route 501, the route 502, the route 503, and an imaginary line 508 which connects the slide supplying section 20 and the first drying processing section 50.

According to the configuration example shown in FIG. 2 and FIG. 3, in the smear sample preparing apparatus 300, the processing sections are disposed in a column shape along the depth direction (the Y direction) of the apparatus, and a total of four columns 510 of the processing sections are arranged in the X direction. Then, a transport route that meanders in a reversed W shape is configured such that: the glass slide 10 is transported in the first direction (the Y2 direction) or the third direction (the Y1 direction) from one end of a column 510 of the processing sections extending along the Y direction to the other end of the column 510, and then, transported in the second direction (the X2 direction), whereby the glass slide 10 is transported to an adjacent column 510 of the processing sections. As a result, also in the smear sample preparing apparatus 300 in which many processing sections are disposed, the processing sections can be disposed with dead space reduced as much as possible, and thus, the apparatus can be downsized.

<Configuration of First Slide Transportation Section>

Next, a configuration example of the first slide transportation section 120 is described with reference to FIG. 4.

Figure 4:
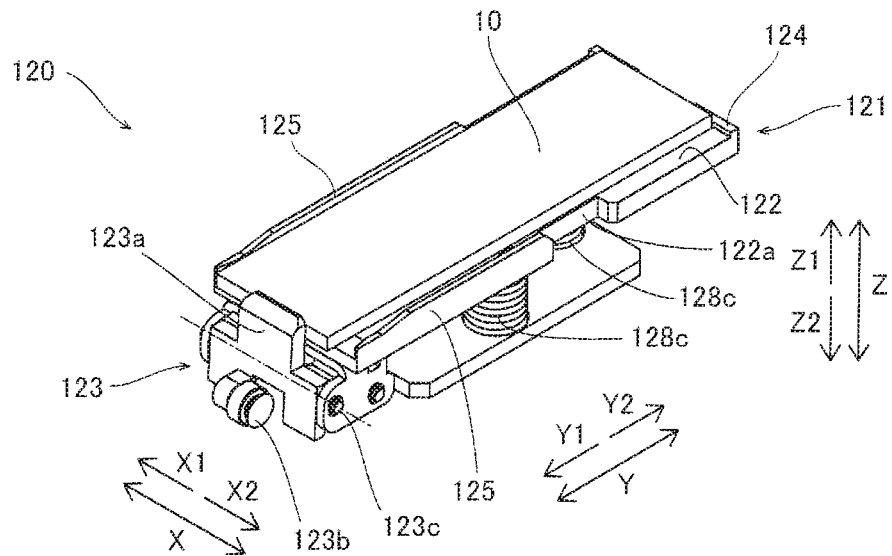
FIG. 4 is a perspective view showing a specific configuration example of a first slide transportation section.

In the configuration example shown in FIG. 4, the first slide transportation section 120 includes a holding member 121. The holding member 121 includes a placement part 122, a grip part 123, a contact part 124, and a wall part 125.

The holding member 121 is configured so as to be able to hold a glass slide 10 being placed on the upper face of the placement part 122. Specifically, the holding member 121 holds the glass slide 10 so as to be disposed flat on the upper face of the placement part 122 such that the smear surface thereof faces upward. The placement part 122 supports the glass slide 10 from the lower side (Z2 direction side). The first slide transportation section 120 can cause, by means of a movement mechanism described later, the holding member 121 holding the glass slide 10 on the upper face thereof, to move to the first processing section 30 and the second processing section 40. Accordingly, the flatly disposed glass slide 10 which can be subjected, as it is, to the printing process and the smearing process can be transported to the first processing section 30 and the second processing section 40. Thus, there is no need to change the attitude of the glass slide 10 after being transported to the first processing section 30 and the second processing section 40, and thus, the printing process and the smearing process can be promptly performed. The placement part 122 is formed in a plate-like shape extending in the horizontal direction (the X-Y directions).

The grip part 123 includes a pressing part 123a, an opening/closing part 123b, and a rotation shaft 123c. The grip part 123 can move between an open position 421 (see FIG. 7) at which the glass slide 10 is allowed to be taken in and out, and a grip position 422 (see FIG. 6) at which the glass slide 10 is held. By means of the grip part 123, the glass slide 10 can be held so as not to move on the holding member 121. Accordingly, while the glass slide 10 is allowed to be taken in and out with respect to the holding member 121, and the glass slide 10 set on the holding member 121 can be stably transported. In addition, as described later, also with respect to the glass slide 10 on the holding member 121 in the printing process and the smearing process at the first processing section 30 and the second processing section 40, positional displacement of the glass slide 10 being processed can be suppressed.

In the configuration example shown in FIG. 3, the grip part 123 is disposed at the Y1 direction side of the holding member 121. At the end on the Y2 direction side on the upper face of the placement part 122, the contact part 124 is provided so as to protrude upwardly. The grip part 123 can rotate toward the Y1 direction side and the Y2 direction side about the rotation shaft 123c extending in the X direction. The pressing part 123a of the grip part 123 can come into contact with the Y1 direction side of the glass slide 10, to press the glass slide 10 to the Y2 direction side. The grip part 123 is pulling the pressing part 123a toward the Y2 direction side, by means of a spring member not shown. Accordingly, the grip part 123 presses an end face of the glass slide 10 on the upper face of the placement part 122 to the contact part 124 at the Y2 direction side, thereby gripping the short sides of the glass slide 10 in the longitudinal direction.

The grip part 123 has the opening/closing part 123b provided at the opposite side to the pressing part 123a, with respect to the rotation shaft 123c. That is, the pressing part 123a is disposed at the upper side (Z1 direction side) with respect to the rotation shaft 123c. The opening/closing part 123b is disposed at the lower side (the Z2 direction side) with respect to the rotation shaft 123c. The grip part 123 can rotate toward the Y1 direction side about the rotation shaft 123c against the tensile force of the spring member, by the opening/closing part 123b being pressed toward the Y2 direction side. With this configuration, the grip part 123 can move between the open position 421 at which the glass slide 10 is allowed to be taken therein and thereout as a result of the pressing part 123a receding below the upper face of the placement part 122, and the grip position 422 at which the glass slide 10 is held as a result of the pressing part 123a protruding above the upper face of the placement part 122.

The holding member 121 includes the wall part 125 for restricting movement of the glass slide 10 placed on the holding member 121. Accordingly, positional displacement of the glass slide 10 on the holding member 121 can be suppressed, and thus, the glass slide 10 can be prevented from extending to the outside of the holding member 121. As a result, the accuracy of the transport position of the glass slide 10 by the first slide transportation section 120 can be improved.

A pair of the wall parts 125 are provided at both ends in the X direction of the holding member 121, respectively. The pair of the wall parts 125 are provided in a direction orthogonal to the direction in which the holding member 121 receives the glass slide 10 from the first supplying section 21 or the second supplying section 22. That is, the pair of the wall parts 125 are respectively provided at ends in the short direction which is orthogonal to the longitudinal direction along which the glass slide 10 is gripped by the grip part 123.

In the configuration example shown in FIG. 4, at the end on the X2 direction side of the holding member 121, a cut-off part 122a obtained by cutting by a predetermined length toward the X1 direction side is provided. The cut-off part 122a is formed in the Y2 direction with respect to the center in the Y direction of the placement part 122. A pressing part (not shown) moves, in the X1 direction, from the X2 direction side of the holding member 121 to the inner side of the cut-off part 122a, whereby the glass slide 10 on the upper face of the placement part 122 can be moved to the X1 side. Accordingly, as a result of the end face of the glass slide 10 coming into contact with the wall part 125 at the X1 side, the positioning in the X direction of the glass slide 10 on the holding member 121 can be realized. It should be noted that, as a result of the grip part 123 causing the end face of the glass slide 10 to come into contact with the contact part 124, positioning in the Y direction of the glass slide 10 on the holding member 121 is realized.

<Configuration of Movement Mechanism of First Slide Transportation Section>

Figure 5:
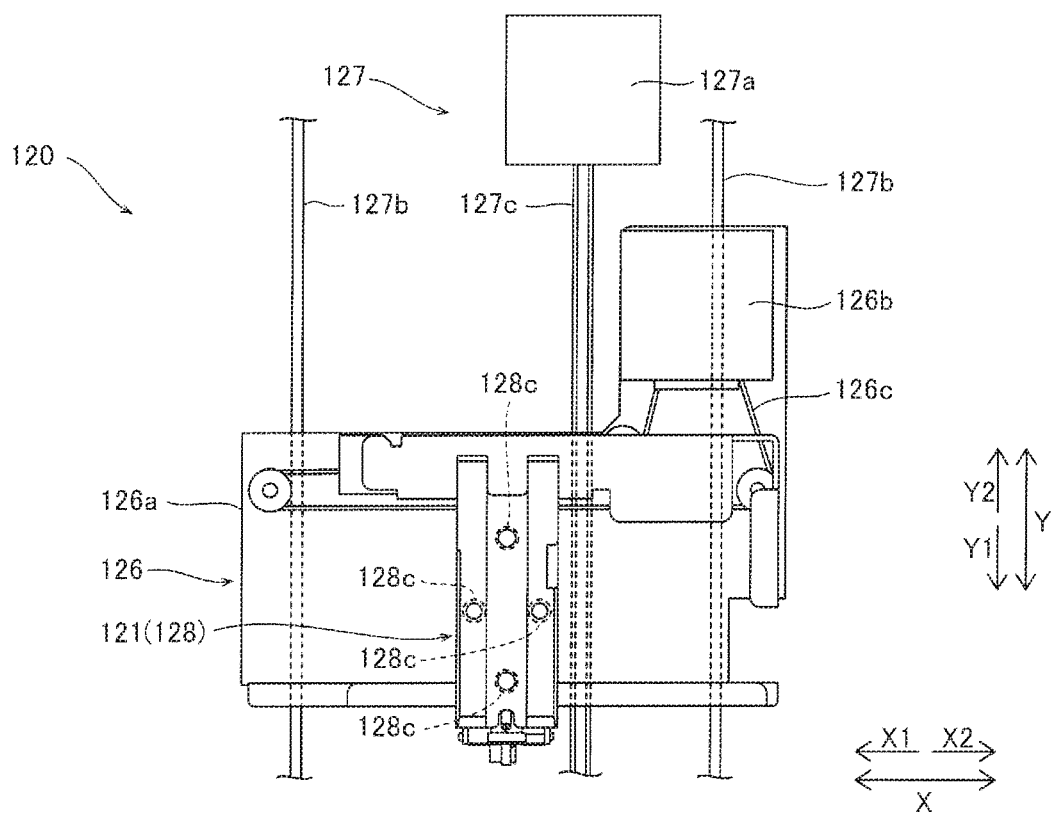
FIG. 5 is a plan view showing the specific configuration example of the first slide transportation section.
Figure 6:
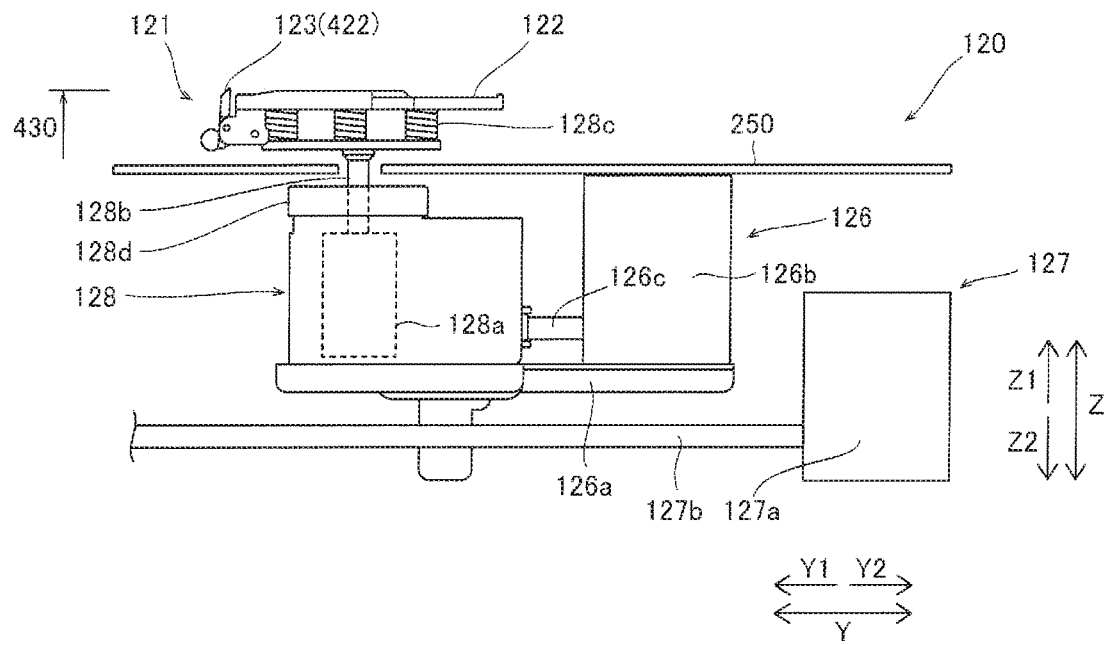
FIG. 6 is a side view showing the specific configuration example of the first slide transportation section.

In the configuration example shown in FIG. 5 and FIG. 6, the first slide transportation section 120 includes a first movement mechanism 126, a second movement mechanism 127, and a third movement mechanism 128. The first movement mechanism 126 can cause the held glass slide 10 to move in the X direction. The second movement mechanism 127 can cause the held glass slide 10 to move in the Y direction. The third movement mechanism 128 can cause the held glass slide 10 to move in the Z direction. Accordingly, the first slide transportation section 120 can cause the glass slide 10 to move along a horizontal plane and the up-down direction.

In the configuration example shown in FIG. 5 and FIG. 6, the first movement mechanism 126 is implemented as a belt-driven-type direct acting mechanism including a base part 126a, a motor 126b, a belt 126c, and a rail not shown. The second movement mechanism 127 is implemented as a belt-driven-type direct acting mechanism including a motor 127a, a pair of rails 127b, and a belt 127c. The third movement mechanism 128 (see FIG. 6) is implemented as an air-driven mechanism including an air cylinder 128a.

The holding member 121 is supported so as to be movable in the up-down direction by the third movement mechanism 128. The air cylinder 128a can expand and contract the rod 128b in the up-down direction (the Z direction). The holding member 121 is mounted to the rod 128b through an elastic member 128c provided at the upper end of the rod 128b. The rod 128b is provided with a contact member 128d at the lower side of the holding member 121 and the elastic member 128c. The air cylinder 128a causes the holding member 121, the elastic member 128c, and the contact member 128d to move in the up-down direction through advancement and retraction of the rod 128b. The air cylinder 128a is connected to an air pressure source used in common with the attached matter removing section 130, and does not need a dedicated drive source.

In the configuration example shown in FIG. 5 and FIG. 6, the elastic member 128c is implemented as a helical compression spring, for example. A plurality of the elastic members 128c are disposed so as to surround the position of the center of gravity of the holding member 121 (see FIG. 5). For example, two elastic members 128c are disposed, separated by a predetermined interval, in the longitudinal direction (the Y direction) of the held glass slide 10, and two elastic members 128c are disposed, separated by a predetermined interval, in the short direction (the X direction). That is, four elastic members 128c are disposed at vertexes of a rhombus, respectively. The elastic members 128c have a function of adjusting the attitude of the glass slide 10 held by the holding member 121. Each elastic member 128c may be a cushion member such as rubber.

As shown in FIG. 6, a restriction member 250 is provided at a predetermined height position between the holding member 121 and the contact member 128d. The restriction member 250 has a flat plate shape and is disposed so as to extend along the X-Y directions, for example. The restriction member 250 has formed therein a penetrating groove for allowing the rod 128b to pass therethrough. The restriction member 250 can perform positioning of the raised position of the holding member 121, by coming into contact with the contact member 128d raised by the air cylinder 128a. The contact member 128d is formed in a rectangular parallelepiped shape having a size that cannot pass through the penetrating groove, and is fixed to the rod 128b. The contact member 128d is made from a resin material, for example, which preferably has a small sliding resistance.

The third movement mechanism 128 is supported so as to be movable in the X direction by the first movement mechanism 126. The motor 126b, the belt 126c, and the rail of the first movement mechanism 126 are disposed on the base part 126a. The belt 126c is rotated by being driven by the motor 126b, whereby the holding member 121 is moved in the X direction together with the third movement mechanism 128. The base part 126a is set on the rails 127b of the second movement mechanism 127, and can move in the Y direction.

The first movement mechanism 126 is supported so as to be movable in the Y direction by the second movement mechanism 127. The second movement mechanism 127 can cause the holding member 121 to move in the Y direction, by causing the base part 126a to move in the Y direction. Specifically, the belt 127c is rotated by being driven by the motor 127a, whereby the holding member 121, the third movement mechanism 128, and the first movement mechanism 126 are moved together in the Y direction.

<Configuration of Slide Supplying Section>

Figure 7:
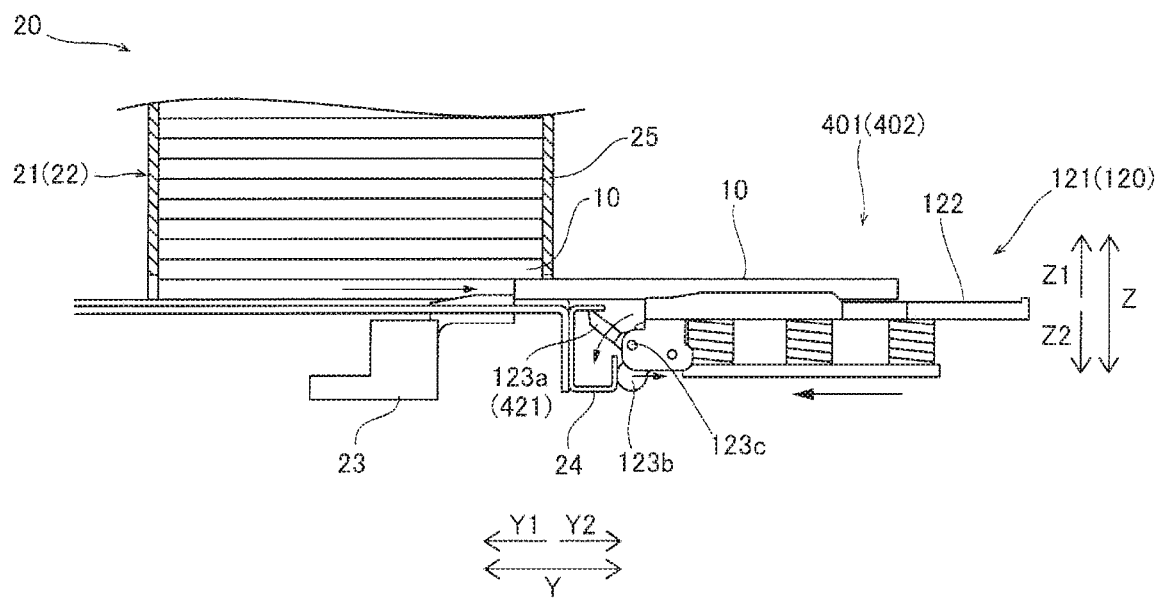
FIG. 7 is a schematic side view showing a slide supplying section and the first slide transportation section.

In the configuration example shown in FIG. 7, the slide supplying section 20 includes: a case part 25 configured to hold, in a stacked state, a plurality of the glass slides 10 yet to be processed; and a sending-out part 23 configured to push and supply the glass slides 10 stacked in the case part 25, one by one from the case part 25. Thus, with the installation area suppressed by stacking the glass slides 10, the glass slides 10 can be supplied one by one.

Each of the first supplying section 21 and the second supplying section 22 of the slide supplying section 20 includes the case part 25 and the sending-out part 23. The case part 25 has a hollow tubular shape extending in the up-down direction (the Z direction). The case part 25 can hold therein a plurality of the glass slides 10 in a state of being stacked in the up-down direction. The case part 25 has a rectangular parallelepiped outer shape so as to surround the periphery of the glass slides 10 in a state of being stacked by a predetermined number in the up-down direction.

The sending-out part 23 is provided below each of the first supplying section 21 and the second supplying section 22. At the delivering position of the glass slide 10, a touching member 24 is provided. The first slide transportation section 120 moves in the Y1 direction so as to bring the opening/closing part 123b of the grip part 123 into contact with the touching member 24 disposed at the delivering position of the glass slide 10. Accordingly, the pressing part 123a of the grip part 123 is rotated about the rotation shaft 123c, whereby the pressing part 123a is moved to the open position 421.

The sending-out part 23 is provided so as to protrude above (in the Z1 direction) the setting surface on which the glass slide 10 is set. The protruding amount of the sending-out part 23 is smaller than the thickness of the glass slide 10. The sending-out part 23 can be moved in the Y direction by a drive source not shown such as a motor. In each of the first supplying section 21 and the second supplying section 22, a glass slide 10 is pushed out in the Y2 direction by the sending-out part 23 in a state where the grip part 123 is located at the open position 421, whereby the glass slide 10 is supplied to the first slide transportation section 120. The sending-out part 23 sends out the lowest one of the stacked glass slides 10, to the first slide transportation section 120. Accordingly, from the first supplying section 21 or the second supplying section 22, the glass slides 10 can be supplied one by one to the first slide transportation section 120.

<Configurations of First Processing Section and Second Processing Section>

Figure 8:
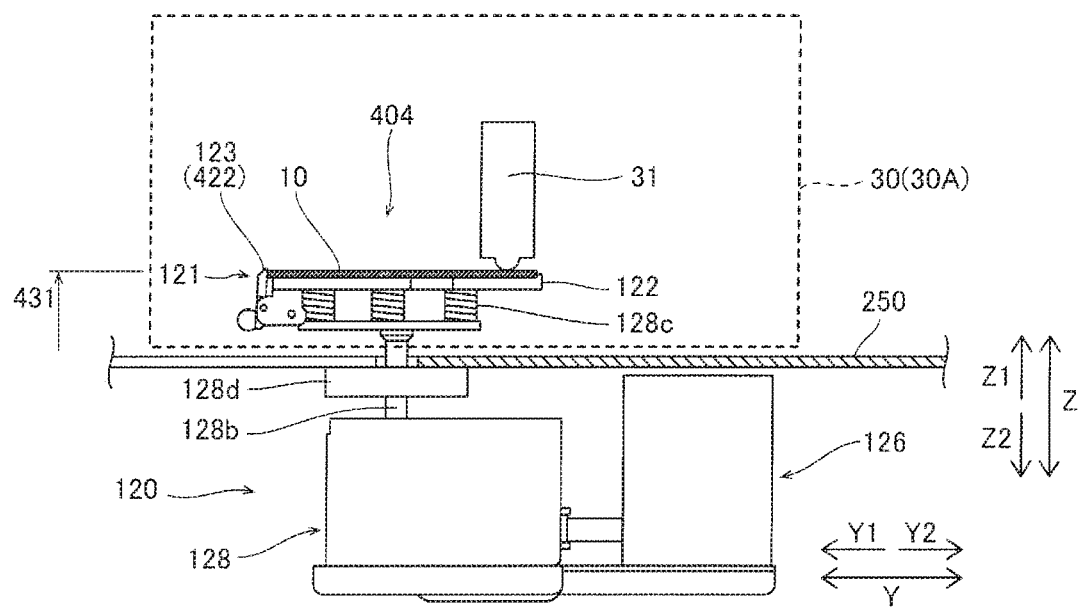
FIG. 8 is a schematic side view showing a first processing section and the first slide transportation section.
Figure 9:
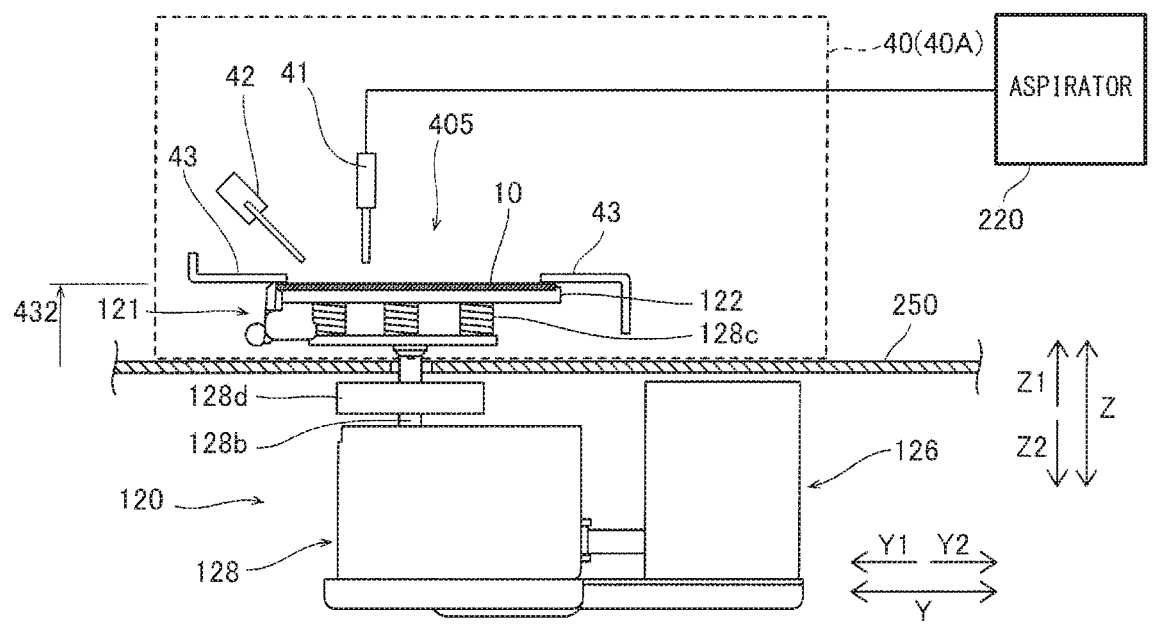
FIG. 9 is a schematic side view showing a second processing section and the first slide transportation section.

In the configuration example shown in FIG. 8 and FIG. 9, each of the first processing section 30 and the second processing section 40 is configured to perform a process on a glass slide 10 held on the upper face of the holding member 121. Accordingly, in each of the first processing section 30 and the second processing section 40, a process can be performed on the glass slide 10, as it is, on the holding member 121, without delivering the glass slide 10 on the holding member 121 to another support member. As a result, there is no need to provide a mechanism for holding the glass slide 10 to each of the first processing section 30 and the second processing section 40. Thus, the apparatus configuration for the first processing section 30 and the second processing section 40 can be simplified and downsized.

In the configuration example shown in FIG. 8, the first processing section 30 includes a printing part 31. The printing part 31 is disposed at a position above the glass slide 10 transported by the first slide transportation section 120. The printing part 31 has a print head at the lower end thereof and is configured to be movable in the up-down direction (the Z direction). In the configuration example shown in FIG. 8, since the holding member 121 of the first slide transportation section 120 can move in the X-Y directions, there is no need to provide the printing part 31 with a movement mechanism for the X-Y directions.

In a state of a lowered position 430 (see FIG. 6) where the holding member 121 has been lowered, the first slide transportation section 120 moves in the first direction (the Y2 direction), to locate the holding member 121 from the slide supplying section 20 side to the processing position of the first processing section 30. At the lowered position 430, the restriction member 250 and the contact member 128*d* are separated from each other. It should be noted that, during the movement to the first processing section 30, the removing process by the attached matter removing section 130 is performed.

As shown in FIG. 8, at the processing position of the first processing section 30, the first slide transportation section 120 raises the holding member 121. As a result of the contact member 128*d* coming into contact with the restriction member 250, the positioning to the raised position of the holding member 121 is realized. That is, the glass slide 10 on the holding member 121 is positioned, in the up-down direction, at a first process height position 431 for the first processing section 30. The first process height position 431 is the height position in a state where the contact member 128*d* is in contact with the restriction member 250. In the raised state where the positioning has been realized by the restriction member 250, the print process is performed by the first processing section 30 on the glass slide 10 held by the holding member 121.

In the first processing section 30, the printing part 31 is lowered to press the print head against the printing region 12 of the glass slide 10. At this time, slight difference in inclination between the print head and the glass slide 10 is absorbed by deformation of the elastic members 128*c* supporting the holding member 121, whereby the close contact state between the print head and the printing region 12 of glass slide 10 is ensured. The first slide transportation section 120 moves in the Y direction in a state where downward pressing force is being applied by the print head of the printing part 31, whereby printing by the printing part 31 is performed for the entirety of the printing region 12.

In the configuration example shown in FIG. 9, the second processing section 40 includes a dropping part 41 and a smearing member 42. The dropping part 41 has a function of dropping a specimen on the transported glass slide 10. The smearing member 42 has a function of smearing the dropped specimen on the glass slide 10. Accordingly, dropping of a specimen onto a glass slide 10 and smearing of the dropped specimen can be performed by the common second processing section 40. Thus, compared with a case where dropping of a specimen and smearing of the specimen are respectively performed by separate processing sections, the transport route for the glass slide 10 can be simplified, and the apparatus can be downsized.

The dropping part 41 and the smearing member 42 are both disposed at positions above the glass slide 10 transported by the first slide transportation section 120. The smearing member 42 is a spreader glass, for example. The smearing member 42 can move in the up-down direction (the Z direction) and the Y direction by means of a movement mechanism not shown. In the configuration example shown in FIG. 9, since the holding member 121 of the first slide transportation section 120 can move in the X-Y directions, there is no need to provide a mechanism for causing the smearing member 42 to move in the X direction. The dropping part 41 is in fluid communication with the aspirator 220, and is implemented as a nozzle which discharges a specimen aspirated by the aspirator 220. The dropping part 41 can move in the X direction (the direction orthogonal to the drawing sheet of FIG. 9), for example, by means of a movement mechanism not shown.

In a state of the lowered position 430 (see FIG. 6), the first slide transportation section 120 moves in the X1 direction, to locate the holding member 121 from the first processing section 30 side to the processing position of the second processing section 40. As shown in FIG. 9, the first slide transportation section 120 raises the holding member 121 at the processing position of the second processing section 40.

Here, the second processing section 40 includes a positioning member 43. The positioning member 43 is disposed at a second process height position 432 for the second processing section 40, and comes into contact with the glass slide 10 on the holding member 121 raised by the first slide transportation section 120. Accordingly, even when there is variation in the thickness (the length in the Z direction) of the glass slide 10, the upper face of the glass slide 10 can be positioned at the constant second process height position 432.

The second process height position 432 at which the positioning member 43 and the glass slide 10 are in contact with each other is set to be a height position between the height position of the glass slide 10 at the first process height position 431, and the height position of the glass slide 10 at the lowered position 430. That is, the second process height position 432 for the smearing process is lower than the first process height position 431 for the printing process. Thus, when the positioning member 43 and the glass slide 10 come into contact with each other in the second processing section 40, the contact member 128*d* is not in contact with the restriction member 250.

In the raised state where the positioning has been realized at the second process height position 432 by the positioning member 43, the smearing process is performed by the second processing section 40 onto the glass slide 10 held by the holding member 121. It should be noted that slight difference in inclination between the positioning member 43 and the glass slide 10 is absorbed by deformation of the elastic members 128*c* supporting the holding member 121, and the close contact state between the positioning member 43 and the glass slide 10 is ensured. Accordingly, the parallelism between the end face of the smearing member 42 and the smear region 11 of glass slide 10 is ensured.

In the second processing section 40, the dropping part 41 is moved above the smear region 11 to drop the specimen to the smear region 11. Subsequently, in the second processing section 40, the end face of the smearing member 42 is brought into contact with a droplet of the specimen, and the smearing member 42 is moved in the longitudinal direction (the Y direction) of the glass slide 10, whereby the specimen is smeared on the smear region 11.

Figure 16:
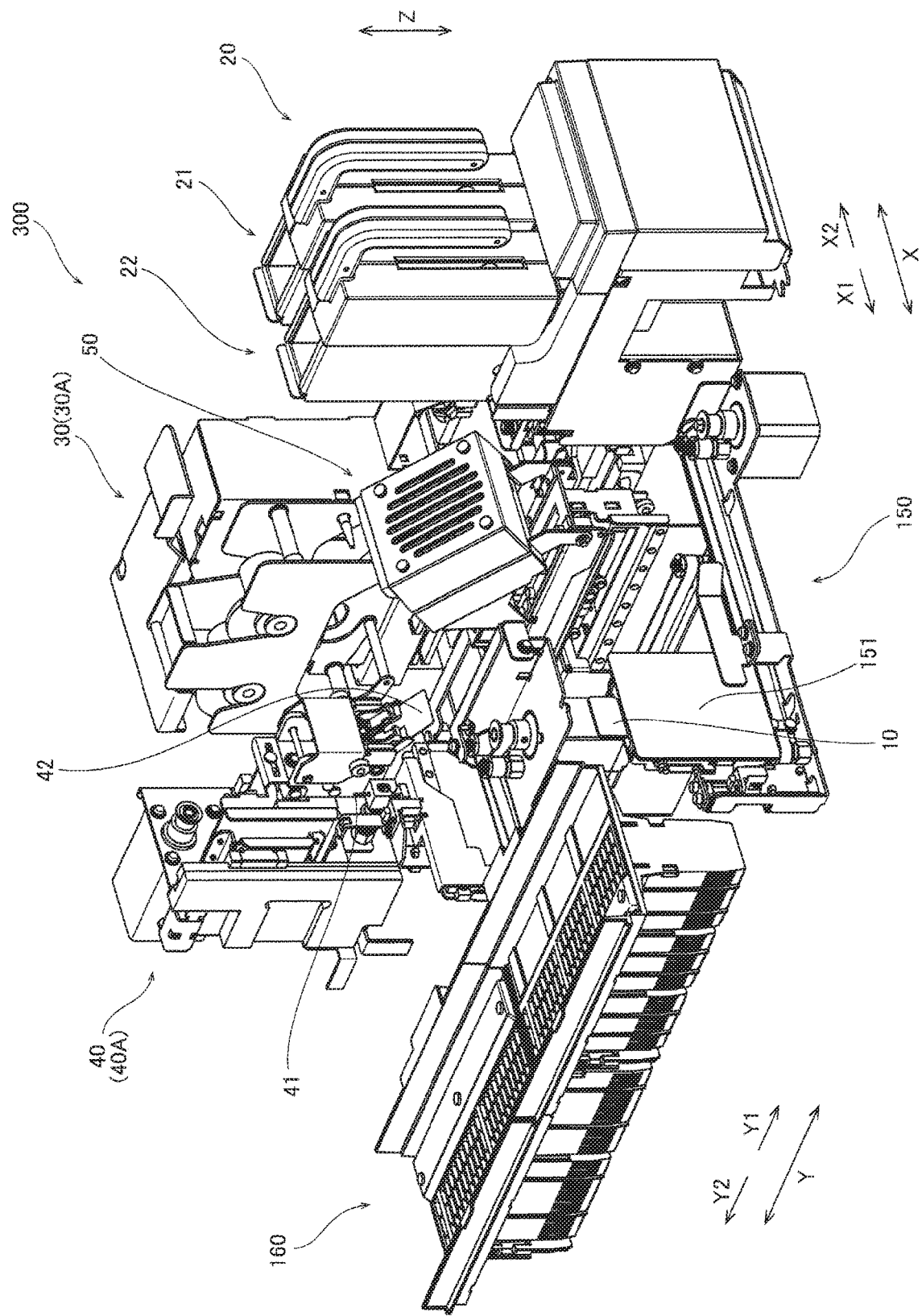
FIG. 16 is a perspective view showing the slide supplying section, the first processing section, the second processing section, and the first drying processing section.

As shown in FIG. 16, the first processing section 30 and the second processing section 40 disposed at the far side (the first direction side) of the apparatus body tend to have large height dimensions due to mechanisms and the like for causing the printing part 31, the dropping part 41, and the smearing member 42 to operate. Thus, if the first processing section 30 and the second processing section 40 are arranged alongside each other in the first direction, when the user performs work such as print ribbon replacement and spreader glass replacement, the processing section at the near side is in the way and the easiness of access to the processing section at the far side is decreased. In contrast to this, as shown in FIG. 16, when the first processing section 30 and the second processing section 40 are arranged alongside each other in the second direction which is the left-right direction, the user can perform more easily his/her work on the first processing section 30 and the second processing section 40.

<Positional Relationship Among Slide Supplying Section, First Processing Section, and Second Processing Section>

Figure 10:
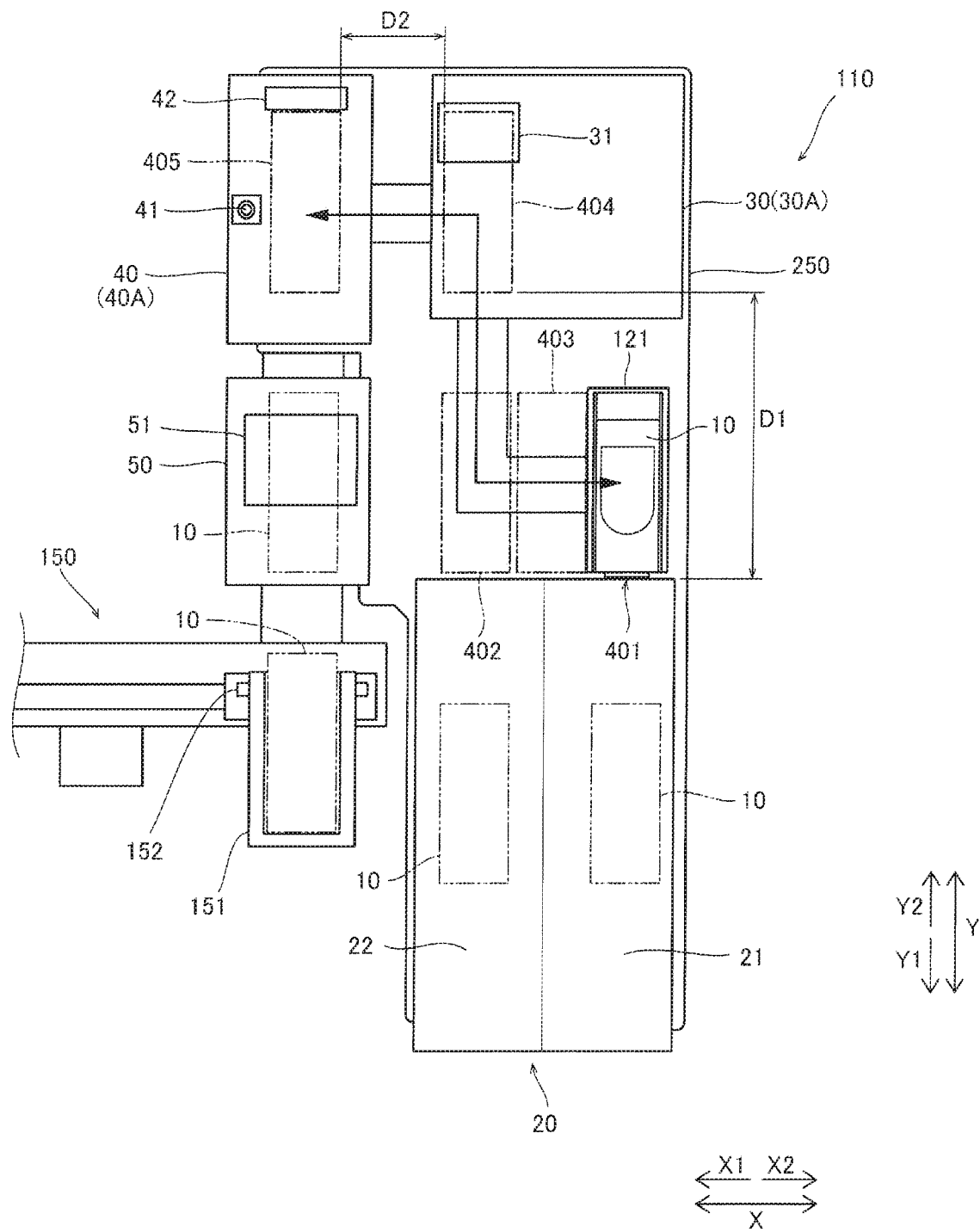
FIG. 10 is a plan view showing the positional relationship among the slide supplying section, the first processing section, the second processing section, and a first drying processing section.

As shown in FIG. 10, in the slide supplying section 20, the glass slide 10 is supplied at a supply position 401 for the first supplying section 21, or a supply position 402 for the second supplying section 22. The attached matter removing section 130 removes attached matters at a removal position 403 arranged in the X direction alongside the supply position 401 and the supply position 402. The first processing section 30 performs the printing process as the first process, at a processing position 404 located at the first direction (the Y2 direction) side of the supply position 402. The second processing section 40 performs the smearing process as the second process, at a processing position 405 located at the second direction (the X1 direction) side of the processing position 404 of the first processing section 30.

The supply position 402 and the processing position 404 are linearly arranged along the first direction (the Y2 direction). The first slide transportation section 120 causes the glass slide 10 to linearly move in the first direction (the Y2 direction) between the supply position 402 and the processing position 404. The processing position 404 and the processing position 405 are linearly arranged along the second direction (the X1 direction). The first slide transportation section 120 causes the glass slide 10 to linearly move in the second direction (the X1 direction) between the processing position 404 and the processing position 405. The processing position 405 and the first drying processing section 50 are linearly arranged along the third direction (the Y1 direction). The sending-out mechanism 140 causes the glass slide 10 to linearly move in the third direction (the Y1 direction) between the processing position 405 and the first drying processing section 50.

In the configuration example shown in FIG. 10, the slide supplying section 20 and the processing position 404 of the first processing section 30 are arranged in the first direction (the Y2 direction) so as to be separated from each other by a first distance D1. The processing position 404 of the first processing section 30 and the processing position 405 of the second processing section 40 are arranged in the second direction (the X1 direction) so as to be separated from each other by a second distance D2. The second distance D2 is smaller than the first distance D1. Accordingly, the transport distance of the glass slide 10 between the first processing section 30 and the second processing section 40 can be made smaller than the transport distance of the glass slide 10 between the slide supplying section 20 and the first processing section 30. As a result, the outer dimension in the left-right direction (the X direction) of the apparatus can be reduced. Thus, the installation space in the left-right direction, which is important in a use mode in which the smear sample preparing apparatus 300 and relating apparatuses are arranged alongside one another in the left-right direction, can be easily ensured. In the configuration example shown in FIG. 10, the second distance D2 is less than a half of the first distance D1.

<Configuration of First Drying Processing Section and Sending-Out Mechanism>

Figure 11:
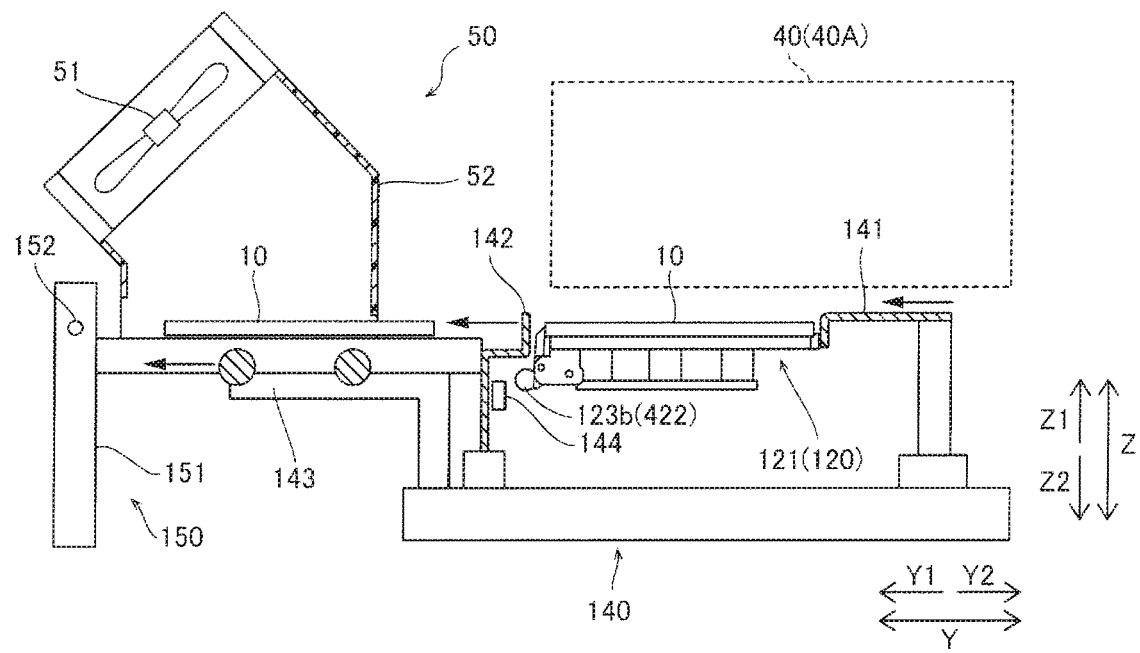
FIG. 11 is a schematic side view for describing the first drying processing section and a sending-out mechanism.

Next, with reference to FIG. 11, the first drying processing section 50, the sending-out mechanism 140, and the second slide transportation section 150 which is the third transportation section are described. In the configuration example shown in FIG. 11, the sending-out mechanism 140 is provided at a position where the second processing section 40 is disposed. The sending-out mechanism 140 can push out the glass slide 10 from the first slide transportation section 120 in the third direction (the Y1 direction), to deliver the glass slide 10 to the first drying processing section 50.

The sending-out mechanism 140 can move in the Y direction. The sending-out mechanism 140 includes a first pushing-out part 141. The first pushing-out part 141 can come into contact with the end face at the Y2 direction side of the glass slide 10, thereby to send out the glass slide 10 in the Y1 direction from the first slide transportation section 120 located at the second processing section 40, to the first drying processing section 50.

The first drying processing section 50 includes an air blowing fan 51 disposed at a position above the glass slide 10, and a duct member 52. The air blowing fan 51 blows air obliquely downwardly to the Y2 direction side, toward the glass slide 10. The duct member 52 is disposed at the outlet side of the air blowing fan 51, and turns the air of the air blowing fan 51 downwardly (Z2 direction) to be guided to the glass slide 10. Although not shown, the duct member 52 is provided with an air outlet hole (not shown) at the X direction side, and has a function of preventing the air of the air blowing fan 51 from reaching the second processing section 40 at the Y2 direction side.

In the configuration example shown in FIG. 11, the sending-out mechanism 140 can push out the glass slide 10 from the first drying processing section 50 in the third direction (the Y1 direction), to deliver the glass slide 10 to the second slide transportation section 150. The sending-out mechanism 140 includes a second pushing-out part 142, a third pushing-out part 143, and a touching member 144. The second pushing-out part 142 can send out the glass slide 10 in the first drying processing section 50 to the second slide transportation section 150. The second pushing-out part 142 moves in the Y1 direction in a raised state, thereby to press the glass slide 10 in the first drying processing section 50 toward the second slide transportation section 150. Meanwhile, the second pushing-out part 142 moves in the Y2 direction in a lowered state, thereby to return to the original position thereof while avoiding the glass slide 10 on the first drying processing section 50.

Figure 12:
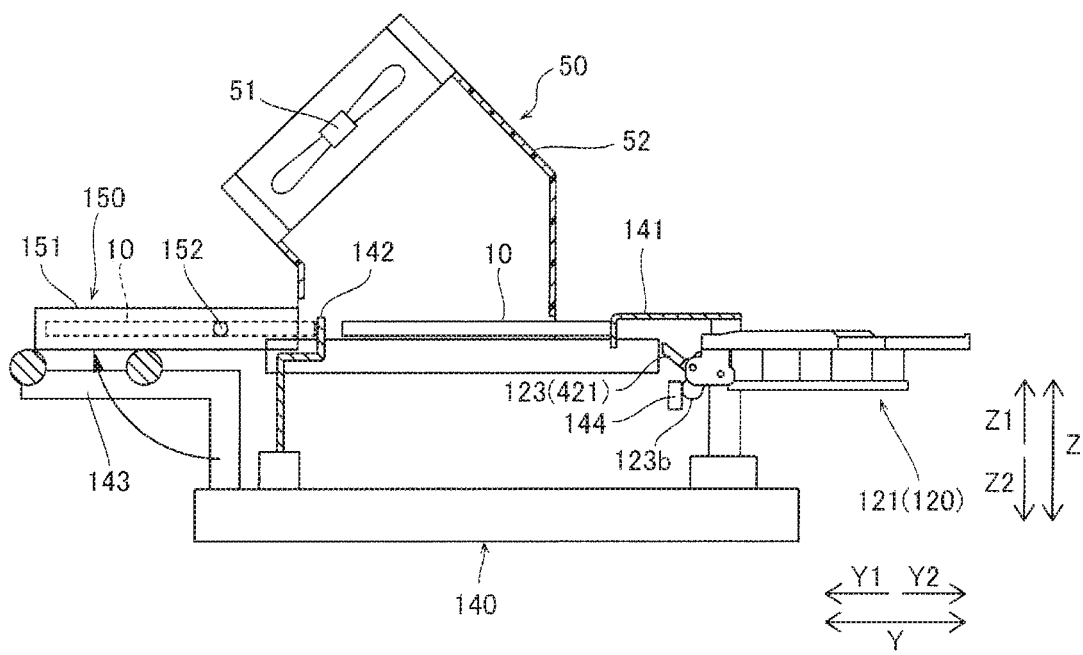
FIG. 12 is a side view for describing delivery of a glass slide from the first drying processing section to a second slide transportation section.

The third pushing-out part 143 can push out the accommodation part 151 of the second slide transportation section 150 in the Y1 direction, to cause the second slide transportation section 150 to rotate. Specifically, the accommodation part 151 of the second slide transportation section 150 can rotate about a rotation shaft 152 extending in the X direction. When the glass slide 10 is to send out from the first drying processing section 50 to the second slide transportation section 150, the accommodation part 151 is pushed by the third pushing-out part 143, to be rotated to have an attitude in which the accommodation part 151 extends in the horizontal direction. As shown in FIG. 12, the accommodation part 151, in the state of the horizontal attitude, receives the glass slide 10 pushed out in the third direction (the Y1 direction) by the second pushing-out part 142. After having received the glass slide 10, the accommodation part 151 is rotated to have an attitude in which the accommodation part 151 extends in the perpendicular direction (see FIG. 11). That is, the second slide transportation section 150 comes to have an attitude in which the second slide transportation section 150 extends in the perpendicular direction due to the gravity, as a result of the third pushing-out part 143 receding in the Y2 direction. Thus, the glass slide 10 in the horizontal attitude can be caused to stand in the perpendicular attitude.

The first pushing-out part 141, the second pushing-out part 142, and the third pushing-out part 143 are moved in the Y direction in conjunction with one another. That is, the first pushing-out part 141, the second pushing-out part 142, and the third pushing-out part 143 are moved by a common drive part (not shown) of the sending-out mechanism 140.

The touching member 144 comes into contact with the grip part 123 of the first slide transportation section 120, thereby being able to cause the grip part 123 to move to the open position 421.

<Slide Setting Section>

Figure 13:
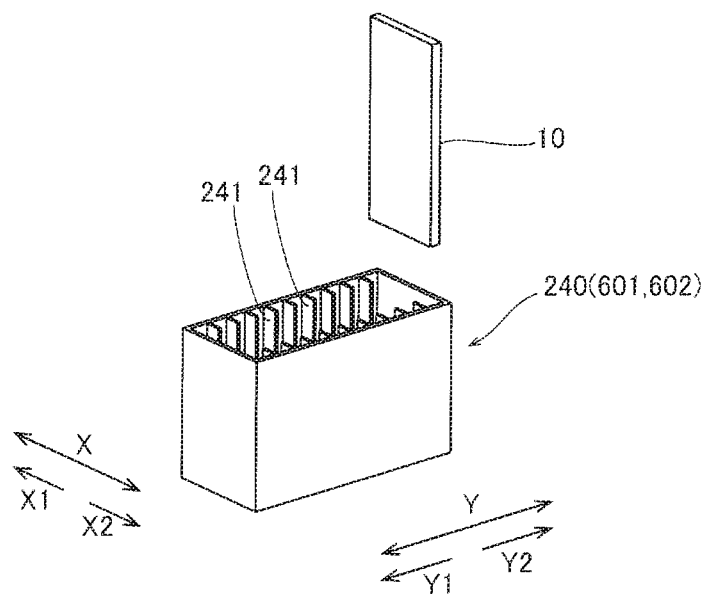
FIG. 13 is a perspective view showing a configuration example of a slide storage container set in a slide setting section.

FIG. 13 shows a common slide storage container 240 as one example of the first storage container 601 and the second storage container 602. In the slide setting section 170, the slide storage container 240 shown in FIG. 13 is set, for example. The slide storage container 240 can store a plurality of the glass slides 10. From the inner face at each of both sides in the short direction of the slide storage container 240, plate-like partition plates 241 protrude toward the inner side in the short direction. The partition plates 241 are arranged at equal intervals in the longitudinal direction. In each space between these partition plates 241, one glass slide 10 is inserted. Both end portions in the left-right direction of the inserted glass slide 10 are supported by the partition plates 241, whereby the glass slide 10 is held in an attitude in which the glass slide 10 extends in the perpendicular direction. Accordingly, the slide storage container 240 can store the plurality of the glass slides 10 arranged in the Y direction.

(Staining Processing Section, Third Slide Transportation Section, and Second Drying Processing Section)

Figure 14:
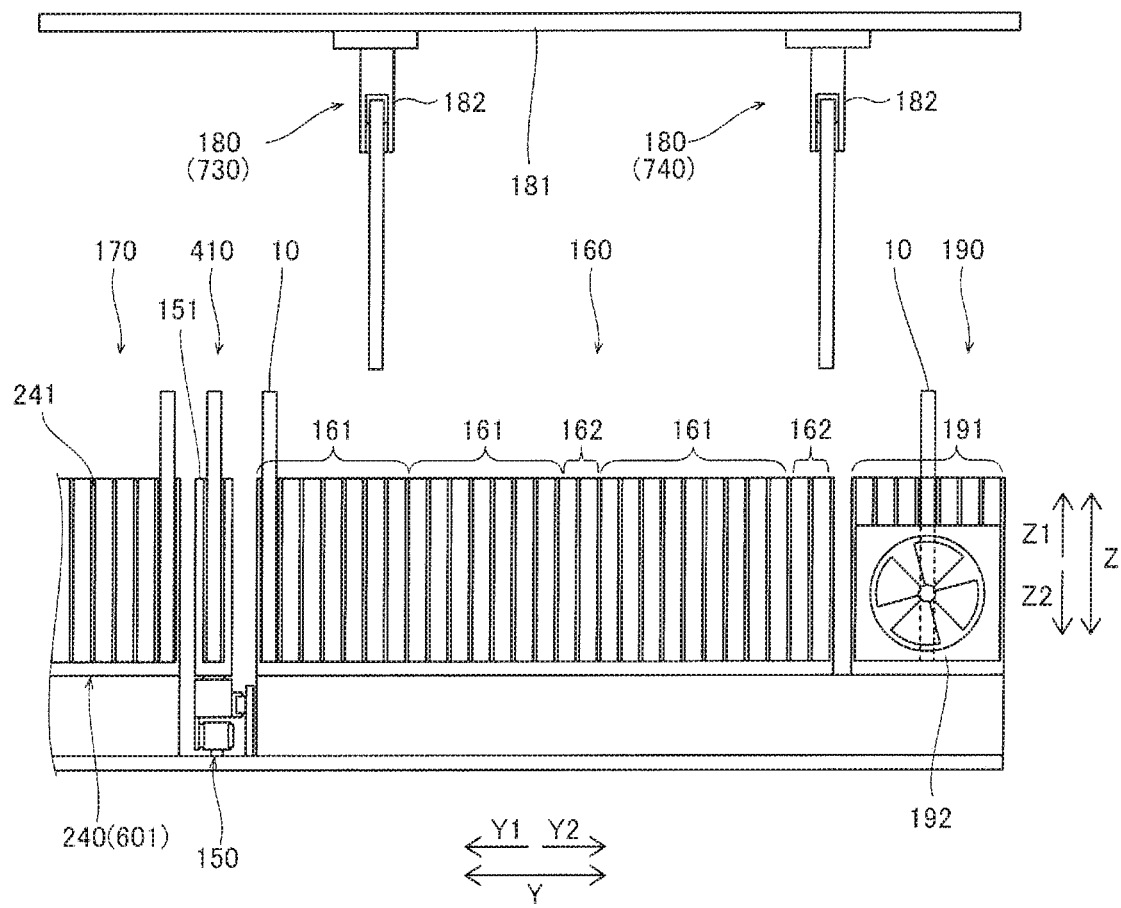
FIG. 14 is a schematic side view for describing the slide setting section, a staining processing section, a second drying processing section, and a third slide transportation section.

In the configuration example shown in FIG. 14, the staining processing section 160 includes a staining chamber 161 and a washing chamber 162. Each of the staining chamber 161 and the washing chamber 162 has a container shape being open at the upper side thereof, and can store a liquid therein. In the staining chamber 161 and the washing chamber 162, the glass slides 10 each in a standing state can be set, arranged in the Y direction. The staining chamber 161 stores a predetermined staining liquid, and the washing chamber 162 stores a predetermined washing liquid. FIG. 14 shows three staining chambers 161 and two washing chambers 162 for convenience, but the staining chamber 161 and the washing chamber 162 are provided in numbers according to the number of staining process steps and the number of washing process steps, respectively. The staining chambers 161 and the washing chambers 162 are arranged alongside one another in the Y direction in accordance with the order of the process steps. Each glass slide 10 is sequentially transported to the chambers from the Y1 direction side toward the Y2 direction side, and is processed by being immersed for a predetermined set time period in the staining liquid or the washing liquid stored in each chamber.

The second drying processing section 190 includes a drying chamber 191, and an air blowing fan 192 provided to the drying chamber 191. The drying chamber 191 has the upper side thereof open, and can have the glass slide 10 inserted therein. In the drying chamber 191, the glass slides 10 each in a standing state can be set, arranged in the Y direction. The air blowing fan 192 blows air to each glass slide 10 held in the drying chamber 191. Accordingly, the second drying processing section 190 dries the glass slides 10 having been subjected to the staining process.

The third slide transportation section 180 includes a movement mechanism 181 provided in an upper portion of the apparatus, and a hand 182 provided to the movement mechanism 181. The movement mechanism 181 can cause the hand 182 to move in the X direction and the Y direction which are horizontal directions. The hand 182 can move in the Z direction and can grip one glass slide 10. As to the hand 182, a configuration example is shown in which the glass slide 10 is sandwiched and gripped in the thickness direction by means of a pair of gripping plates. The hand 182 may be configured to sandwich the glass slide 10 in the left-right direction.

In the configuration example shown in FIG. 14, two third slide transportation sections 180 are provided. That is, the third slide transportation sections 180 include a first transportation section 730 and a second transportation section 740. The third slide transportation section 180 at the Y1 direction side can move to positions above the slide setting section 170, the taking-out position 410, and the staining processing section 160, and can take in and out the glass slide 10. The third slide transportation section 180 at the Y2 direction side can move to positions above the staining processing section 160, the second drying processing section 190, and the storing position 412 (see FIG. 2) of the slide storage section 200, and can take in and out the glass slide 10. The glass slide 10 is transported midway of the staining processing section 160 by the third slide transportation section 180 at the Y1 direction side, and then, is transported to the second drying processing section 190 or the slide storage section 200 by the third slide transportation section 180 at the Y2 direction side. One, or three or more of the third slide transportation section 180 may be provided.

(Smear Sample Preparing Operation Performed by Smear Sample Preparing Apparatus)

An example of smear sample preparing operation performed by the smear sample preparing apparatus 300 is described with reference to FIG. 15. Control of the smear sample preparing apparatus 300 is performed by the controller 230.

Figure 15:
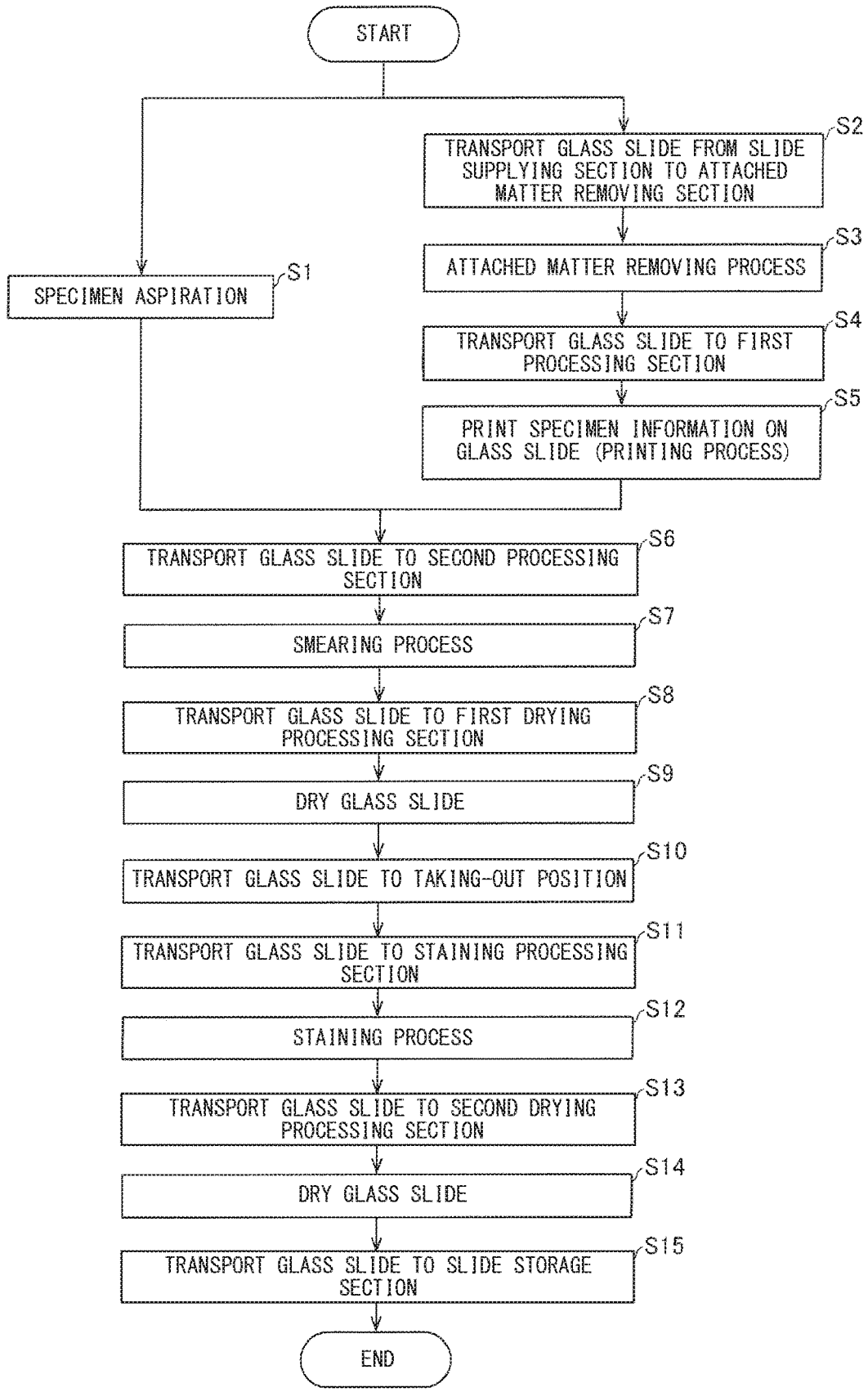
FIG. 15 is a flow chart showing a smear sample preparing process.

First, in step S1 shown in FIG. 15, a specimen aspiration process is performed. A specimen is aspirated by the aspirator 220, from a specimen container 211 transported by the specimen transportation section 210 to an aspiration position. In step S2, which is performed in parallel with the process in step S1, a glass slide 10 is transported to the attached matter removing section 130. Specifically, the glass slide 10 is supplied from the slide supplying section 20 to the first slide transportation section 120. Then, the glass slide 10 held by the first slide transportation section 120 is transported to the attached matter removing section 130. In step S3, an attached matter removing process for the glass slide 10 held by the first slide transportation section 120 is performed by the attached matter removing section 130.

In step S4, the glass slide 10 is transported to the first processing section 30 by the first slide transportation section 120. At the processing position 404 (see FIG. 10), the first slide transportation section 120 locates the glass slide 10 at the first process height position 431 (see FIG. 8). In step S5, the printing process is performed by the first processing section 30, on the glass slide 10 held by the first slide transportation section 120.

In step S6, the glass slide 10 is transported to the second processing section 40 by the first slide transportation section 120. At the processing position 405 (see FIG. 10), the first slide transportation section 120 locates the glass slide 10 at the second process height position 432 (see FIG. 9). In step S7, the smearing process is performed by the second processing section 40, on the glass slide 10 held by the first slide transportation section 120.

In step S8, the glass slide 10 is transported to the first drying processing section 50. Specifically, the glass slide 10 is delivered by the sending-out mechanism 140, from the first slide transportation section 120 to the first drying processing section 50. In step S9, the drying process is performed by the first drying processing section 50, on the specimen smeared on the glass slide 10.

In step S10, the glass slide 10 is transported to the taking-out position 410 (see FIG. 2) by the second slide transportation section 150. Specifically, the glass slide 10 is delivered by the sending-out mechanism 140, from the first drying processing section 50 to the accommodation part 151 of the second slide transportation section 150. The second slide transportation section 150 transports the glass slide 10 set in the accommodation part 151, to the taking-out position 410.

In step S11, the glass slide 10 is transported to the staining processing section 160. Specifically, the glass slide 10 is taken out from the second slide transportation section 150 at the taking-out position 410 to be transported to the staining processing section 160, by the third slide transportation section 180. In step S12, the staining process is performed by the staining processing section 160, on the specimen smeared on the glass slide 10. The glass slide 10 is sequentially transported to the staining chambers and the washing chambers in accordance with the order of the process steps. During this procedure, the glass slide 10 moves in the staining processing section 160, from the Y1 direction side to the Y2 direction side.

In step S13, the glass slide 10 is transported to the second drying processing section 190. Specifically, the glass slide 10 is delivered by the third slide transportation section 180, from the staining processing section 160 to the second drying processing section 190. In step S14, the drying process is performed by the second drying processing section 190, on the specimen smeared and stained on the glass slide 10. Accordingly, a smear sample is prepared on the glass slide 10.

In step S15, the glass slide 10 is transported to the slide storage section 200. Specifically, the glass slide 10 is delivered by the third slide transportation section 180, from the second drying processing section 190 to the slide storage container 240 disposed at the storing position 412 in the slide storage section 200. Then, the slide storage container 240 is transported to the collecting position 413. At the collecting position 413, the glass slide 10 having the smear sample prepared thereon is stored in the slide storage section 200. Then, the smear sample preparing process is ended.

It should be noted that, in the case of the smear mode, when the glass slide 10 transported to the taking-out position 410 in step S10 is transported by the third slide transportation section 180 to the slide setting section 170, the process ends. The user can collect, from the slide setting section 170, the unstained glass slide 10 having been subjected to the printing process and the smearing process.

In the case of the stain mode, the processes of step S11 and the steps thereafter are performed on a smeared glass slide 10 set in the slide setting section 170 by the user. In this case, the glass slide 10 is transported by the third slide transportation section 180, from the slide setting section 170 to the staining processing section 160.

Second Embodiment

In the following, a second embodiment is described.

Overview of Second Embodiment

Japanese Laid-Open Patent Publication No. 2006-78296 discloses a sample preparing apparatus including a smearing part, a printing part, a staining part, and a storing part. This sample preparing apparatus can operate in a plurality of operation modes. In a "sampler mode" or a "smear-stain mode", the sample preparing apparatus sequentially transfers a glass slide to the smearing part, the printing part, the staining part, and the storing part. A specimen is smeared on the glass slide in the smearing part, specimen identification information and the like are printed on the glass slide in the printing part, the specimen on the glass slide is stained in the staining part, and the prepared smear sample is stored in the storing part. The sample preparing apparatus can also operate in a "smear mode" in which smearing and printing are performed but staining is not performed, a "stain mode" in which staining is performed but smearing and printing are not performed, or a "print mode" in which printing is performed but smearing and staining are not performed.

In the case of the sample preparing apparatus disclosed in Japanese Laid-Open Patent Publication No. 2006-78296 described above, in all the operation modes, the glass slide is transferred in the same route which passes through the smearing part, the printing part, the staining part, and the storing part. Thus, for example, when the staining process is being performed on another glass slide in the staining part, even if a glass slide need not be stained, the glass slide cannot be transferred until the staining process ends. Thus, it takes a long time until the glass slide is transferred to the storing part and the user becomes able to take out the glass slide.

In the second embodiment, a configuration example of the smear sample preparing apparatus 300 is described in which the user can promptly take out, from the apparatus, a glass slide that need not be stained.

As an apparatus configuration of the smear sample preparing apparatus 300 in the second embodiment, a configuration similar to that in the configuration example shown in FIG. 2 can be employed. In the second embodiment, the first processing section 30 which performs the printing process is referred to as a printing processing section 30A. In the second embodiment, the second processing section 40 which performs the smearing process is referred to as a smearing processing section 40A. In the second embodiment, detailed configuration examples of the specimen transportation section 210, the aspirator 220, the staining processing section 160, the third slide transportation section 180, and the slide setting section 170 are described. In addition, in the second embodiment, various types of processing operation examples of the smear sample preparing apparatus 300 are described.

(Detailed Configuration of Specimen Transportation Section and Aspirator)

Figure 17:
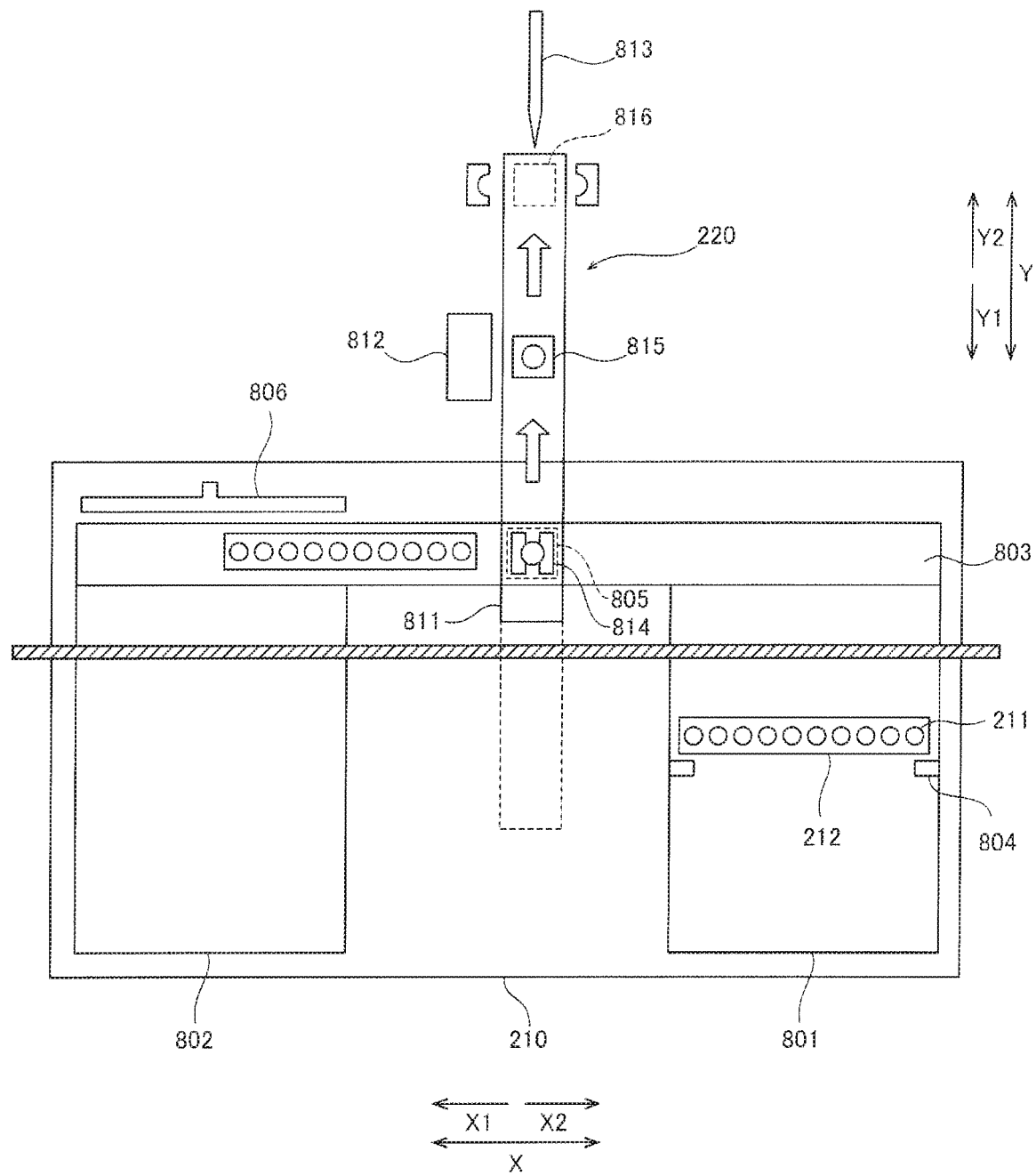
FIG. 17 is a schematic diagram showing configurations of a specimen transportation section and an aspirator.

The configurations of the specimen transportation section 210 and the aspirator 220 are described with reference to FIG. 17. The specimen transportation section 210 includes: a first holder 801 and a second holder 802 each capable of holding a rack 212; and a transport line 803 for transporting the rack 212. The first holder 801 and the second holder 802 are arranged in the horizontal direction, and the first holder 801 is disposed at the X2 direction side, and the second holder 802 is disposed at the X1 direction side. The transport line 803 is disposed at the Y2 direction side of the first holder 801 and the second holder 802. The transport line 803 extends in the X direction, and connects the first holder 801 and the second holder 802.

The first holder 801 is a region in a recessed shape and for holding a rack placed by the user. At each of both lateral faces of the first holder 801, a claw part 804 is provided so as to be able to protrude. By moving in the Y2 direction in a protruding state, the claw parts 804 push the rack 212 in the Y2 direction to send out the rack 212 to the transport line 803.

The transport line 803 is a belt conveyor and transports the rack 212 in the X1 direction.

The aspirator 220 is provided at the upper side of the transport line 803. The aspirator 220 includes a specimen container setting part 811, a bar code reader 812, and an aspiration tube 813. The specimen container setting part 811 includes a grip part 814 which grips the specimen container 211. The grip part 814 moves downwardly, grips the specimen container 211 at a supply position 805 on the transport line 803, moves upwardly, and takes out the specimen container 211 from the rack 212. By swinging the specimen container 211 gripped by the grip part 814, the specimen container setting part 811 agitates the specimen in the specimen container 211.

The specimen container setting part 811 can move in the Y direction. The specimen container setting part 811 moves in the Y2 direction in a state where the specimen container 211 is gripped by the grip part 814, whereby the specimen container setting part 811 transfers the specimen container 211 into the smear sample preparing apparatus 300.

The specimen container setting part 811 transfers the specimen container 211 to a reading position 815 inside the smear sample preparing apparatus 300. A bar code label having a bar code of a specimen ID printed thereon is attached to the specimen container 211. The bar code reader 812 reads the specimen ID from the bar code of the specimen container 211 located at the reading position 815.

The specimen container setting part 811 transfers the specimen container 211 further in the Y2 direction, to locate the specimen container 211 at an aspiration position 816. The aspiration tube 813 in a tubular shape and having a pointed end penetrates the cap of the specimen container 211, and aspirates the specimen.

After the specimen has been aspirated, the specimen container setting part 811 moves in the Y1 direction and the grip part 814 moves downwardly, whereby the specimen container 211 is returned to the original position thereof in the rack 212.

The second holder 802 is a region in a recessed shape and for holding a rack for which the specimen aspiration has been performed. A rack transfer part 806 movable in the Y1 direction is provided at the Y2 direction side of the transport line 803. When the transport line 803 has transported the rack 212 to the end in the X1 direction, the rack transfer part 806 moves in the Y1 direction. Accordingly, the rack 212 is pushed by the rack transfer part 806 to be moved in the Y1 direction and reaches the second holder 802.

The specimen container setting part 811 can protrude, in the Y1 direction, out of the housing of the smear sample preparing apparatus 300. The user can set a specimen container 211 in the specimen container setting part 811 sent out in the Y1 direction. The specimen container setting part 811 having the specimen container 211 set therein moves in the Y2 direction, whereby the specimen container 211 is transferred into the smear sample preparing apparatus 300. After the specimen has been aspirated, the specimen container setting part 811 advances to the outside of the smear sample preparing apparatus 300 again. Accordingly, the specimen container 211 is returned to the user.

(Detailed Configuration of Staining Processing Section and Third Slide Transportation Section)

Figure 18:
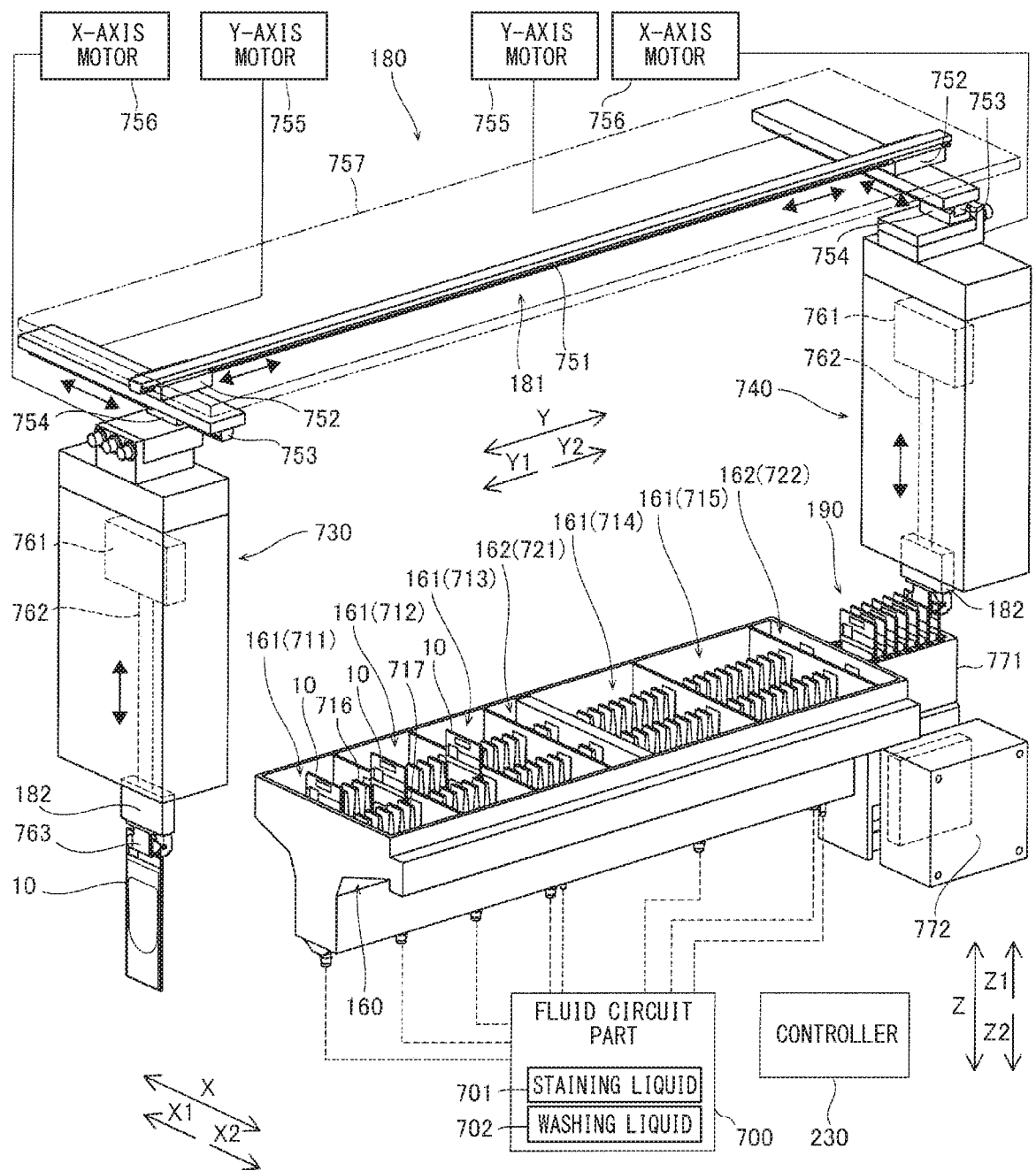
FIG. 18 is a perspective view showing configurations of the staining processing section and the third slide transportation section.

The configurations of the staining processing section 160 and the third slide transportation section 180 are described with reference to FIG. 18. In the description below, the up-down direction is referred to as the Z direction.

The staining processing section 160 includes the staining chambers 161 and the washing chambers 162. The smear sample preparing apparatus 300 includes a fluid circuit part 700 for supplying and discharging a staining liquid 701 and a washing liquid 702 to and from each staining chamber 161 and each washing chamber 162.

The staining chamber 161 and the washing chamber 162 each have a container shape being open at the upper side thereof, and can store therein the staining liquid 701 and the washing liquid 702, respectively. In each of the staining chamber 161 and the washing chamber 162, the glass slide 10 of which width direction is the X direction and of which thickness direction is the Y direction can be inserted.

The staining chambers 161 preferably include a first staining chamber 711 and a second staining chamber 712. FIG. 18 shows an example in which the staining chambers include five staining chambers 161, i.e., the first staining chamber 711 to fifth staining chamber 715.

The washing chambers 162 include a first washing chamber 721 and a second washing chamber 722.

In the staining processing section 160, the first staining chamber 711, the second staining chamber 712, the third staining chamber 713, the first washing chamber 721, the fourth staining chamber 714, the fifth staining chamber 715, and the second washing chamber 722 are sequentially arranged in the Y2 direction.

Inside the staining chamber 161, a first holder 716 and a second holder 717 each having a plate shape are provided so as to be separated from each other in the X direction. In addition, a plurality of the first holders 716 and a plurality of the second holders 717 are arranged in the Y direction at equal intervals. One glass slide 10 is inserted in a space between a first holder 716 and a second holder 717, and another first holder 716 and another second holder 717 adjacent thereto. Both end portions in the width direction of the inserted glass slide 10 are supported by the first holders 716 and the second holders 717, whereby the standing state of the glass slide 10 is maintained. Also in the washing chamber 162, the glass slide 10 can be held in a standing state.

The glass slide 10 is sequentially transported to the chambers, starting from the first staining chamber 711, and is processed by being immersed for a predetermined set time period in the staining liquid 701 or the washing liquid 702 stored in each chamber.

The third slide transportation section 180 is disposed above (the Z1 direction) the staining processing section 160 and the slide setting section 170. The third slide transportation section 180 preferably includes the first transportation section 730 and the second transportation section 740. By providing the second transportation section 740 separately from the first transportation section 730, transportation of the glass slide 10 from the taking-out position 410 to the staining processing section 160, and transportation of the glass slide from the staining processing section 160 to the slide storage section 200 can be performed separately, which improves the transportation efficiency. Each of the first transportation section 730 and the second transportation section 740 can move in the horizontal direction (i.e., the X direction and the Y direction) by means of the movement mechanism 181.

The movement mechanism 181 includes: a Y-axis rail 751 and a Y-axis slider 752 which extend in the Y direction; an X-axis rail 753 and an X-axis slider 754 which extend in the X direction; a Y-axis motor 755; and an X-axis motor 756.

As each of the Y-axis motor 755 and the X-axis motor 756, a stepping motor or a servo motor can be employed, for example.

The Y-axis rail 751 is fixed to the lower face of a support member 757. The support member 757 is a ceiling part, a support beam member, or the like of the housing of the smear sample preparing apparatus 300. The Y-axis slider 752 is mounted at the lower face side (the Z2 direction side) of the Y-axis rail 751, and can move along the Y-axis rail 751. The Y-axis motor 755 causes the Y-axis slider 752 to move in the Y direction through a transmission mechanism not shown. As the transmission mechanism, a belt-pulley mechanism, a rack-pinion mechanism, or the like can be employed, for example.

The X-axis rail 753 is fixed to the lower face of the Y-axis slider 752. The X-axis slider 754 is mounted at the lower face side (the Z2 direction side) of the X-axis rail 753 and can move along the X-axis rail 753. The X-axis motor 756 causes the X-axis slider 754 to move in the X direction through a transmission mechanism not shown.

The Y-axis slider 752, the X-axis rail 753, the X-axis slider 754, the X-axis motor 756, and the Y-axis motor 755 are each provided in a pair. The first transportation section 730 is mounted at the lower face side of one of the X-axis sliders 754, and the second transportation section 740 is mounted at the lower face side of the other of the X-axis sliders 754. Thus, the first transportation section 730 and the second transportation section 740 can move in the X direction independently of each other along the individual X-axis rails 753. In addition, the first transportation section 730 and the second transportation section 740 can move in the Y direction independently of each other along the common Y-axis rail 751.

The first transportation section 730 and the second transportation section 740 have a common configuration with each other. Each of the first transportation section 730 and the second transportation section 740 includes the hand 182, a Z-axis motor 761 for raising and lowering the hand 182, and a transmission mechanism 762. The Z-axis motor 761 causes the hand 182 to be raised and lowered through the transmission mechanism 762. As the transmission mechanism 762, a belt-pulley mechanism, a rack-pinion mechanism, or the like can be employed, for example.

The hand 182 can grip one glass slide 10. FIG. 18 shows a configuration example in which the glass slide 10 is sandwiched and gripped in the thickness direction by a pair of gripping plates 763. The pair of gripping plates 763 sandwich the glass slide 10 by coming into contact with the surface and the back surface of the glass slide 10. The pair of gripping plates 763 can move relative to each other in the thickness direction (the Y direction) of the glass slide 10. Movement of the gripping plates 763 can be realized by use of an actuator such as an air cylinder, a motor, or a solenoid, for example. The hand 182 may be configured to sandwich the glass slide 10 in the width direction.

The first transportation section 730 can move to positions above the first staining chamber 711, the second staining chamber 712, the third staining chamber 713, and the first washing chamber 721. Thus, the first transportation section 730 can insert and pull out the glass slides 10 one by one into and out of each of the first staining chamber 711, the second staining chamber 712, the third staining chamber 713, and the first washing chamber 721.

The first transportation section 730 can also move to positions above the taking-out position 410, and two first storage containers 601 in the slide setting section 170. Thus, the first transportation section 730 can pull out one glass slide 10 from the taking-out position 410, and also can insert and pull out the glass slides 10 one by one into and out of each of the two first storage containers 601 in the slide setting section 170.

The second transportation section 740 can move to positions above the first washing chamber 721, the fourth staining chamber 714, the fifth staining chamber 715, and the second washing chamber 722. Thus, the second transportation section 740 can insert and pull out the glass slides 10 one by one into and out of each of the first washing chamber 721, the fourth staining chamber 714, the fifth staining chamber 715, and the second washing chamber 722.

The second transportation section 740 can also move to positions above the second drying processing section 190, and the storing position 412 of the slide storage section 200. Thus, the second transportation section 740 can insert and pull out the glass slides 10 one by one into and out of the second drying processing section 190, and also can insert the glass slides 10 one by one into the second storage container 602 at the storing position 412 of the slide storage section 200.

The first transportation section 730 and the second transportation section 740 can respectively transport the glass slides 10 in parallel with each other. The operation range of the first transportation section 730 and the operation range of the second transportation section 740 overlap each other at the first washing chamber 721, and the glass slide 10 is delivered at the first washing chamber 721. The delivery position may be a position other than the first washing chamber 721.

The second drying processing section 190 includes an accommodation part 771 and an air-blowing part 772. The accommodation part 771 is a container being open at the upper side thereof, and can accommodate a plurality of the glass slides 10 each in a standing state. The air-blowing part 772 can blow air into the accommodation part 771. By the air-blowing part 772 blowing air, the stained glass slides 10 accommodated in the accommodation part 771 are dried.

(Detailed Configuration of Slide Setting Section)

Figure 19:
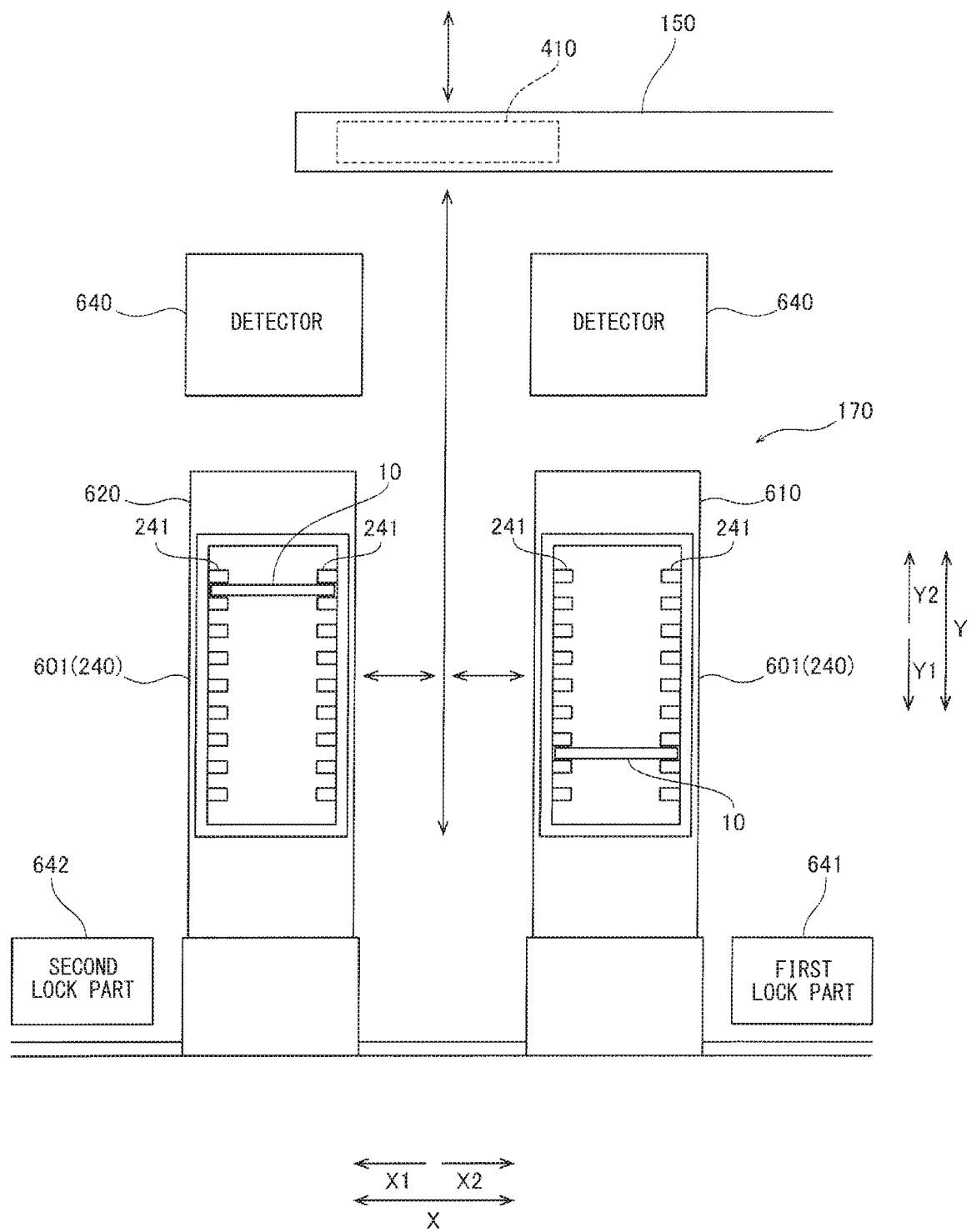
FIG. 19 is a plan view showing a configuration of the slide setting section.

The configuration of the slide setting section 170 is described with reference to FIG. 19. The slide setting section 170 includes a first setting section 610 and a second setting section 620. The first setting section 610 and the second setting section 620 are arranged alongside each other in the X direction. The first setting section 610 is disposed at the X2 direction side, and the second setting section 620 is disposed at the X1 direction side. The first setting section 610 and the second setting section 620 have a common configuration with each other.

Figure 20:
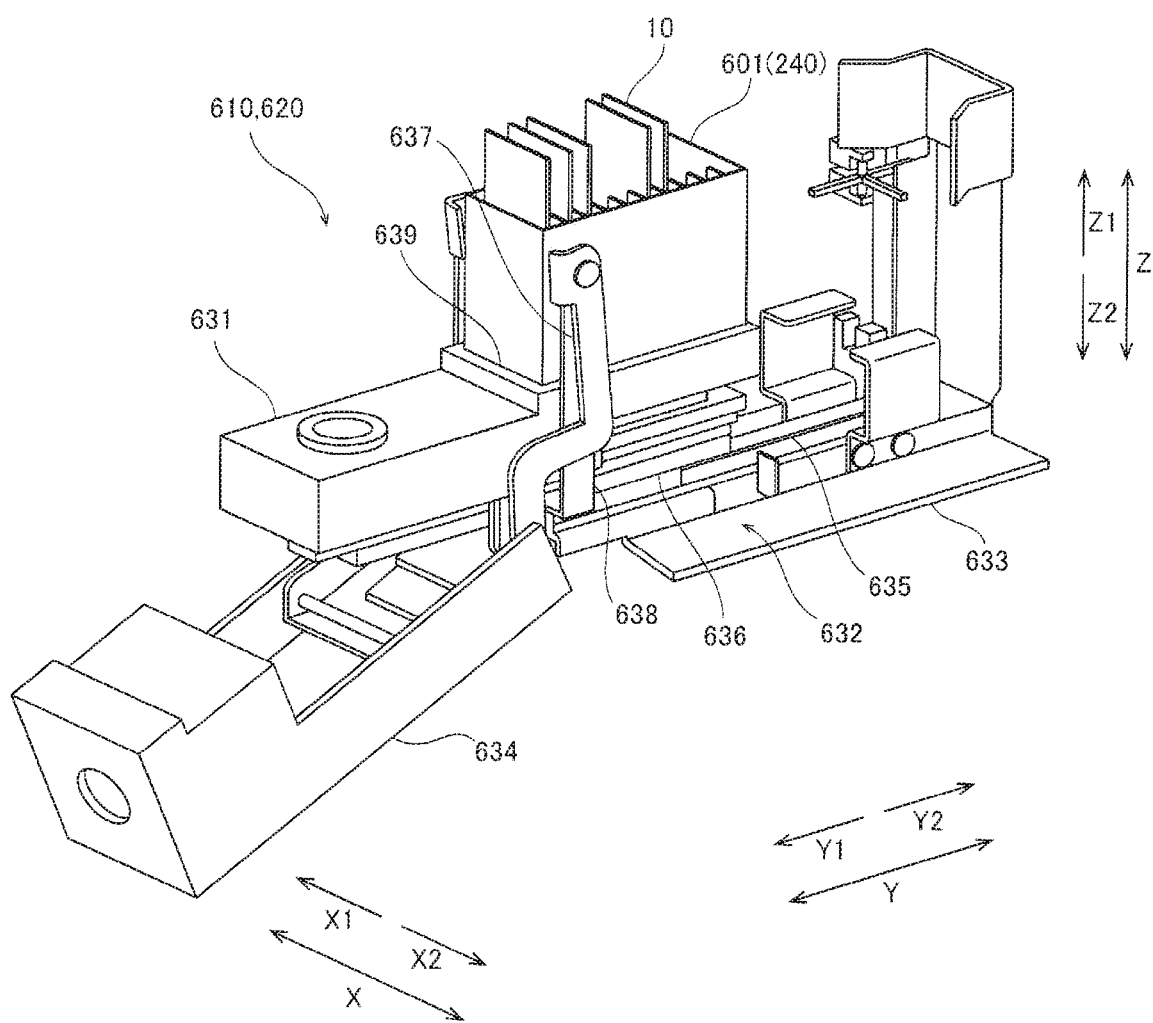
FIG. 20 is a perspective view showing configurations of a first setting section and a second setting section.

Each of the first setting section 610 and the second setting section 620 can have one first storage container 601 set therein. As shown in FIG. 20, each of the first setting section 610 and the second setting section 620 includes: a setting member 631 for setting the first storage container 601; a slide mechanism 632; a base member 633; and a cover 634.

The slide mechanism 632 includes a Y-axis rail 635 extending in the Y direction, and a Y-axis slider 636. The Y-axis rail 635 is fixed to the base member 633. The base member 633 is fixed to the floor face of the housing of the smear sample preparing apparatus 300. The Y-axis slider 636 is mounted at the upper face side (the Z1 direction side) of the Y-axis rail 635 and can move along the Y-axis rail 635.

The setting member 631 is mounted at the upper face side of the Y-axis slider 636. Thus, the setting member 631 can move in the Y direction.

The cover 634 is disposed at the Y1 direction side of the setting member 631. The cover 634 is disposed at an opening provided in the housing of the smear sample preparing apparatus 300. The cover 634 is mounted to an end portion in the Y1 direction of the base member 633, so as to be rotatable about a rotation shaft extending in the X direction. By the cover 634 being rotated, the opening provided in the housing of the smear sample preparing apparatus 300 can be closed or opened. That is, the cover 634 can be opened and closed by being rotated. FIG. 20 shows a state in which the cover 634 is open.

The cover 634 and the setting member 631 are coupled to each other by means of a pair links 637. One of the links 637 is provided at the X1 direction side of the cover 634 and the setting member 631, and the other of the links 637 is provided at the X2 direction side of the cover 634 and the setting member 631. One end of each link 637 is mounted to the cover 634, so as to be rotatable about a rotation shaft extending in the X direction. At each of lower end portions at both sides of the setting member 631, a bar member 638 extending in the Z1 direction is provided. The other end of each link 637 is mounted to a Z1 direction side (upper side) portion of a corresponding bar member 638, so as to be rotatable about a rotation shaft extending in the X direction. Thus, when the closed cover 634 is opened, the setting member 631 slides in the Y1 direction, associated therewith. When the open cover 634 is closed, the setting member 631 slides in the Y2 direction, associated therewith.

The first storage container 601 is a rectangular parallelepiped box being open at the upper side thereof. At the upper face side of the setting member 631, a recessed portion 639 for attaching/detaching the first storage container 601 is provided. The user attaches/detaches first storage container 601 to/from the recessed portion 639, in a state where the cover 634 is open and the setting member 631 is moved in the Y1 direction. In a state where the cover 634 is open, the recessed portion 639 is located near the opening of the housing of the smear sample preparing apparatus 300, and thus, the user can easily attach/detach the first storage container 601 to/from the recessed portion 639.

FIG. 19 is referred to, again. The first storage container 601 and the second storage container 602 have an identical shape. Thus, in the first storage container 601, a maximum of ten glass slides 10 each in a standing state can be stored arranged alongside one another in the Y direction.

At the Y2 direction side of each of the first setting section 610 and the second setting section 620, a detector 640 for detecting the glass slide 10 stored in the first storage container 601 is provided. The detector 640 is a proximity sensor, and, for example, a photo interrupter, a photo reflector, or the like can be employed.

When the first transportation section 730 is to be moved between the staining processing section 160 and the slide setting section 170, or between the taking-out position 410 and the slide setting section 170, if the first transportation section 730 is to pass through a position at the Y2 direction side of the first setting section 610 or the second setting section 620, the glass slide 10 gripped by the first transportation section 730 will interfere with the detector 640. Therefore, the first transportation section 730 passes between the first setting section 610 and the second setting section 620, and between the two detectors 640. The first setting section 610 and the second setting section 620 are separated from each other in the X direction by a distance greater than the width of one glass slide 10, and the two detectors 640 are separated from each other in the X direction by a distance greater than the width of one glass slide 10. Thus, the glass slide 10 gripped by the first transportation section 730 is prevented from interfering with the detectors 640.

More specifically, when the first transportation section 730 transports the glass slide 10 from the taking-out position 410 to the slide setting section 170, the first transportation section 730 grips the glass slide 10 at the taking-out position 410, moves in the Z1 direction, and then takes out the glass slide 10 from the accommodation part 151. Then, the first transportation section 730 moves in the Y1 direction, passes between the two detectors 640, and reaches a position between the first setting section 610 and the second setting section 620. Further, the first transportation section 730 moves in the X1 direction or the X2 direction, locates the glass slide 10 above the first setting section 610 or the second setting section 620, moves in the Z2 direction, and stores the glass slide 10 in the first storage container 601. The first transportation section 730 releases the glass slide 10, moves in the Z1 direction, and further moves in the X2 direction or the X1 direction, and moves to a position between the first setting section 610 and the second setting section 620. Then, the first transportation section 730 moves in the Y2 direction, passes between the two detectors 640, and moves to the taking-out position 410 or the staining processing section 160.

When the first transportation section 730 transports a glass slide 10 from the slide setting section 170 to the staining processing section 160, the first transportation section 730 grips a glass slide 10 stored in the first storage container 601 at the first setting section 610 or the second setting section 620, moves in the Z1 direction, and takes out the glass slide 10 from the first storage container 601. Further, the first transportation section 730 moves in the X2 direction or the X1 direction, and moves to a position between the first setting section 610 and the second setting section 620. Then, the first transportation section 730 moves in the Y2 direction, passes between the two detectors 640, and moves to the staining processing section 160. The first transportation section 730 locates the glass slide 10 above the first staining chamber 711 of the staining processing section 160, moves in the Z2 direction, and inserts the glass slide 10 into the first staining chamber 711. The first transportation section 730 releases the glass slide 10, moves in the Z1 direction, further moves in the Y1 direction, and moves to the taking-out position 410 or the slide setting section 170.

The slide setting section 170 may further include a first lock part 641 and a second lock part 642. The first lock part 641 and the second lock part 642 have a common configuration with each other. Each of the first lock part 641 and the second lock part 642 includes a bar member not shown that can be inserted in a lock hole provided in the cover 634. The bar member is driven by an actuator such as an air cylinder, a solenoid, or a motor. Each of the first lock part 641 and the second lock part 642 can perform locking, by inserting the bar member into the lock hole in the cover 634 in a closed state. Each of the first lock part 641 and the second lock part 642 can perform unlocking by pulling the bar member from the lock hole in the cover 634. Each of the first lock part 641 and the second lock part 642 can prohibit setting and taking-out of the first storage container 601, by locking the cover 634, and can permit setting and taking-out of the first storage container 601, by unlocking the cover 634.

(Operation of Smear Sample Preparing Apparatus)

In the smear sample preparing apparatus 300, an operation mode of either a sampler mode or a manual mode can be set. The sampler mode is an operation mode in which a specimen is aspirated from a specimen container 211 automatically transported by the specimen transportation section 210, the smearing process is performed on a glass slide 10 by use of this specimen, and the staining process is performed on the glass slide 10. The manual mode is an operation mode in which processes are performed by use of a specimen container or a glass slide manually set by the user.

The manual mode includes a smear mode. The smear mode is an operation mode in which: a specimen is aspirated from a specimen container set by the user in the specimen container setting part 811; the smearing process is performed on a glass slide 10 by use of this specimen; and the staining process is not performed on the glass slide 10.

The manual mode may include a smear-stain mode, a print mode, and a stain mode. The smear-stain mode is an operation mode in which: a specimen is aspirated from a specimen container set by the user in the specimen container setting part 811; the smearing process is performed on a glass slide 10 by use of this specimen; and the staining process is performed on the glass slide 10. The print mode is an operation mode in which: the printing process is performed on a glass slide 10; and the smearing process and the staining process are not performed on the glass slide 10. The stain mode is an operation mode in which: the staining process is performed on a glass slide 10 set by the user in the slide setting section 170; and the smearing process and the printing process are not performed on the glass slide 10.

<Sampler Mode>

Figure 21:
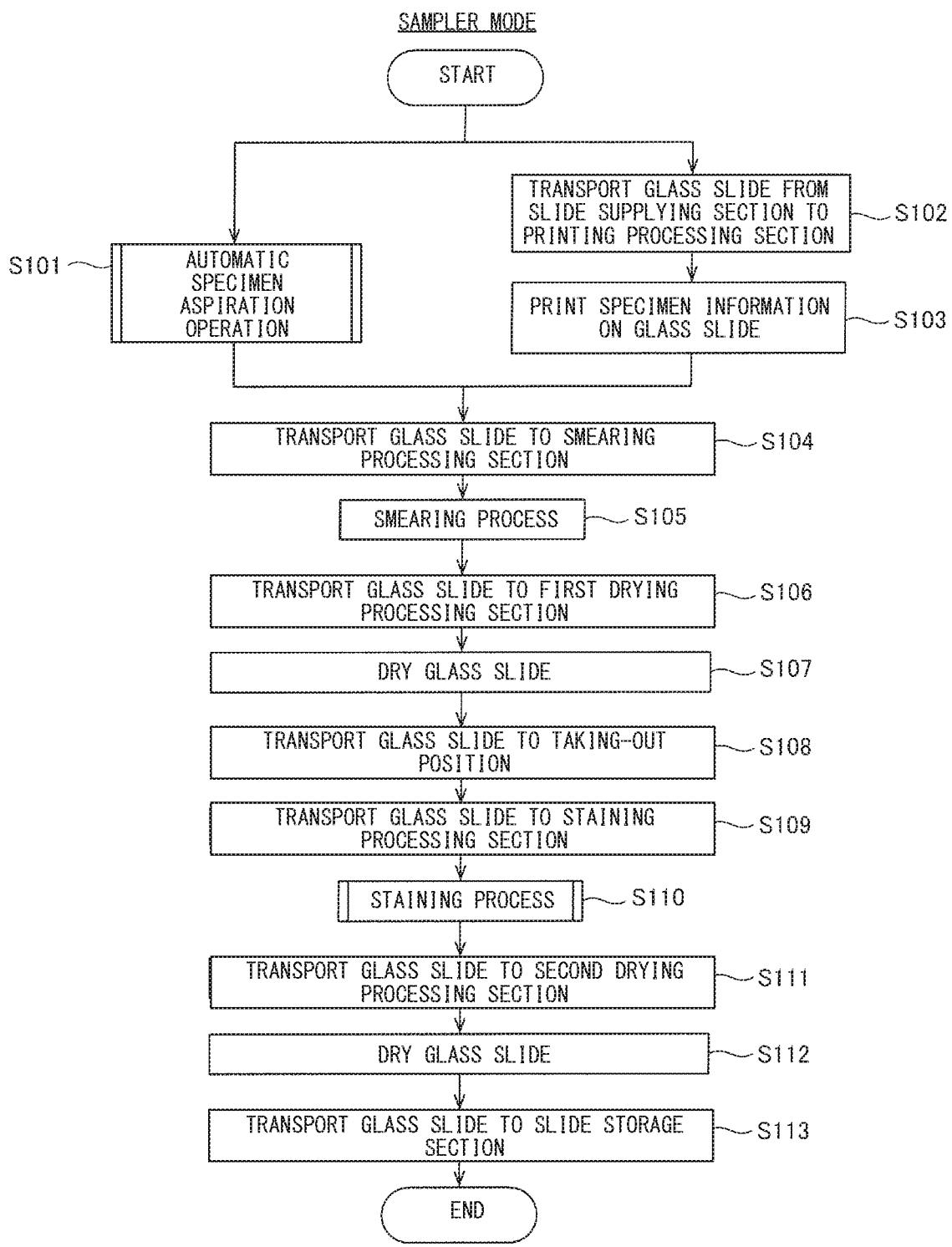
FIG. 21 is a flow chart showing the procedure of a sampler mode.

In the smear sample preparing apparatus 300, the sampler mode is set as the initial setting. Operation of the smear sample preparing apparatus 300 in the sampler mode is described with reference to FIG. 21.

Figure 22:
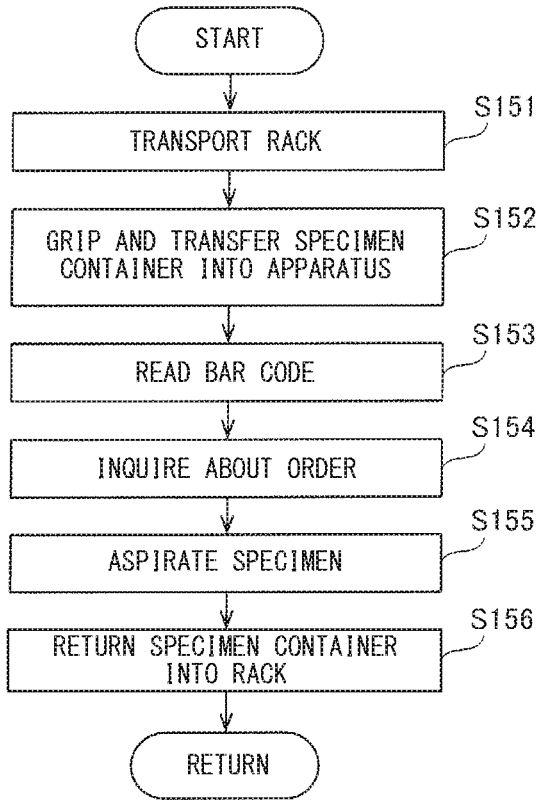
FIG. 22 is a flow chart showing the procedure of automatic specimen aspiration operation.

In the sampler mode, the specimen transportation section 210 and the aspirator 220 perform automatic specimen aspiration operation (S101). The automatic specimen aspiration operation is operation of aspirating a specimen from a specimen container 211 automatically transported by the specimen transportation section 210. The automatic specimen aspiration operation is described with reference to FIG. 22.

The specimen transportation section 210 transports a rack 212 and locates one specimen container 211 at the supply position 805 (S151). The grip part 814 takes out the specimen container 211 at the supply position 805 from the rack 212, agitates the specimen, and then transfers the specimen container 211 into the smear sample preparing apparatus 300 (S152).

The specimen container setting part 811 transfers the specimen container 211 to the reading position 815, and the bar code reader 812 reads the specimen ID from the bar code of the specimen container 211 (S153). The controller 230 transmits the read specimen ID to a host computer not shown, and inquires about an order (S154). The order includes a smearing condition and a staining condition. The specimen container setting part 811 transfers the specimen container 211 to the aspiration position 816, and the aspiration tube 813 aspirates the specimen from the specimen container 211 (S155). Then, the specimen container setting part 811 returns the specimen container 211 to the original position thereof in the rack 212, and the automatic specimen aspiration operation ends.

FIG. 21 is referred to, again. In parallel with the automatic specimen aspiration operation described above, the first slide transportation section 120 transports a glass slide 10 having no specimen smeared thereon, from the slide supplying section 20 to the printing processing section 30A (S102). The printing processing section 30A prints specimen information such as the specimen ID read by the bar code reader 812, in a frosted area (not shown) which is a printing region at an end portion of the glass slide 10 (S103).

Next, the first slide transportation section 120 transports the glass slide 10 on which the printing process has been performed, to the smearing processing section 40A (S104). The smearing processing section 40A performs the smearing process by use of the specimen aspirated by the aspiration tube 813, on the glass slide 10 on which the printing process has been performed (S105).

The first slide transportation section 120 transports the glass slide 10 on which the smearing process has been performed, to the first drying processing section 50 (S106). The first drying processing section 50 dries the glass slide 10 on which the smearing process has been performed (S107).

When the drying by the first drying processing section 50 is completed, the first slide transportation section 120 transports the dried glass slide 10 to the accommodation part 151 of the second slide transportation section 150. The accommodation part 151 accommodating the glass slide 10 stands up, moves in the X1 direction, and transports the glass slide 10 to the taking-out position 410 (S108).

When the glass slide 10 reaches the taking-out position 410, the first transportation section 730 transports the glass slide 10 from the taking-out position 410 to the staining processing section 160 (S109). This operation is further described in detail. The first transportation section 730 grips the glass slide 10 in a standing state and located at the taking-out position 410, and moves in the Z1 direction to take out the glass slide 10 from the accommodation part 151. Then, the first transportation section 730 moves in the horizontal direction, locates the glass slide 10 above the first staining chamber 711, and moves in the Z2 direction to insert the glass slide 10 into the first staining chamber 711. The first transportation section 730 releases the glass slide 10, and moves in the Z1 direction.

Figure 23:
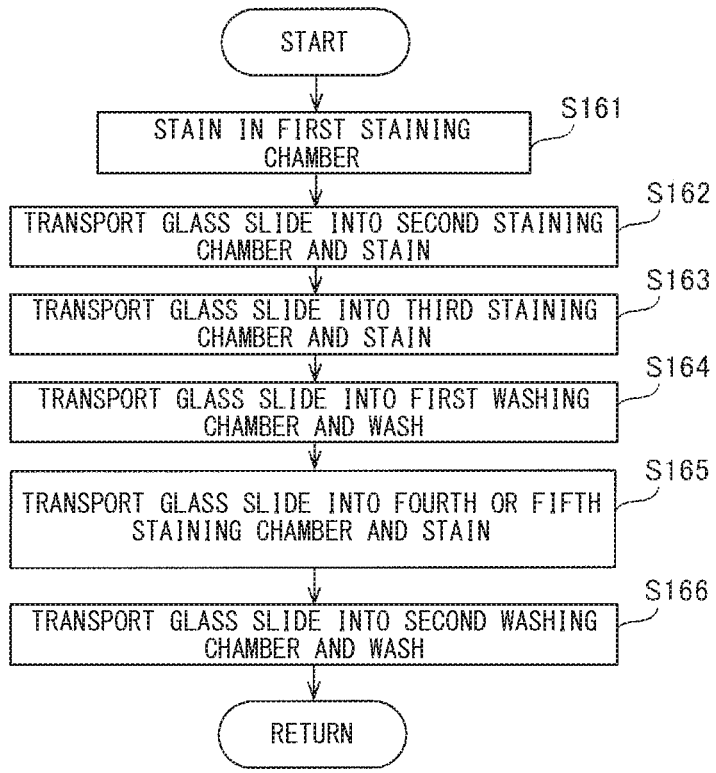
FIG. 23 is a flow chart showing the procedure of a staining process.

Next, the staining processing section 160 performs the staining process on the glass slide 10 transported by the first transportation section 730 (S110). The staining process is described with reference to FIG. 23.

First, staining is performed in the first staining chamber 711 (S161). Specifically, in the first staining chamber 711, a first staining liquid 701 is stored. As a result of the glass slide 10 being immersed in the first staining liquid 701 for a predetermined set time period T1, the specimen smeared on the glass slide 10 is stained.

Next, the first transportation section 730 transports the glass slide 10 from the first staining chamber 711 to the second staining chamber 712, and the staining processing section 160 stains the specimen smeared on the glass slide 10, in the second staining chamber 712 (S162). Specifically, the first transportation section 730 grips the glass slide 10 inserted in the first staining chamber 711, and moves in the Z1 direction to take out the glass slide 10 from the first staining chamber 711. Then, the first transportation section 730 moves in the Y2 direction, locates the glass slide 10 above the second staining chamber 712, and moves in the Z2 direction to insert the glass slide 10 into the second staining chamber 712. The first transportation section 730 releases the glass slide 10 and moves in the Z1 direction. In the second staining chamber 712, a second staining liquid 701 is stored. As a result of the glass slide 10 being immersed in the second staining liquid 701 for a predetermined set time period T2, the specimen smeared on the glass slide 10 is stained.

Next, the first transportation section 730 transports the glass slide 10 from the second staining chamber 712 to the third staining chamber 713, and the staining processing section 160 stains the specimen smeared on the glass slide 10, in the third staining chamber 713 (S163). Since the operation of the first transportation section 730 and the second transportation section 740 in S163 to S166 is similar to the transportation of the glass slide from the first staining chamber 711 to the second staining chamber 712, the description thereof is omitted. In the third staining chamber 713, a third staining liquid 701 is stored. As a result of the glass slide 10 being immersed in the third staining liquid 701 for a predetermined set time period T3, the specimen smeared on the glass slide 10 is stained.

Next, the first transportation section 730 transports the glass slide 10 from the third staining chamber 713 to the first washing chamber 721, and the staining processing section 160 washes the glass slide 10 in the first washing chamber 721 (S164). In the first washing chamber 721, a first washing liquid 702 is stored. As a result of the glass slide 10 being immersed in the first washing liquid 702 for a predetermined set time period T4, the glass slide 10 is washed.

Next, the second transportation section 740 transports the glass slide 10 from the first washing chamber 721 to the fourth staining chamber 714 or the fifth staining chamber 715, and the staining processing section 160 stains the specimen smeared on the glass slide 10, in the fourth staining chamber 714 or the fifth staining chamber 715 (S165). In the fourth staining chamber 714 and the fifth staining chamber 715, the same fourth staining liquid 701 is stored. As a result of the glass slide 10 being immersed in the fourth staining liquid 701 for a predetermined set time period T5, the specimen smeared on the glass slide 10 is stained.

Next, the second transportation section 740 transports the glass slide 10 from the fourth staining chamber 714 or the fifth staining chamber 715 to the second washing chamber 722, and the staining processing section 160 washes the glass slide 10 in the second washing chamber 722 (S166). In the second washing chamber 722, a second washing liquid 702 is stored. As a result of the glass slide 10 being immersed in the second washing liquid 702 for a predetermined set time period T6, the glass slide 10 is washed. Then, the staining process on the glass slide 10 ends.

FIG. 21 is referred to, again. When the staining process ends, the second transportation section 740 transports the glass slide 10 from the second washing chamber 722 to the accommodation part 771 of the second drying processing section 190 (S111). The operation of the second transportation section 740 at this time is also the same as the operation of the first transportation section 730 in S162, and thus, description thereof is omitted.

The air-blowing part 772 blows air into the accommodation part 771, to dry the glass slide 10 accommodated in the accommodation part 771 (S112).

When drying by the second drying processing section 190 is completed, the second transportation section 740 transports the dried glass slide 10 to the slide storage section 200 (S113). Specifically, the second transportation section 740 grips the glass slide 10 accommodated in the accommodation part 771, and moves in the Z1 direction to take out the glass slide 10 from the accommodation part 771. Then, the second transportation section 740 moves in the X1 direction, locates the glass slide 10 above the storing position 412 of the slide storage section 200, and moves in the Z2 direction to store the glass slide 10 in the second storage container 602 at the storing position 412. The second transportation section 740 releases the glass slide 10 and moves in the Z1 direction.

In the sampler mode, the specimen transportation section 210 sequentially transports the racks 212, and the aspirator 220 sequentially takes out a specimen container 211 from each rack 212 and aspirates the specimen from the specimen container 211. In addition, the first slide transportation section 120, the second slide transportation section 150, and the first transportation section 730 sequentially transport the glass slide from the slide supplying section 20, through the printing processing section 30A, the smearing processing section 40A, the first drying processing section 50, the staining processing section 160, and the second drying processing section 190, to the slide storage section 200. Accordingly, for each glass slide 10, the printing process, the smearing process, and the staining process are sequentially performed, and each glass slide 10 is stored in the second storage container 602 set in the slide storage section 200.

In this sampler mode, the printing process by the printing processing section 30A, the smearing process by the smearing processing section 40A, and the staining process by the staining processing section 160 are performed in parallel. In the staining process, staining in the first staining chamber 711, staining in the second staining chamber 712, staining in the third staining chamber 713, washing in the first washing chamber 721, staining in the fourth staining chamber 714 or the fifth staining chamber 715, and washing in the second washing chamber 722 are performed in parallel.

<Manual Mode>

Next, the manual mode is described with reference to FIG. 24. While the sampler mode is being performed, if the user presses a mode change button (not shown) provided to the housing of the smear sample preparing apparatus 300, the user can provide the smear sample preparing apparatus 300 with an instruction to switch to the manual mode. The controller 230 determines whether or not the instruction to switch to the manual mode has been received (S201), and when the instruction to switch to the manual mode has not been received (NO in S201), the controller 230 repeats the process of step S201. As a result, the sampler mode is continued.

When the instruction to switch to the manual mode has been received (YES in S201), the controller 230 determines whether or not the aspirator 220 has taken a specimen container 211 into the smear sample preparing apparatus 300 (S202). When the specimen container 211 has not been taken into the smear sample preparing apparatus 300 (NO in S202), the controller 230 shifts the process to S204.

When the specimen container 211 has been taken into the smear sample preparing apparatus 300 (YES in S202), the controller 230 determines whether or not the taken-in specimen container 211 has been returned to the rack 212 (S203). When the specimen container 211 has not been returned to the rack 212 (NO in S203), the controller 230 repeats the process of S203, and waits until the specimen container 211 is returned to the rack 212.

When the specimen container 211 has been returned to the rack 212 (YES in S203), the controller 230 controls the specimen transportation section 210 and the specimen transportation section 210 suspends transportation of the rack 212 (S204). As a result of this, the sampler mode is suspended. Meanwhile, the aspirator 220 sends out the specimen container setting part 811 to the outside of the housing of the smear sample preparing apparatus 300 (S205).

Figure 25:
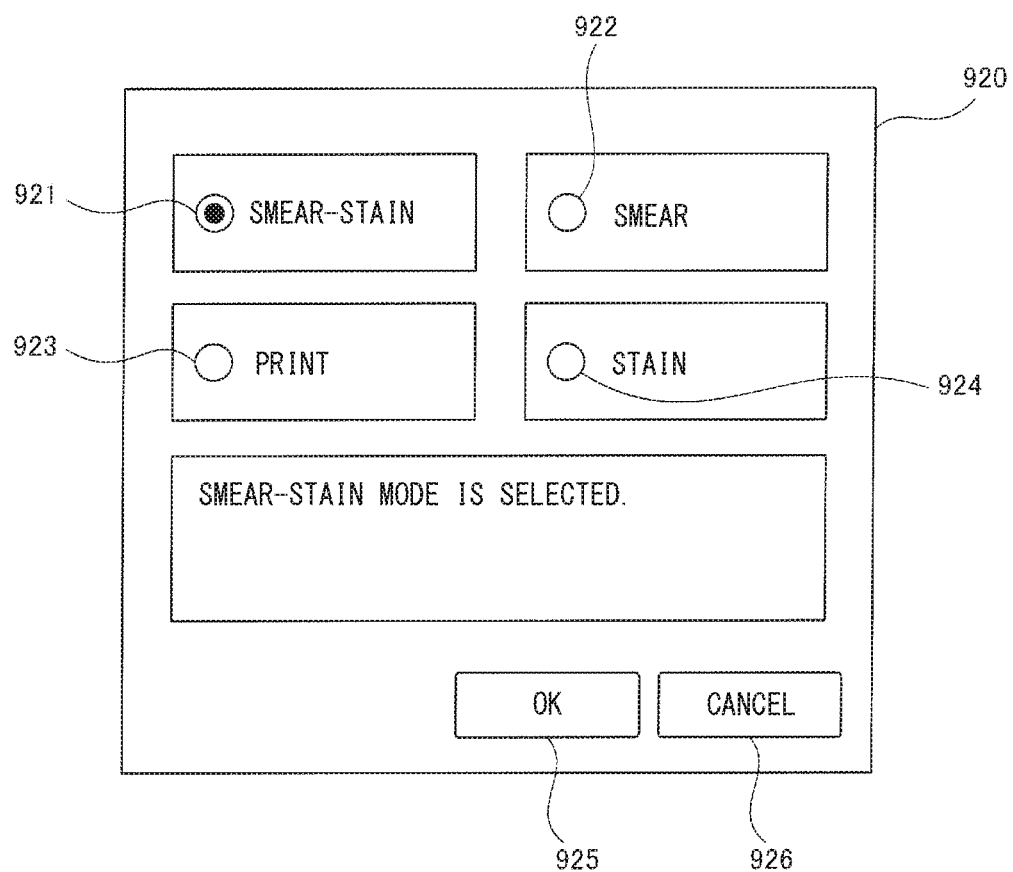
FIG. 25 is a diagram showing a manual mode screen.

The controller 230 causes the output unit 231 to display a manual mode screen (S206). Here, the manual mode screen is described with reference to FIG. 25. The manual mode screen is a screen for the user to select any one of the smear-stain mode, the smear mode, the print mode, and the stain mode. A manual mode screen 920 includes: a selection part 921 for selecting the smear-stain mode; a selection part 922 for selecting the smear mode; a selection part 923 for selecting the print mode; a selection part 924 for selecting the stain mode; an OK button 925 for fixing the selection; and a cancel button 926 for canceling the selection. The user selects one of the selection parts 921 to 924 that corresponds to a desired mode, and selects the OK button, thereby fixing the selection of the mode.

FIG. 24 is referred to, again. The controller 230 receives the selection of the mode from the user (S207), and determines which mode has been selected (S208). When the smear-stain mode has been selected ("smear-stain mode" in S208), the controller 230 performs the smear-stain mode (S209). When the smear mode has been selected ("smear mode" in S208), the controller 230 performs the smear mode (S210). When the print mode has been selected ("print mode" in S208), the controller 230 performs the print mode (S211). When the stain mode has been selected ("stain mode" in S208), the controller 230 performs the stain mode (S212). When the operation in the performed mode ends, the controller 230 ends the manual mode.

Figure 24:
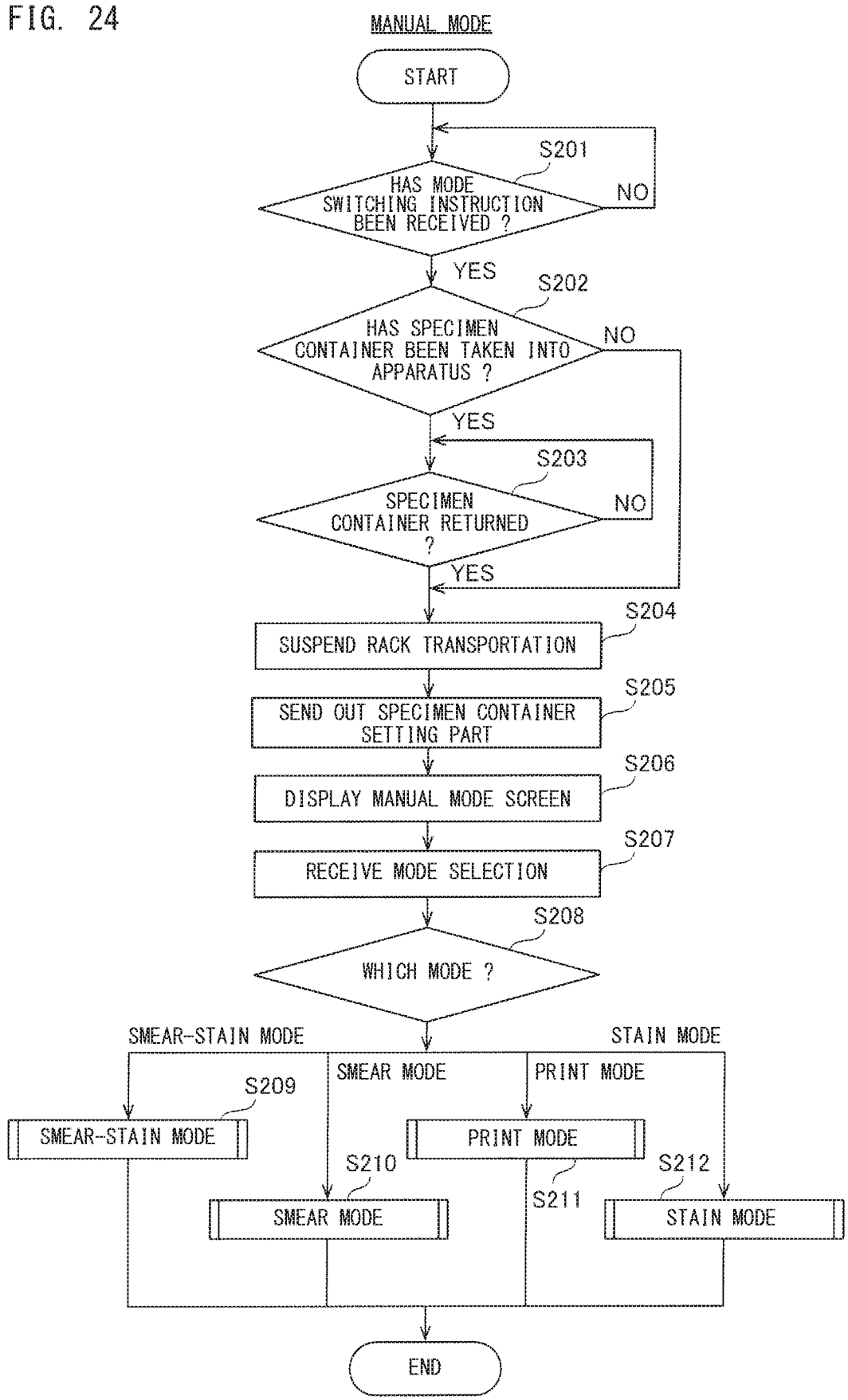
FIG. 24 is a flow chart showing the procedure of a manual mode.

In the example shown in FIG. 24, the sampler mode is shifted to the manual mode on the basis of an input performed on the mode change button not shown (S201), and the shift to each mode is made on the basis of a selection operation performed on the manual mode screen (S207). However, the shift to each mode may be made on the basis of an event other than an input operation.

For example, in the stain mode, as described later, a first storage container 601 storing an unstained glass slide 10 is set in the slide setting section 170 by the user, and the glass slide 10 is detected by a detector 640. Thus, when the detector 640 detects the glass slide 10 in the first storage container 601 set by the user, the mode may be shifted to the stain mode without receiving an input operation from the user.

<Smear-Stain Mode>

Figure 26:
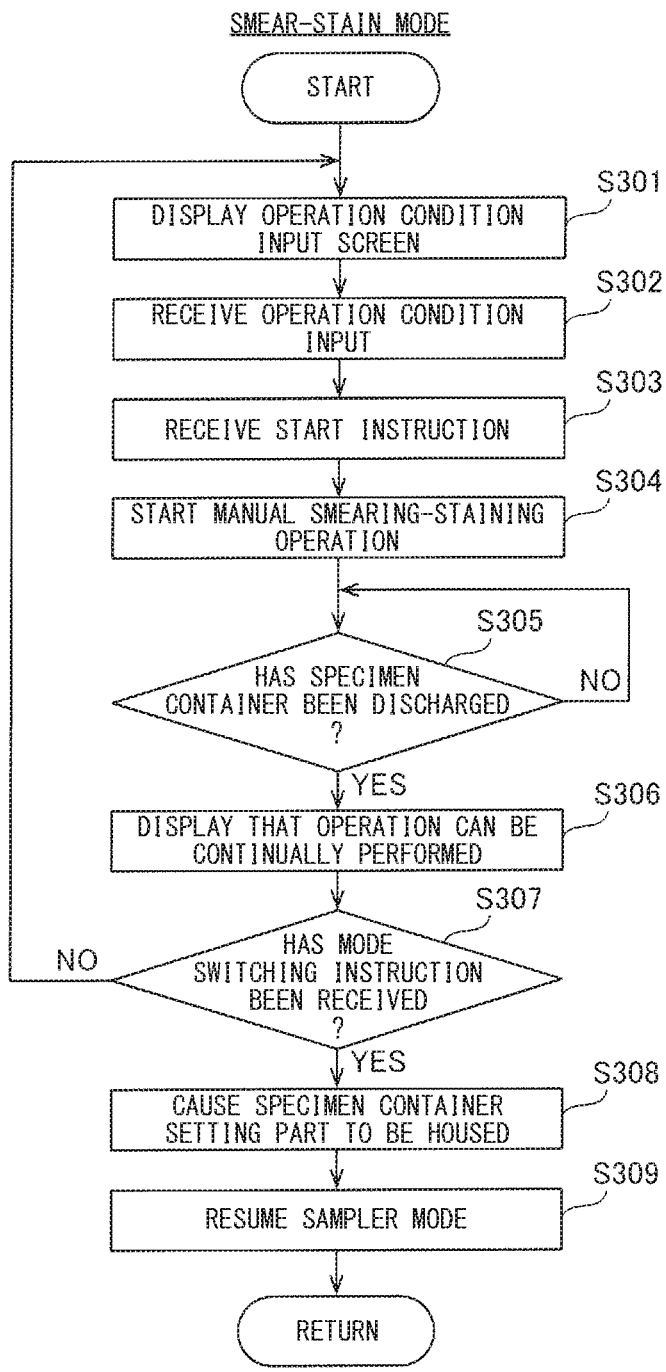
FIG. 26 is a flow chart showing the procedure of a smear-stain mode.

The smear-stain mode is described with reference to FIG. 26.

When the smear-stain mode is started, the controller 230 causes the output unit 231 to display an operation condition input screen (S301).

Here, the operation condition input screen is described with reference to FIG. 27. An operation condition input screen 930 is a screen for designating an operation condition in the smear-stain mode. On the operation condition input screen 930, the user can input an operation condition such as: whether or not to perform reading of a specimen ID or a bar code; the type of the specimen container 211; the presence/absence of a cap of the specimen container 211; a smearing condition; which one of the two slide supplying sections 20 (the first supplying section 21 or the second supplying section 22) the glass slide 10 to be used comes from; and the number of glass slides on which one specimen is to be smeared.

FIG. 26 is referred to, again. The controller 230 receives an input of the operation condition performed on the operation condition input screen 930 (S302).

When the user presses a start button (not shown) provided to the housing of the smear sample preparing apparatus 300, the user can provide the smear sample preparing apparatus 300 with an instruction to start operation in the smear sample mode according to the inputted operation condition (hereinafter, referred to as "manual smearing-staining operation"). The user sets a specimen container 211 in the specimen container setting part 811, and presses the start button to provide an instruction to start the manual smearing-staining operation. The controller 230 receives the instruction to start the manual smearing-staining operation (S303), and starts the manual smearing-staining operation (S304).

Figure 28:
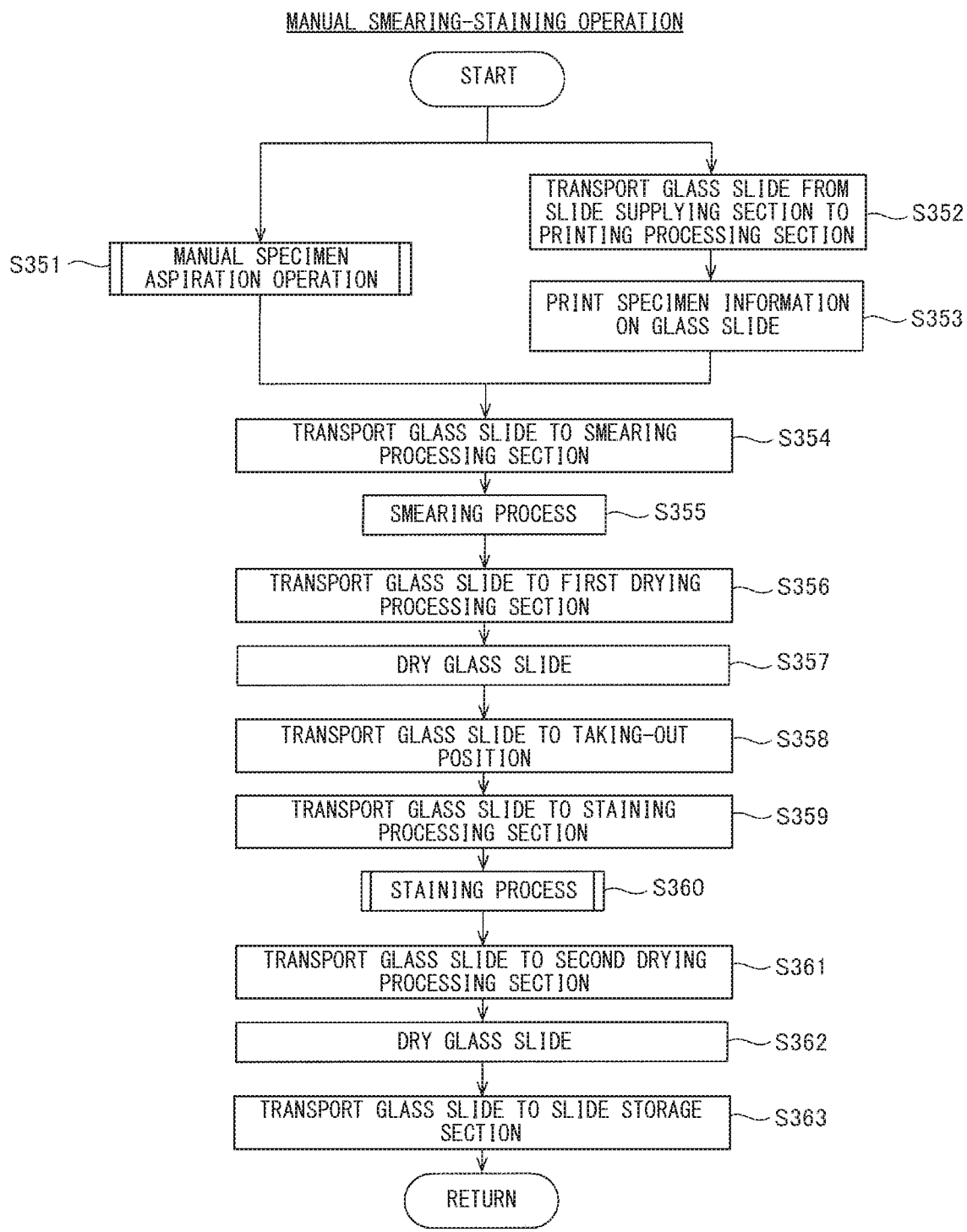
FIG. 28 is a flow chart showing the procedure of manual smearing-staining operation.

As shown in FIG. 28, the manual smearing-staining operation is the same as the sampler mode except that the automatic specimen aspiration operation (S101) is replaced by "manual specimen aspiration operation". The manual specimen aspiration operation is operation in which the specimen is aspirated from the specimen container 211 set by the user in the specimen container setting part 811. That is, in the manual smearing-staining operation, the smearing processing section 40A smears the specimen aspirated from the specimen container 211 set by the user in the specimen container setting part 811, onto a glass slide 10 supplied from the slide supplying section 20. The glass slide 10 on which the smearing process has been performed is dried by the first drying processing section 50, then transported to the staining processing section 160, and is subjected to the staining process. The glass slide 10 on which the staining process has been performed is dried by the second drying processing section 190, and then transported to the slide storage section 200.

Figure 29:
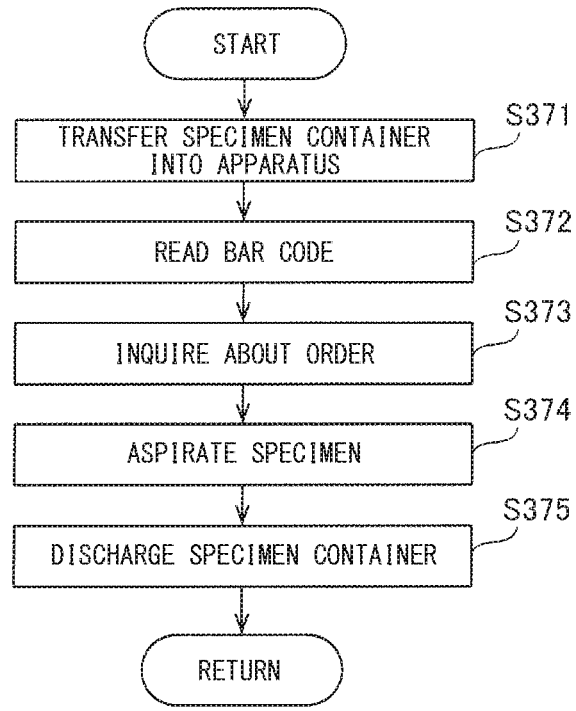
FIG. 29 is a flow chart showing the procedure of manual specimen aspiration operation.

The manual specimen aspiration operation is described with reference to FIG. 29. The specimen container setting part 811 moves into the smear sample preparing apparatus 300. Accordingly, the specimen container 211 is transferred into the smear sample preparing apparatus 300 (S371). Step S372 to step S374 are the same as steps S153 to S155 in the automatic specimen aspiration operation, and thus, description thereof is omitted.

After the specimen has been aspirated by the aspiration tube 813, the specimen container setting part 811 moves to the outside of the housing of the smear sample preparing apparatus 300. Accordingly, the specimen container 211 is discharged to the outside of the smear sample preparing apparatus 300 (S375). Then, the manual specimen aspiration operation ends.

FIG. 26 is referred to, again. The controller 230 determines whether or not the specimen container 211 has been discharged to the outside of the smear sample preparing apparatus 300 (S305). When the specimen container 211 is inside the smear sample preparing apparatus 300 (NO in S305), the controller 230 repeats the process of step S305, and waits until the specimen container 211 is discharged to the outside of the smear sample preparing apparatus 300 in the manual smearing-staining operation.

When the specimen container 211 has been discharged to the outside of the smear sample preparing apparatus 300 (YES in S305), the controller 230 causes the output unit 231 to display information indicating that the manual smearing-staining operation can be continually performed (S306). When the manual smearing-staining operation is to be continually performed, the user replaces the specimen container 211 set in the specimen container setting part 811, with another specimen container 211. When the smear sample preparing apparatus 300 is to be restored to the sampler mode, the user presses the mode change button, thereby being able to provide the smear sample preparing apparatus 300 with an instruction to switch to the sampler mode.

The controller 230 determines whether or not the instruction to switch to the sampler mode has been received (S307), and when the instruction to switch to the sampler mode has not been received (NO in S307), the controller 230 returns the process to step S301. As a result, the manual smearing-staining operation is continually performed.

When the instruction to switch to the sampler mode has been received (YES in S307), the controller 230 causes the specimen container setting part 811 to be housed in the housing of the smear sample preparing apparatus 300 (S308), and resumes the sampler mode (S309). Then, the smear-stain mode ends.

<Smear Mode>

The smear mode is described with reference to FIG. 30A to FIG. 30C.

When the smear mode is started, the controller 230 causes the output unit 231 to display an operation condition input screen (S401).

The operation condition input screen is the same as the operation condition input screen displayed in the smear-stain mode. However, since the staining process is not performed in the smear mode, the operation condition input screen is configured so as not to allow inputting of a staining condition.

The controller 230 receives an input of an operation condition performed on the operation condition input screen (S402).

When the user presses the start button, the user can provide the smear sample preparing apparatus 300 with an instruction to start operation in the smear mode according to the inputted operation condition (hereinafter, referred to as "manual smearing operation"). The user sets a specimen container 211 in the specimen container setting part 811, and presses the start button to provide an instruction to start the manual smearing operation. The controller 230 receives the instruction to start the manual smearing operation (S403).

The controller 230 determines whether or not there is vacancy in the first storage container 601 set in the slide setting section 170 (S404). Specifically, when no glass slide 10 stored in the first storage container 601 has been detected by the detector 640, the controller 230 can determine that there is vacancy in the first storage container 601. Here, when a glass slide 10 has been detected by one of the detectors 640, and no glass slide 10 has been detected by the other of the detectors 640, it is possible to determine that there is no vacancy in the first storage container 601 in which the glass slide 10 has been detected, and that there is vacancy in the first storage container 601 in which no glass slide 10 has been detected.

Alternatively, in a case where a glass slide 10 has been detected by a detector 640, if the first transportation section 730 sequentially moves to each holding position in the first storage container 601, grips a glass slide 10, and performs rising operation, it is also possible to determine whether or not a glass slide 10 is stored at each holding position. At a holding position where a glass slide 10 is stored, the first transportation section 730 pulls out the glass slide 10, and thus, the detector 640 detects the pulled-out glass slide 10. At a holding position where no glass slide 10 is stored, the first transportation section 730 pulls out no glass slide 10, and thus, the detector 640 detects no glass slide 10. In this manner, when there is a holding position where no glass slide 10 is stored, the controller 230 can also determine that there is vacancy in the first storage container 601.

Alternatively, a configuration is also possible in which: the controller 230 stores in advance the storage state of the glass slides 10 in each first storage container 601; and when there is a holding position where no glass slide 10 is stored, the controller 230 determines that there is vacancy in a corresponding first storage container 601.

When there is no vacancy in the first storage container 601 (NO in S404), the controller 230 causes the output unit 231 to display error information (S405), and returns the process to step S404. If there is no vacancy for storing the glass slide 10 in the slide setting section 170, the glass slide 10 on which the smearing process has been performed cannot be stored in the slide setting section 170. Therefore, in such a case, by outputting error information, it is possible to urge the user to perform replacement with a first storage container 601 having vacancy.

When there is vacancy in a first storage container 601 (YES in S404), the controller 230 sets the first storage container 601 having vacancy as a transportation target (S406).

The controller 230 locks the cover 634 of the first storage container 601 serving as the transportation target (S407). Specifically, in a case where the transportation target is the first storage container 601 that is set in the first setting section 610, the first lock part 641 locks the cover 634. In a case where the transportation target is the first storage container 601 that is set in the second setting section 620, the second lock part 642 locks the cover 634. Accordingly, the first storage container 601 serving as the transportation target is prohibited from being taken out, and thus, the user is prevented from touching the first storage container 601 serving as the transportation target. Meanwhile, the cover 634 of the first storage container 601 that is not the transportation target is not locked. Thus, for example, when there is no vacancy in this first storage container 601, the user can replace this first storage container 601 with a first storage container 601 having vacancy.

Next, the controller 230 starts the manual smearing operation (S408).

Figure 31:
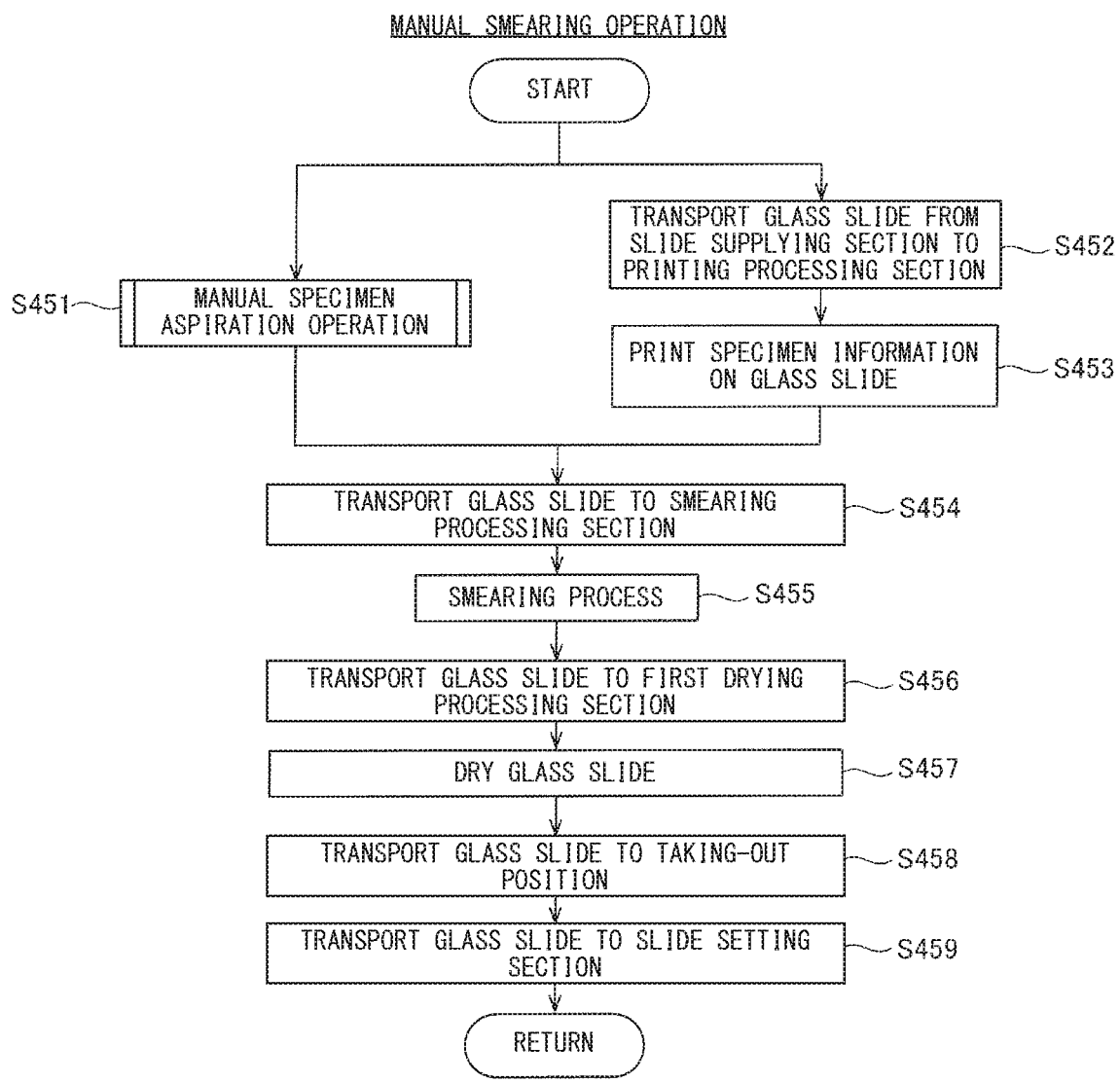
FIG. 31 is a flow chart showing the procedure of manual smearing operation.

As shown in FIG. 31, steps S451 to S458 in the manual smearing operation are the same as step S351 to step S358 in the manual smearing-staining operation shown in FIG. 28. That is, in the manual smearing operation, the smearing processing section 40A smears the specimen aspirated from the specimen container 211 set by the user in the specimen container setting part 811, onto a glass slide 10 supplied from the slide supplying section 20. The glass slide 10 on which the smearing process has been performed is subjected to the drying process by the first drying processing section 50, and then transported to the taking-out position 410.

When the smeared glass slide 10 reaches the taking-out position 410, the first transportation section 730 transports the smeared glass slide 10 from the taking-out position 410 to the first storage container 601 serving as the transportation target (S459).

FIG. 30A is referred to, again. The controller 230 determines whether or not the specimen container 211 has been discharged to the outside of the smear sample preparing apparatus 300 (S409). When the specimen container 211 is inside the smear sample preparing apparatus 300 (NO in S409), the controller 230 repeats the process of step S409, and waits until the specimen container 211 is discharged to the outside of the smear sample preparing apparatus 300 in the manual smearing operation.

When the specimen container 211 has been discharged to the outside of the smear sample preparing apparatus 300 (YES in S409), the controller 230 causes the output unit 231 to display information indicating that the manual smearing operation can be continually performed (S410). When the manual smearing operation is to be continually performed, the user replaces the specimen container 211 set in the specimen container setting part 811, with another specimen container 211. When the smear sample preparing apparatus 300 is to be restored to the sampler mode, the user presses the mode change button, thereby being able to provide the smear sample preparing apparatus 300 with an instruction to switch to the sampler mode.

The controller 230 determines whether or not the instruction to switch to the sampler mode has been received (S411). When the instruction to switch to the sampler mode has been received (YES in S411), the controller 230 causes the specimen container setting part 811 to be housed in the housing of the smear sample preparing apparatus 300 (S412), and resumes the sampler mode (S413).

Next, the controller 230 determines whether or not all the glass slides 10 processed in the smear mode have been stored in the first storage container 601 (S414). When there is a glass slide 10 that is being processed in the smear mode and that is not yet stored in the first storage container 601 (NO in S414), the controller 230 repeats the process of step S414 and waits until all the glass slides 10 processed in the smear mode are stored in the first storage container 601.

When all the glass slides 10 processed in the smear mode have been stored in the first storage container 601 (YES in S414), the controller 230 cancels the setting of the first storage container 601 as the transportation target (S415), and unlocks the first lock part 641 or the second lock part 642 (S416). Then, the smear mode ends.

Accordingly, the glass slide 10 on which the staining process has not been performed and on which the smearing process has been performed can be transported to the slide setting section 170 without being transported to the staining processing section 160, and can be promptly taken out from the apparatus.

Meanwhile, when the instruction to switch to the sampler mode has not been received (NO in S411), the controller 230 determines whether or not the first storage container 601 serving as the transportation target is full (S417). When there is vacancy in the first storage container 601 serving as the transportation target (NO in S417), the controller 230 returns the process to step S408. As a result, the manual smearing operation is continually performed.

When the first storage container 601 serving as the transportation target is full (YES in S417), the controller 230 unlocks the cover 634 of the first storage container 601 serving as the transportation target (S418), and changes the transportation target setting to the other of the first storage containers 601 (S419). Thus, the first storage container 601 that has become full can be replaced with a first storage container 601 having vacancy.

Next, the controller 230 determines whether or not there is vacancy in the first storage container 601 serving as the transportation target (S420). In this process, similarly to step S404, the controller 230 may determine that there is vacancy when the detector 640 has detected no glass slide 10, or may determine whether or not there is vacancy at each holding position in the first storage container 601.

When there is no vacancy in the first storage container 601 serving as the transportation target (NO in S420), the controller 230 causes the output unit 231 to display error information (S421), and returns the process to step S420. Accordingly, it is possible to urge the user to perform replacement with a first storage container 601 having vacancy.

When there is vacancy in the first storage container 601 serving as the transportation target (YES in S420), the controller 230 locks the cover 634 of the first storage container 601 serving as the transportation target (S422), and returns the process to step S408. As a result, the manual smearing operation is continually performed.

<Print Mode>

The print mode is described with reference to FIG. 32A to FIG. 32C.

When the print mode is started, the controller 230 causes the output unit 231 to display an operation condition input screen (S501).

Figure 33:
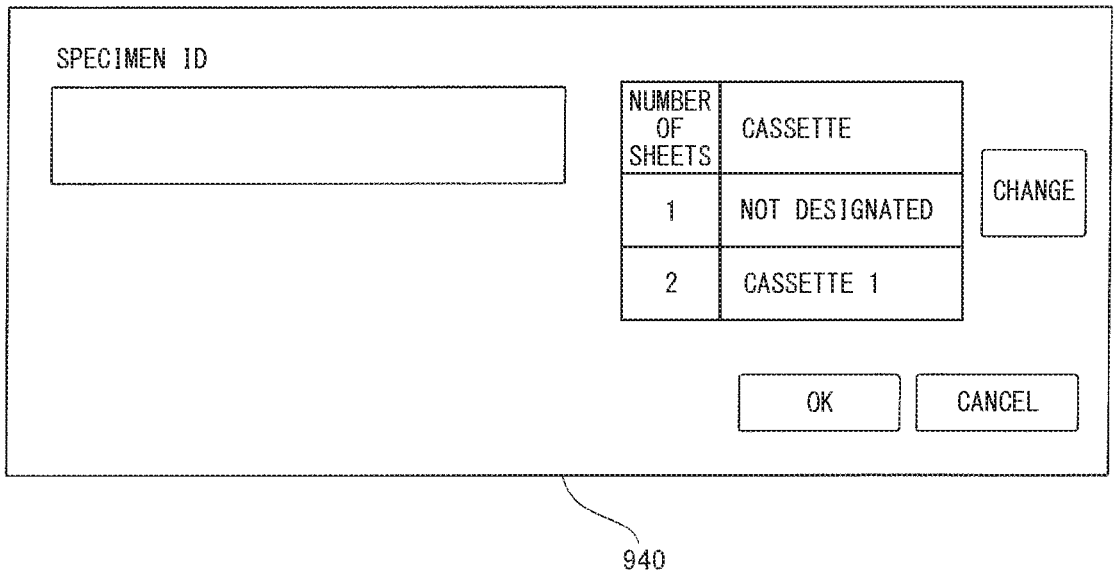
FIG. 33 is a diagram showing an operation condition input screen in the print mode.

Here, with reference to FIG. 33, the operation condition input screen is described. An operation condition input screen 940 is a screen for designating an operation condition in the print mode. On the operation condition input screen 940, the user can input an operation condition such as: a specimen ID; and which one of the two slide supplying sections 20 (the first supplying section 21 or the second supplying section 22) the glass slide 10 to be used comes from.

FIG. 32A is referred to, again. Steps S502 to S507 are the same as steps S402 to S407 in the smear mode shown in FIG. 30A, and thus, description thereof is omitted.

After the cover of the first storage container 601 serving as the transportation target is locked, the controller 230 starts manual printing operation (S508).

Figure 34:
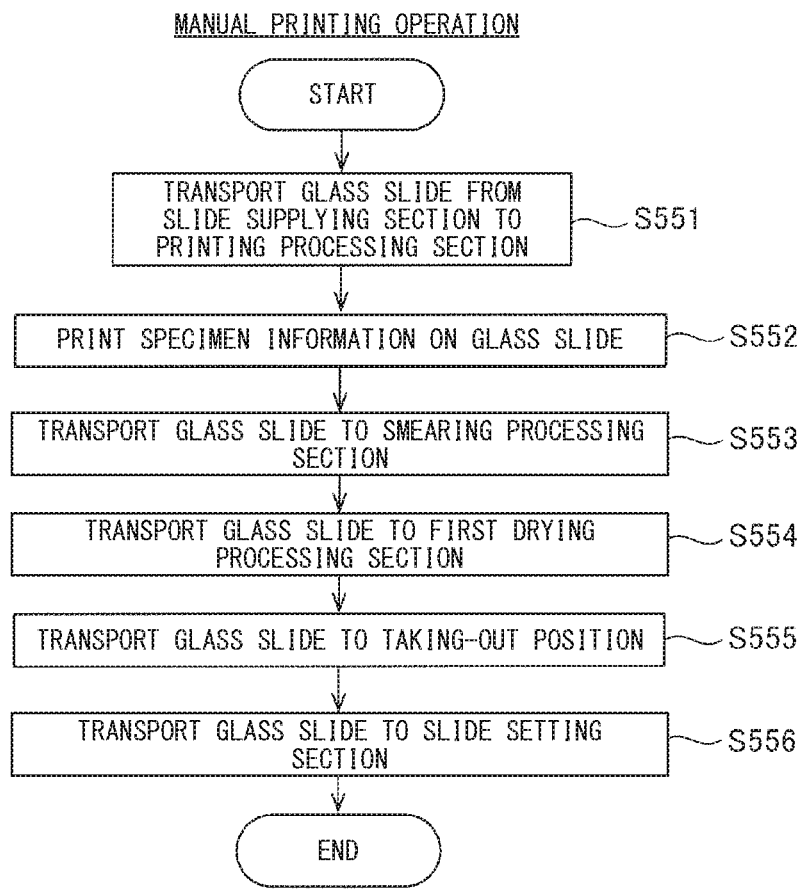
FIG. 34 is a flow chart showing the procedure of manual printing operation.

As shown in FIG. 34, steps S551 to S553 in the manual printing operation is the same as steps S352 to S354 in the manual smearing-staining operation shown in FIG. 28. That is, in the manual printing operation, the printing processing section 30A prints specimen information on a glass slide 10 supplied from the slide supplying section 20. The glass slide 10 on which the printing process has been performed is transported to the smearing processing section 40A.

In the manual printing operation, the smearing processing section 40A does not perform the smearing process on the glass slide 10. The first slide transportation section 120 transports the glass slide 10 on which the printing process has been performed, to the first drying processing section 50 (S554).

In the manual printing operation, the first drying processing section 50 does not dry the glass slide 10, and the first slide transportation section 120 transports the glass slide 10 to the accommodation part 151 of the second slide transportation section 150. The accommodation part 151 accommodating the glass slide 10 stands up, moves in the X1 direction, and transports the glass slide 10 to the taking-out position 410 (S555).

When the glass slide 10 has reached the taking-out position 410, the first transportation section 730 transports the glass slide 10 from the taking-out position 410 to the first storage container 601 serving as the transportation target (S556).

Accordingly, the glass slide 10 on which the staining process and the smearing process have not been performed and on which the printing process has been performed can be transported to the slide setting section 170 without being transported to the staining processing section 160, and can be promptly taken out from the slide setting section 170.

FIG. 32A is referred to, again. In the manual printing operation described above, the specimen container setting part 811 remains outside the housing of the smear sample preparing apparatus 300. The controller 230 causes the output unit 231 to display information indicating that the manual printing operation can be continually performed (S509). When the manual printing operation is to be continually performed, the user causes the output unit to display the operation condition input screen 940 again. When the smear sample preparing apparatus 300 is to be restored to the sampler mode, the user presses the mode change button, thereby being able to provide the smear sample preparing apparatus 300 with an instruction to switch to the sampler mode.

Figure 30A:
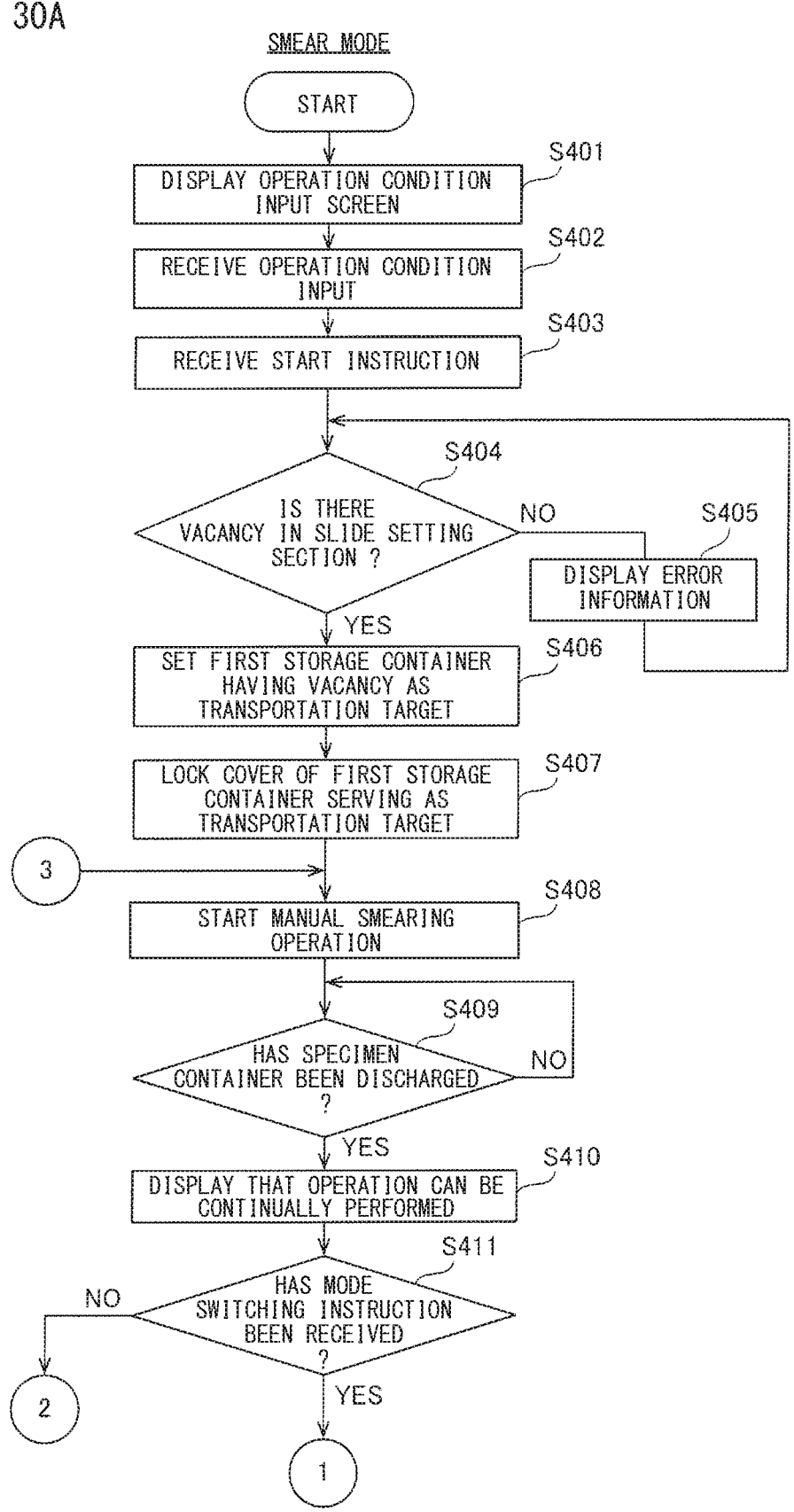
FIG. 30A is a flow chart showing the procedure of a smear mode.
Figure 30B:
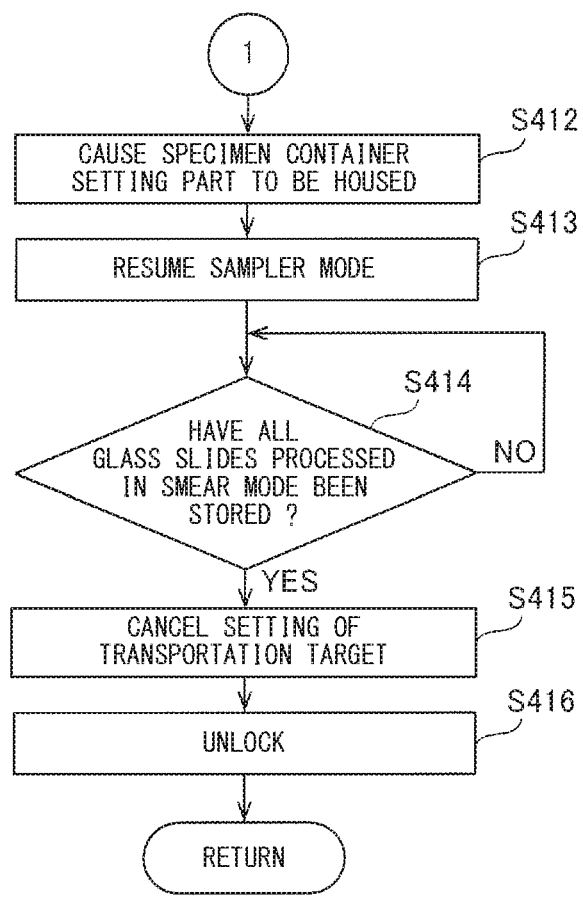
FIG. 30B is a flow chart showing the procedure of the smear mode.
Figure 30C:
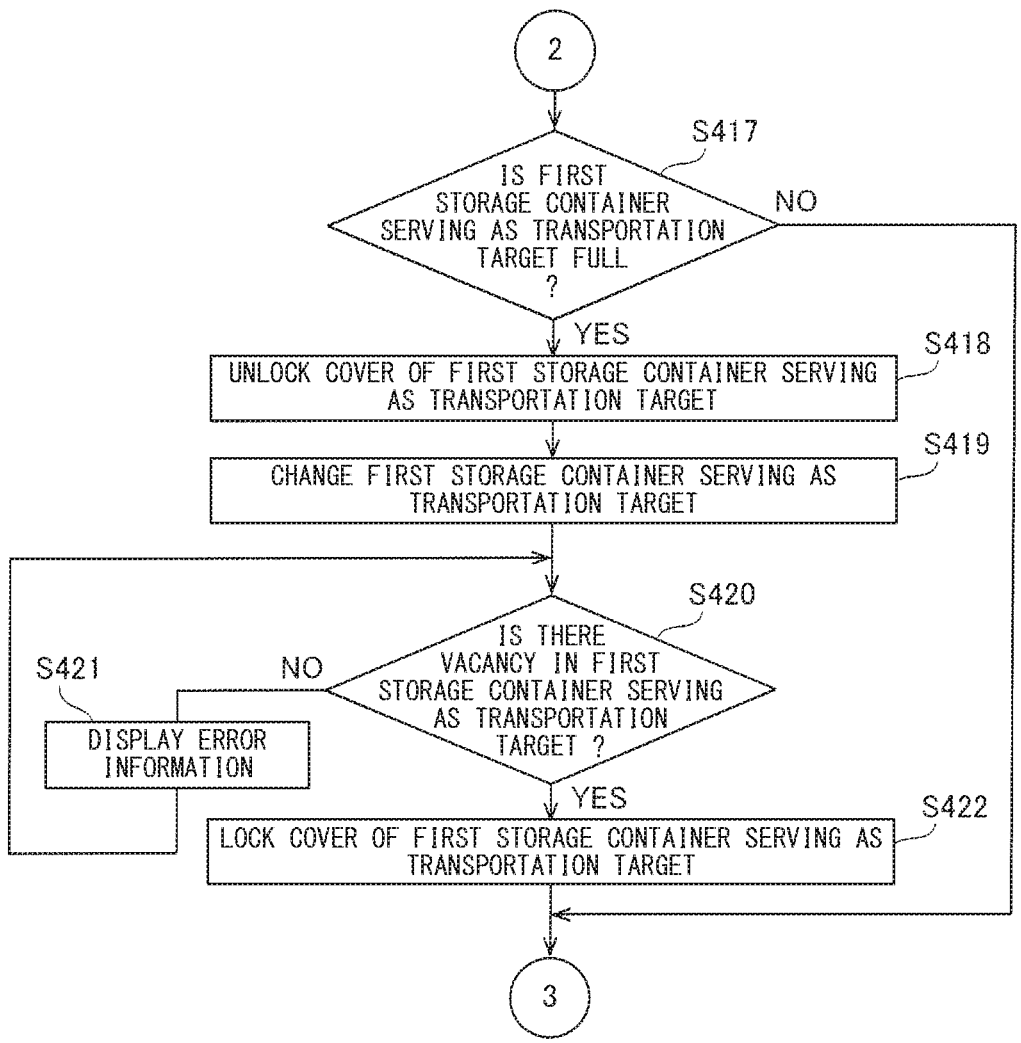
FIG. 30C is a flow chart showing the procedure of the smear mode.
Figure 32A:
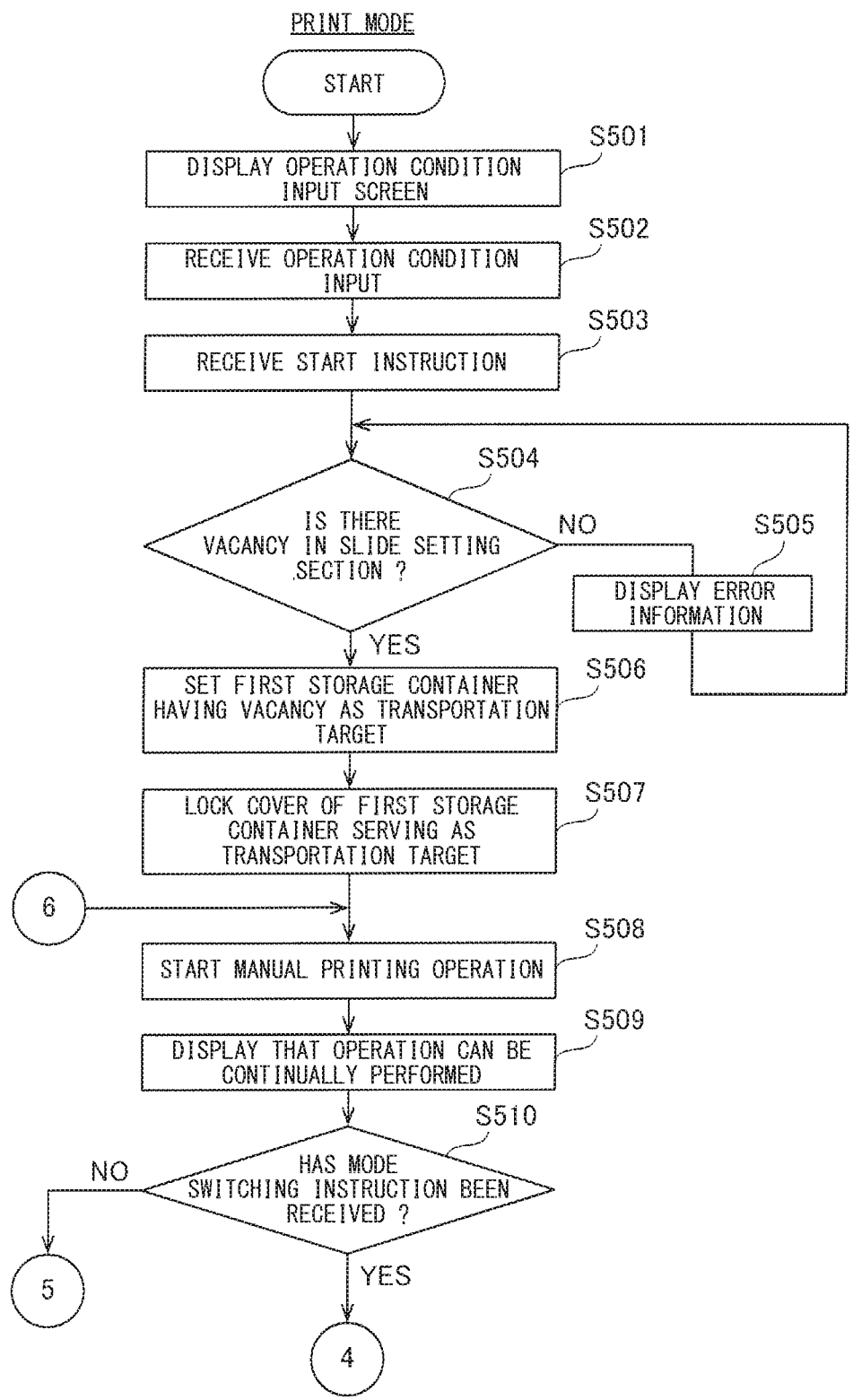
FIG. 32A is a flow chart showing the procedure of a print mode.
Figure 32B:
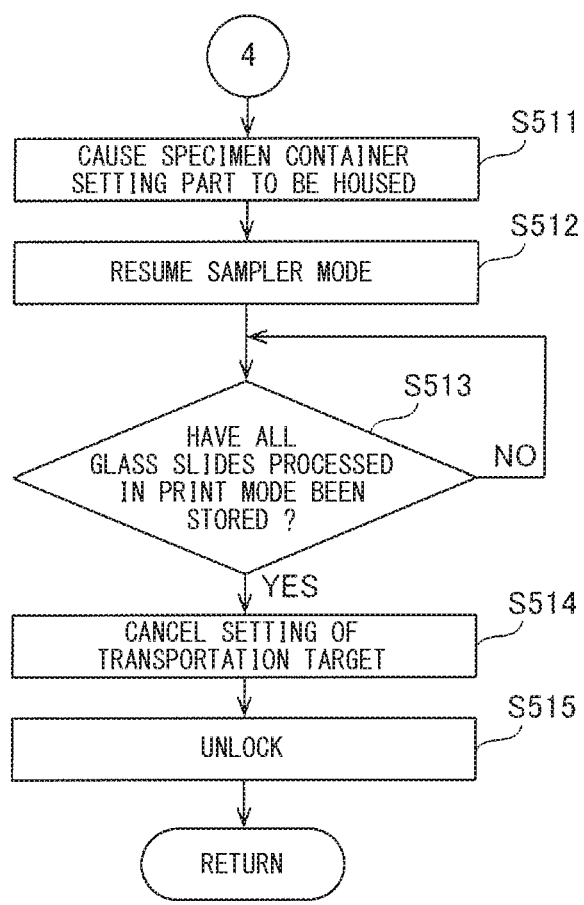
FIG. 32B is a flow chart showing the procedure of the print mode.
Figure 32C:
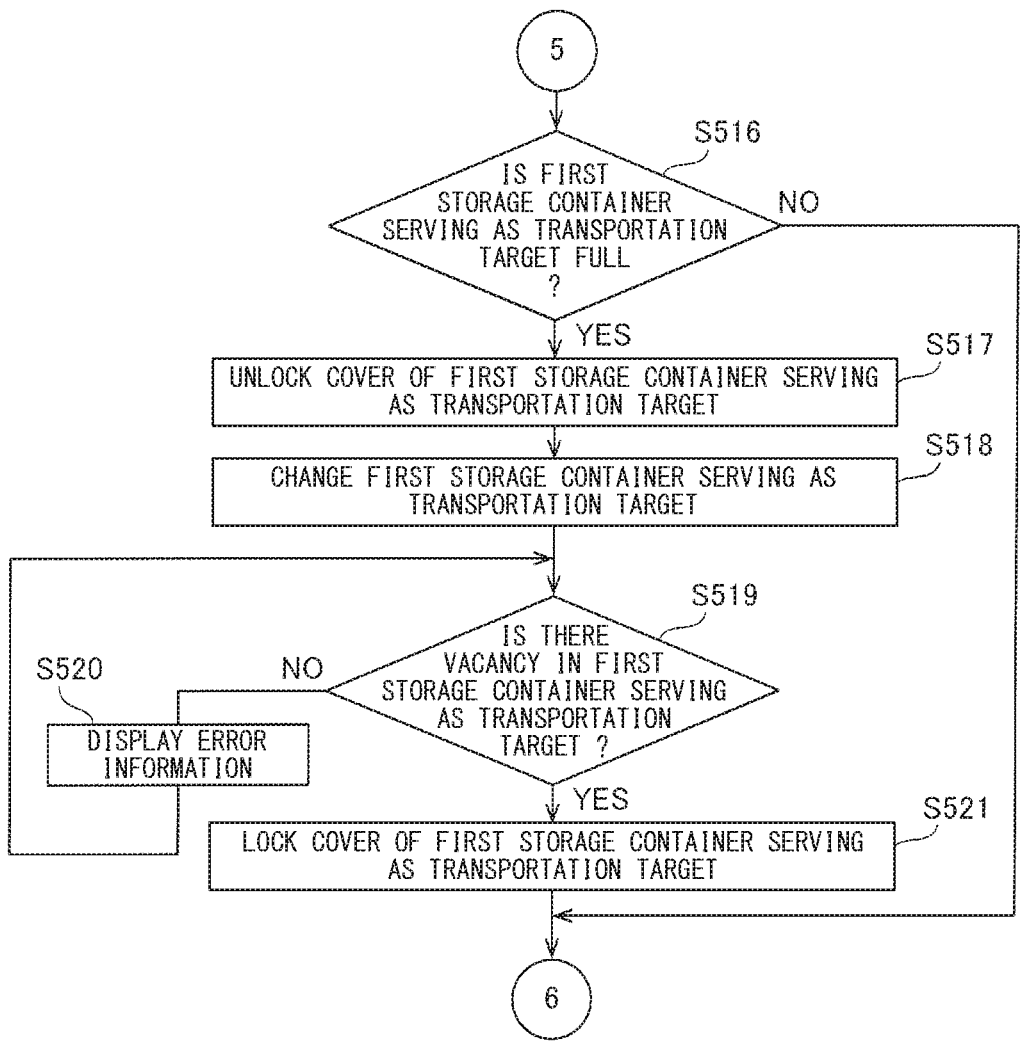
FIG. 32C is a flow chart showing the procedure of the print mode.

Step S510 to step S521 shown in FIG. 32A to FIG. 32C are the same as step S411 to step S422 in the smear mode shown in FIG. 30A to FIG. 30C, and thus, description thereof is omitted.

Next, another example of the print mode is described with reference to FIG. 35.

In the example shown in FIG. 35, the controller 230 is configured as follows. That is, when the controller 230 has received the setting of the print mode (see S201 to S211 in FIG. 24) during the process according to the sampler mode control (see S101 to S113 in FIG. 21), the controller 230 interrupts the process of the sampler mode, performs the print mode control (S551 to S556 in FIG. 34) of causing the printing processing section 30A to perform the printing process on a glass slide on which the staining process and the smearing process are not performed, and resumes the sampler mode control after performing the print mode control.

Accordingly, after the sampler mode has been shifted to the manual print mode, restoration from the manual print mode to the sampler mode is automatically performed. Thus, the user need not perform work for restoration to the sampler mode. That is, the user need not take the trouble to press the mode change button after the manual printing has been performed, and restoration to the sampler mode is reliably enabled. As a result, the burden on the user of managing the state of the smear sample preparing apparatus 300 is reduced, and thus, convenience of the smear sample preparing apparatus 300 is improved.

Figure 35:
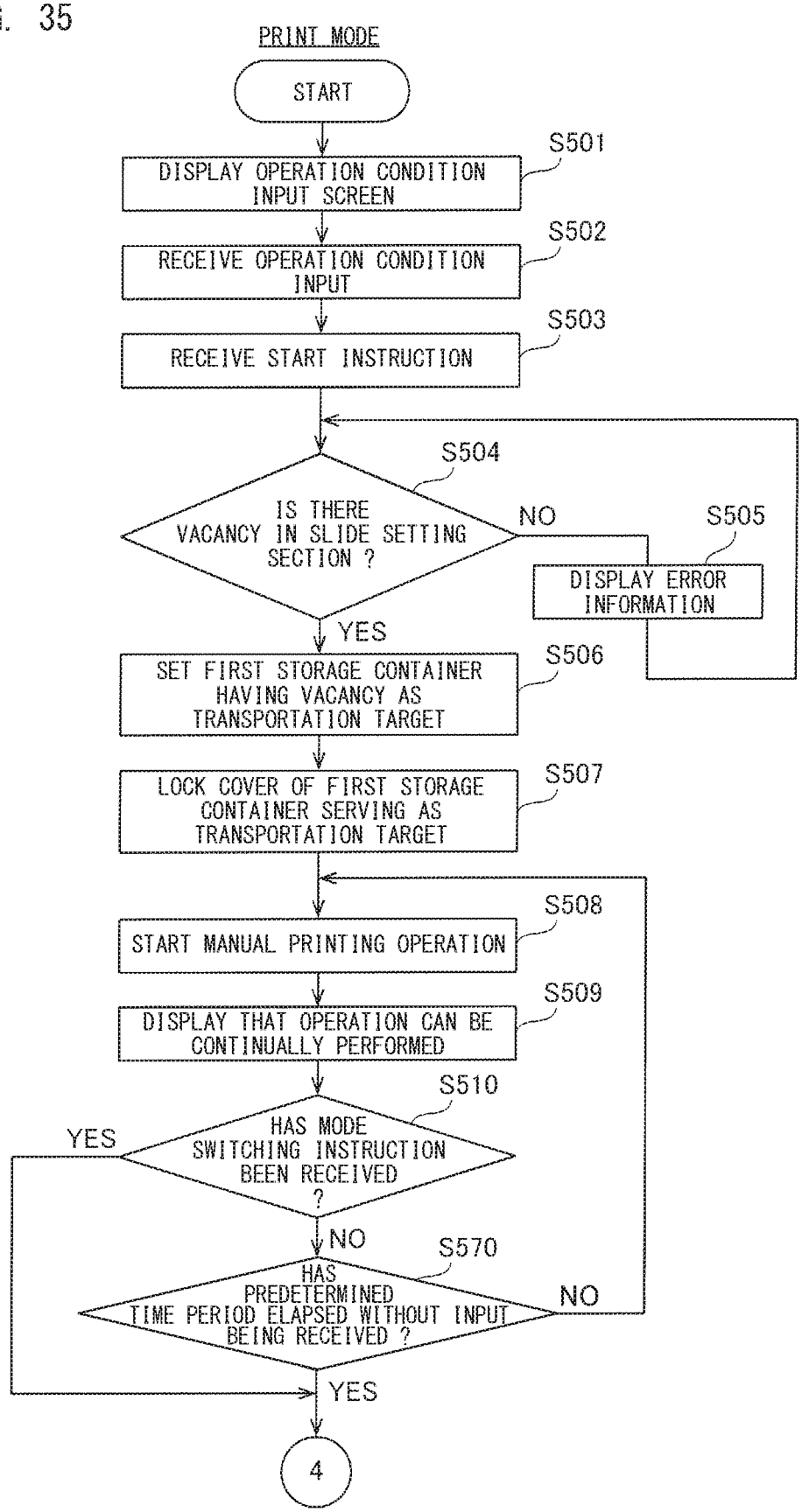
FIG. 35 is a flow chart showing another example of the print mode.

Steps S501 to S510 shown in FIG. 35 are the same as the process of the print mode shown in FIG. 32A, and thus, description thereof is omitted.

When the controller 230 has not received the instruction to switch to the sampler mode (NO in S510), the controller 230 causes the output unit 231 to display information indicating that the manual printing operation can be continually performed, and then, determines whether or not a predetermined time period has elapsed, without any input received (S570). That is, after the start of the printing operation on an immediately preceding glass slide 10 (S508), the controller 230 causes the output unit to display the operation condition input screen 940 for performing printing on the next glass slide 10 (S509), and then, determines whether or not the predetermined time period has elapsed, without any input received. The predetermined time period may be any time period. The predetermined time period is 5 minutes, for example.

When the controller 230 has received an information input on the operation condition input screen 940 for performing printing on the next glass slide 10 before the predetermined time period has elapsed (NO in S570), the controller 230 starts the printing operation on the next glass slide 10 (S508). That is, the controller 230 performs the print mode control of steps S551 to S556.

When the predetermined time period has elapsed without the controller 230 receiving the input in step S570 (YES in S570), the controller 230 performs the process of steps S511 to S515 shown in FIG. 32B. Also when having received an instruction to switch to the sampler mode in step S510 (YES in S510), the controller 230 performs the process of steps S511 to S515 shown in FIG. 32B. In this case, the controller 230 resumes the sampler mode control in step S512.

As described above, in the print mode shown in FIG. 35, the controller 230 is configured to perform the print mode control (S551 to S556), and to resume the sampler mode control (S512) after performing the print mode control. In this example, the controller 230 is configured such that the controller 230 determines whether or not the predetermined time period has elapsed, without any input received (S570), and the print mode is automatically restored to the sampler mode on the basis of the elapsed time period. Accordingly, when the user wants the print mode to be continued, it is sufficient for the user to perform an information input on the operation condition input screen 940 within the predetermined time period. Also when the work in the print mode has been completed, the user is not required to perform specific operation, and the mode can be automatically restored to the sampler mode on the basis of the elapsed time period.

<Stain Mode>

The stain mode is described with reference to FIG. 36A and FIG. 36B.

When the stain mode is started, the controller 230 determines whether or not there is a glass slide 10 in the slide setting section 170 (S601). Specifically, when a glass slide 10 stored in the first storage container 601 has been detected by the detector 640, the controller 230 can determine that there is a glass slide 10 in the first storage container 601, and when no glass slide 10 stored in the first storage container 601 has been detected by the detector 640, the controller 230 can determine that there is no glass slide 10 in the first storage container 601.

When there is no glass slide 10 in the first storage container 601 (NO in S601), the controller 230 causes the output unit 231 to display error information (S602), and returns the process to step S601. If, in the slide setting section 170, there is no glass slide 10 having a specimen smeared thereon, no glass slide 10 can be supplied to the staining processing section 160 in the stain mode. Thus, by causing error information to be outputted in such a case, it is possible to urge the user to perform replacement with a first storage container 601 storing a glass slide 10 having a specimen smeared thereon.

When there is a glass slide 10 in the first storage container 601 (YES in S601), the controller 230 sets, as the transportation target, the first storage container 601 storing the glass slide 10 (S603).

In addition, the controller 230 locks the cover 634 of the first storage container 601 serving as the transportation target (S604). Accordingly, the user is prevented from touching the first storage container 601 serving as the transportation target. Here, the cover 634 of the first storage container 601 that is not the transportation target is not locked. Thus, for example, when there is no glass slide 10 in this first storage container 601, the user can replace this first storage container 601 with a first storage container 601 storing a glass slide 10.

Next, the controller 230 starts manual staining operation (S605).

Figure 37:
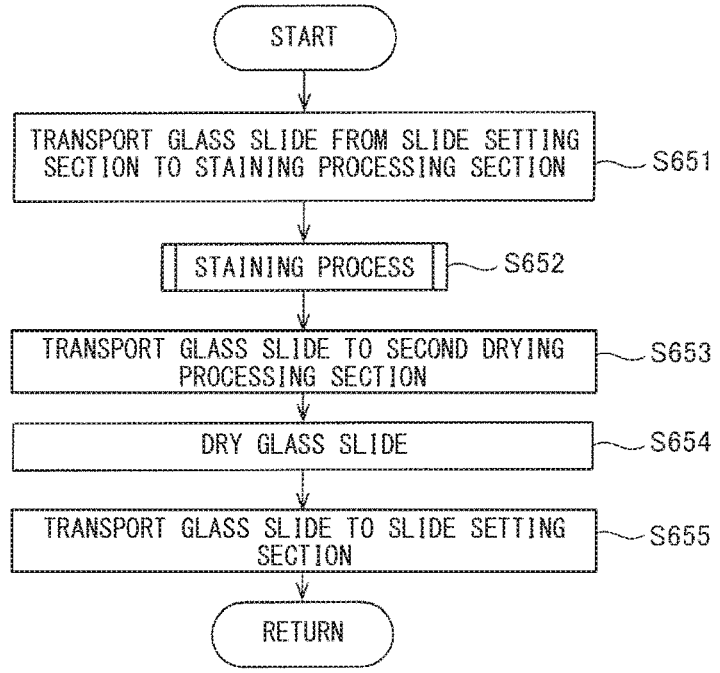
FIG. 37 is a flow chart showing the procedure of manual staining operation.

As shown in FIG. 37, in the manual staining operation, the first transportation section 730 transports the glass slide 10 from the first storage container 601 serving as the transportation target, to the first staining chamber 711 of the staining processing section 160. Thus, since the first transportation section 730 transports a glass slide 10 from the slide setting section 170 to the staining processing section 160, the slide setting section 170 can be used in two usages of taking out a glass slide 10 processed in the smear mode and the print mode, and supplying a glass slide 10 to be processed in the stain mode.

Next, the staining processing section 160 performs the staining process on the glass slide 10 transported by the first transportation section 730 (S652).

When the staining process has ended, the second transportation section 740 transports the glass slide 10 from the second washing chamber 722 to the second drying processing section 190 (S653). Next, the air-blowing part 772 blows air into the accommodation part 771, thereby drying the glass slide 10 accommodated in the accommodation part 771 (S654). When the drying by the second drying processing section 190 is completed, the second transportation section 740 transports the dried glass slide 10 to the slide storage section 200 (S655). Step S653 to step S655 are the same as step S111 to step S113 described above.

Thus, the glass slide 10 on which the smearing process has not been performed and on which the staining process has been performed can be transported to the slide storage section 200. That is, the glass slide 10 processed in the sampler mode, the smear-stain mode, and the stain mode, which is the glass slide 10 on which the staining process has been performed, can be transported from the staining processing section 160 to the slide storage section 200.

This manual staining operation is continually performed on all the glass slides 10 in the first storage container 601 serving as the transportation target.

FIG. 36A is referred to, again. The controller 230 determines whether or not the first storage container 601 serving as the transportation target has become empty (S606). Specifically, when the detector 640 no longer detects a glass slide 10 stored in the first storage container 601 serving as the transportation target, it is determined that this first storage container 601 has become empty.

When there is still a glass slide 10 remaining in the first storage container 601 serving as the transportation target (NO in S606), the controller 230 determines whether or not an instruction to switch to the sampler mode has been received (S607). When the instruction to switch to the sampler mode has not been received (NO in S607), the controller 230 returns the process to step S606, and determines again whether or not the first storage container 601 serving as the transportation target has become empty.

When the instruction to switch to the sampler mode has been received (YES in S607), the controller 230 unlocks the cover 634 of the first storage container 601 serving as the transportation target (S608).

Further, the controller 230 stops sending-out of the glass slide 10 from the first storage container 601 serving as the transportation target (S609). Accordingly, the glass slide 10 is no longer supplied to the staining processing section 160.

Next, the controller 230 cancels the setting of the first storage container 601 as the transportation target (S610), causes the specimen container setting part 811 to be housed in the housing of the smear sample preparing apparatus 300 (S611), and resumes the sampler mode (S612). Then, the stain mode ends.

When the first storage container 601 serving as the transportation target is empty (YES in S606), the controller 230 unlocks the cover 634 of the first storage container 601 serving as the transportation target (S613). Next, the controller 230 causes the output unit 231 to display information indicating that the manual staining operation can be continually performed (S614). When the manual staining operation is to be continually performed, the user does not press the mode change button, and when the sampler mode is to be restored, the user presses the mode change button.

The controller 230 determines whether or not an instruction to switch to the sampler mode has been received (S615).

When the instruction to switch to the sampler mode has been received (YES in S615), the controller 230 shifts the process to step S609.

Meanwhile, when the instruction to switch to the sampler mode has not been received (NO in S615), the controller 230 changes the setting of the transportation target to the other one of the first storage containers 601 (S616).

Next, the controller 230 determines whether or not there is a glass slide 10 in the first storage container 601 serving as the transportation target (S617). When there is no glass slide 10 in the first storage container 601 serving as the transportation target (NO in S617), the controller 230 causes the output unit 231 to display error information (S618), and returns the process to step S617. Accordingly, it is possible to urge the user to perform replacement with a first storage container 601 storing a glass slide 10.

When there is a glass slide 10 in the first storage container 601 serving as the transportation target (YES in S617), the controller 230 returns the process to step S604. Accordingly, the manual staining operation is continually performed.

Next, another example of the stain mode is described with reference to FIG. 38.

In the example shown in FIG. 38, the controller 230 is configured as follows. That is, when the controller 230 has received the setting of the stain mode (see S201 to S212 in FIG. 24) during the process according to the sampler mode control (see S101 to S113 in FIG. 21), the controller 230 interrupts the process of the sampler mode, performs the stain mode control (S651 to S655) of causing the staining processing section 160 to perform the staining process on the glass slide 10 from the first storage container 601, and resumes the sampler mode control after performing the stain mode control.

Accordingly, after the sampler mode has shifted to the manual stain mode, restoration from the manual stain mode to the sampler mode is automatically performed. Thus, the user need not perform work for restoration to the sampler mode. That is, the user need not take the trouble to press the mode change button after the manual staining has been performed, and restoration to the sampler mode is reliably enabled. As a result, the burden on the user of managing the state of the smear sample preparing apparatus 300 is reduced, and thus, convenience of the smear sample preparing apparatus 300 is improved.

Figure 36A:
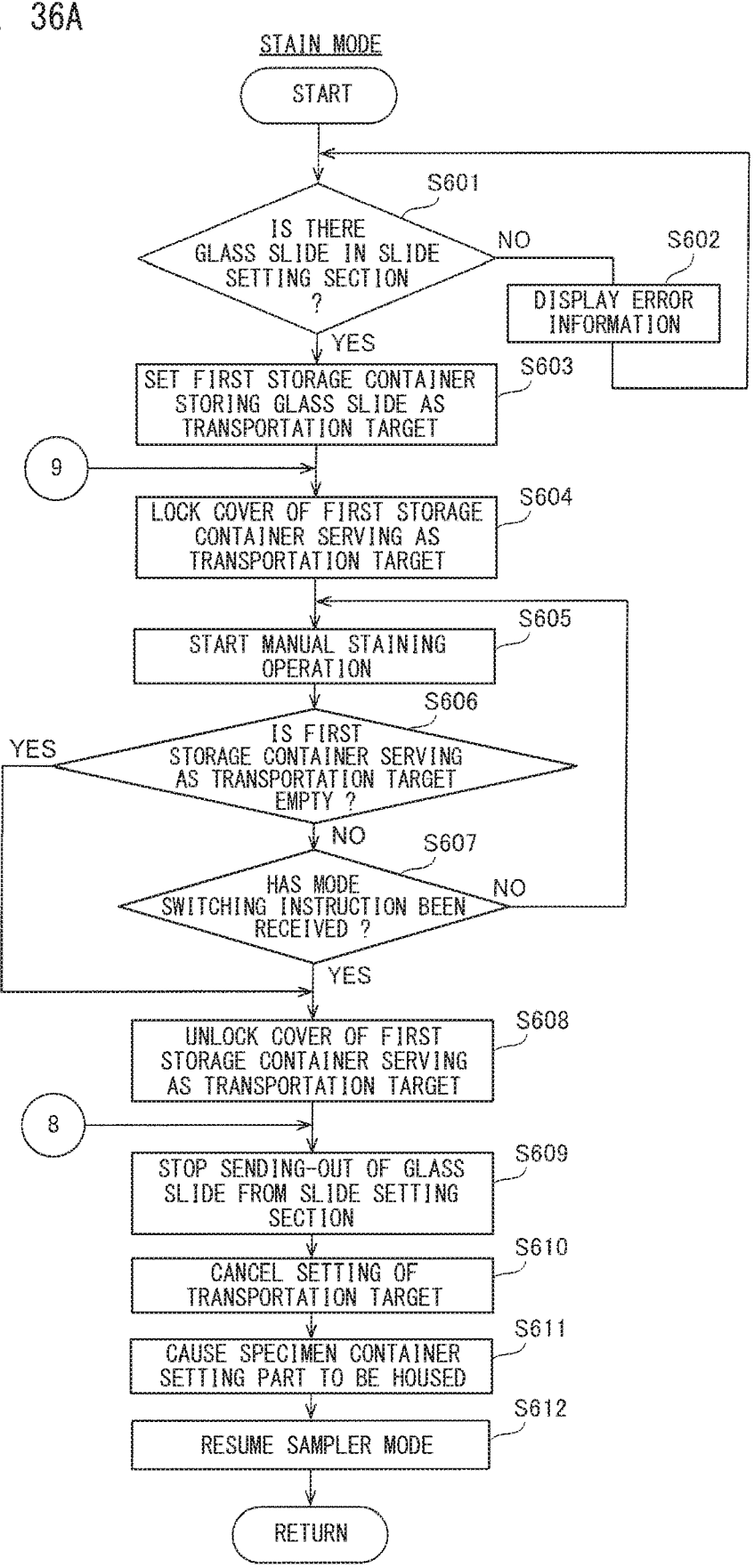
FIG. 36A is a flow chart showing the procedure of a stain mode.
Figure 36B:
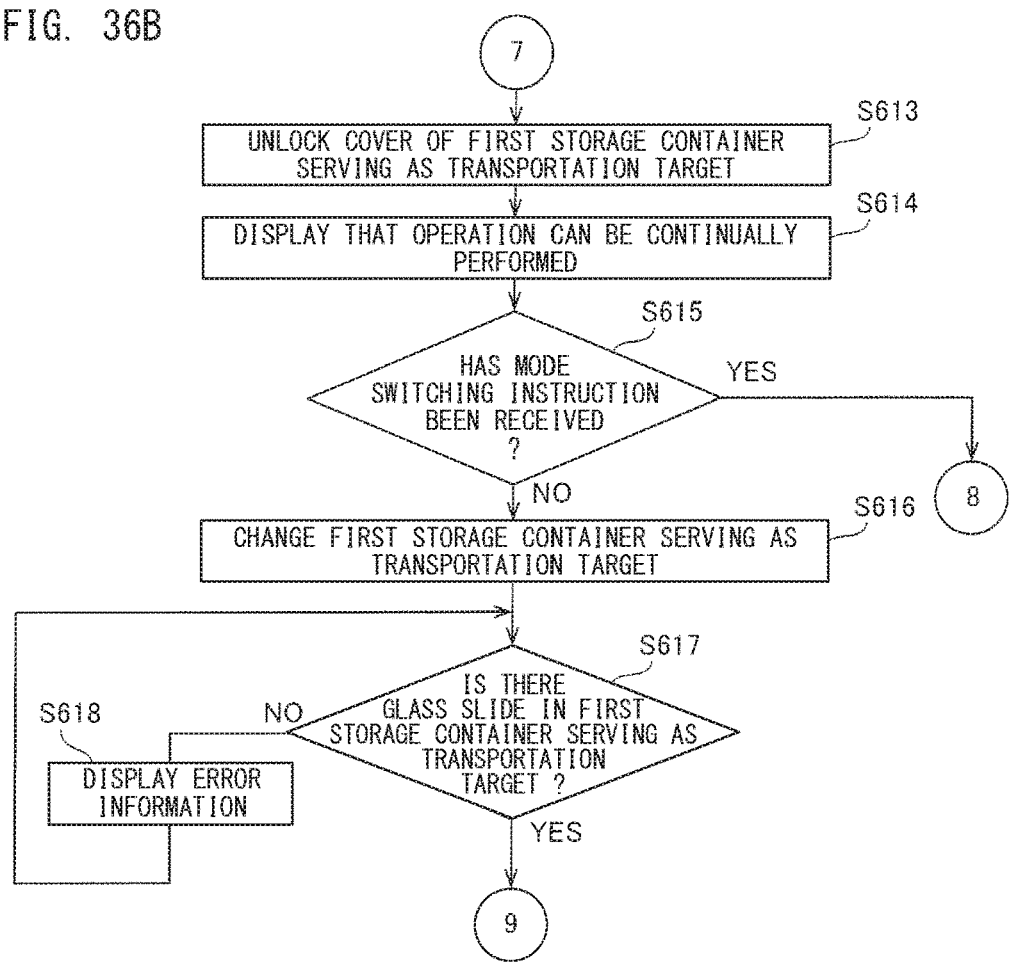
FIG. 36B is a flow chart showing the procedure of the stain mode.
Figure 38:
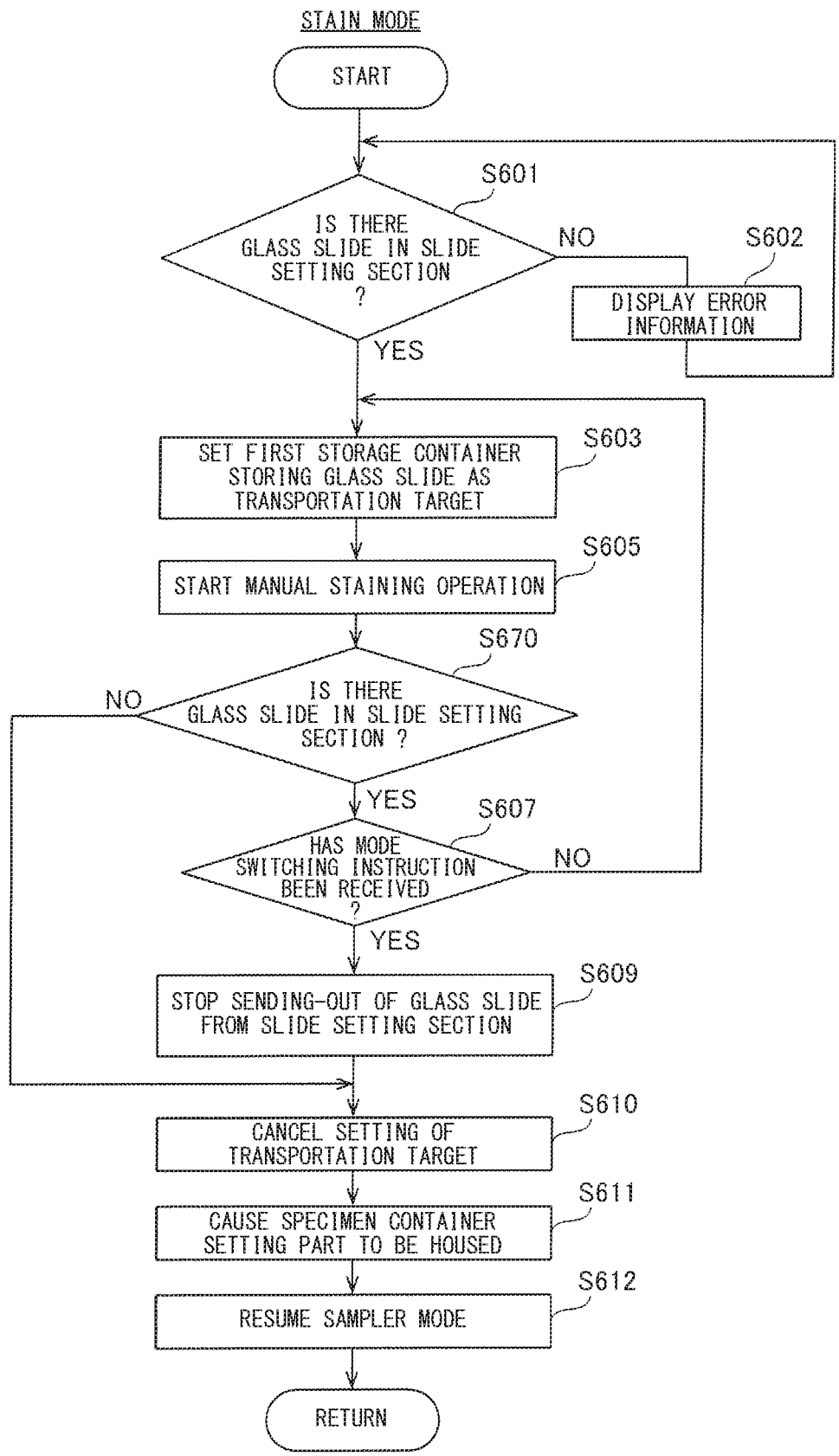
FIG. 38 is a flow chart showing another example of the stain mode.

Steps S601 to S605 shown in FIG. 38 are the same as the process of the stain mode shown in FIG. 36A, and thus, description thereof is omitted. In the flow shown in FIGS. 38, S604 and S608 in FIG. 36A are omitted for simplification, but S604 and S608 may be present.

After the manual staining operation according to the stain mode control (S651 to S655 in FIG. 37) in step S605 is started, the controller 230 determines whether or not there is a glass slide 10 in the slide setting section 170 (S670). Specifically, if a glass slide 10 stored in a first storage container 601 has been detected by the detector 640 for either the first setting section 610 or the second setting section 620, the controller 230 can determine that there is a glass slide 10 in the first storage container 601. When neither of the detectors 640 has detected a glass slide 10 stored in the corresponding first storage container 601, the controller 230 can determine that there is no glass slide 10 in the first storage container 601.

When there is a glass slide 10 in the slide setting section 170 (YES in S670), the controller 230 determines whether or not an instruction to switch to the sampler mode has been received (S607). When the instruction to switch to the sampler mode has not been received (NO in S607), the controller 230 sets a first storage container 601 as the transportation target (S603), and continues the manual staining operation.

In step S670, when there is no glass slide 10 in the slide setting section 170 (NO in S670), the controller 230 stop sending-out of the glass slide 10 from the slide setting section 170 (S609), cancels the setting of the first storage container 601 as the transportation target (S610), causes the specimen container setting part 811 to be housed in the housing of the smear sample preparing apparatus 300 (S611), and resumes the sampler mode control (S612). Then, the stain mode ends.

Also when the instruction to switch to the sampler mode has been received in step S607 (YES in S607), the controller 230 performs the process of steps S609 to S612. At this time, the controller 230 resumes the sampler mode control in step S612.

In the stain mode shown in FIG. 38, when the user wants the stain mode to be continued, if a smeared glass slide 10 is supplied to the slide setting section 170, the manual staining operation can be continued. That is, after the first storage container 601 set in one of the first setting section 610 and the second setting section 620 in the slide setting section 170 becomes empty, the manual staining operation is started on a smeared glass slide 10 in the first storage container 601 set in the other of the first setting section 610 and the second setting section 620. Thus, if the user takes out the first storage container 601 that has become empty, and sets a first storage container 601 storing a smeared glass slide 10, the manual staining operation can be continued.

In this manner, in the stain mode shown in FIG. 38, the controller 230 is configured so as to perform the stain mode control (S651 to S655), and to resume the sampler mode control (S612) after performing the stain mode control. In this example, the controller 230 is configured such that the controller 230 determines, without receiving an input, whether or not there is a glass slide 10 in the slide setting section 170 (S670), and the stain mode is automatically restored to the sampler mode on the basis of the presence/absence of a smeared glass slide 10. Accordingly, when the user wants the stain mode to be continued, it is sufficient to supply, during the stain mode, the slide setting section 170 with a smeared glass slide 10, and when the work in the stain mode is completed, the user is not required to perform specific operation and the mode can be automatically restored to the sampler mode on the basis of the presence/absence of a smeared glass slide 10.

In particular, when all the smeared glass slides 10 storable in the first storage container 601 are to be subjected to the manual staining process, the staining process takes a certain time period, and thus, the user might forget to perform operation for switching to the sampler mode or might want to perform another operation without paying attention to the state of the apparatus, in some cases. In such a case, the above-described configuration in which automatic restoration to the sampler mode can be performed on the basis of the presence/absence of a smeared glass slide 10 is especially effective, and convenience of the apparatus is improved.

It should be noted that the embodiments disclosed herein are merely illustrative in all aspects and should not be considered as restrictive. The scope of the present invention is defined not by the description of the above-described embodiments but by the scope of the claims, and includes meaning equivalent to the scope of the claims and all changes (modifications) within the scope.

What is claimed is:

1. A method implemented by a smear preparing apparatus, the method comprising:
receiving, by a controller of a smear preparing apparatus, a selection of a mode at least from a first mode and a second mode;
under the first mode, smearing a sample on a glass slide and transporting the glass slide via a staining station where the sample on the glass slide is stained to a first outlet where the glass slide with stained smeared sample is accessible by a user to remove; and
under the second mode, smearing a sample on a glass slide and transporting the glass slide to a second outlet, which is provided separately from the first outlet, where the glass slide with non-stained smeared sample is accessible by a user to remove without transporting the glass slide to the staining station.

2. The method of claim 1, wherein
the glass slide is transported, in sequence, to a smearing station where a sample is smeared on a glass slide, the staining station and the first outlet in the first mode; and
the glass slide is transported to the smearing station and to the second outlet in the second mode.

3. The method of claim 2, wherein
a time required for a glass slide traveling from the smearing station to the second outlet in the second mode is shorter than the time required for a glass slide traveling from the smearing station to the first outlet in the first mode.

4. The method of claim 1, wherein
under the first mode, the glass slides with stained smeared samples are loaded in a slide container capable of accommodating a plurality of glass slides and the slide container is set at the first outlet; and
under the second mode, the glass slides with non-stained smeared samples are loaded in a slide container capable of accommodating a plurality of glass slides and the slide container is set at the second outlet.

5. The method of claim 4, wherein
in the second mode, an access to the slide container at the second outlet is restricted while a glass slide to be loaded to the slide container is under process.

6. The method of claim 5, wherein
the access to the slide container at the second outlet is restricted by locking a mechanism to withdraw the slide container from the apparatus.

7. The method of claim 5, wherein
the access to the slide container at the second outlet is restricted by locking a mechanism to withdraw the slide container from the apparatus.

8. The method of claim 1, wherein
receiving the selection of the mode comprises displaying a screen, on a display of the smear preparing apparatus, on which a plurality of modes including the first and second modes are presented in selectable manner.

9. The method of claim 1, wherein
a selectable option of modes further comprises a third mode in which the second outlet is used as an installation port where a user installs a glass slide on which a sample is smeared in advance, and the method further comprising:
under the third mode, transporting a glass slide, on which a sample is smeared, from the second outlet as the installation port to the staining station and the first outlet.

10. The method of claim 1, wherein
a selectable option of modes further comprises a fourth mode, under the fourth mode, processing a glass slide at a processing station and transporting the glass slide to the second outlet without smearing a sample on the glass slide such that a glass slide processed at the processing station with no sample smeared thereon is set accessible for a user to remove at the second outlet.

11. The method of claim 10, wherein the glass slide is printed at the processing station.

12. The method of claim 1, wherein
under the first mode, the glass slides with stained smeared samples are loaded in a slide container capable of accommodating a plurality of glass slides and the slide container is set at the first outlet; and
under the second mode, the glass slides with non-stained smeared samples are loaded in a slide container capable of accommodating a plurality of glass slides and the slide container is set at the second outlet.

13. The method of claim 12, wherein
in the second mode, an access to the slide container at the second outlet is restricted while a glass slide to be loaded to the slide container is under process.

14. A method implemented by a smear preparing apparatus, the method comprising:
receiving, by a controller of a smear preparing apparatus, a selection of a mode at least from a first mode and a second mode;
under the first mode, receiving a glass slide at a first installation port, smearing a sample on a glass slide and transporting the glass slide to a staining station where the sample on the glass slide is stained; and
under the second mode, receiving a glass slide on which a sample is smeared in advance at a second installation port which is provided separately from the first installation port and transporting the glass slide to the staining station.

15. The method of claim 14, wherein
the glass slide is transported, in sequence, to a smearing station where a sample is smeared on a glass slide, the staining station and an outlet where the glass slide with the stained smeared sample is accessible for a user to remove in the first mode; and
the glass slide is transported to the staining station and to the outlet in the second mode.

16. The method of claim 14, wherein
a time required for a glass slide traveling from the second installation port to an outlet in the second mode is shorter than the time required for a glass slide traveling from the first installation port to the outlet in the first mode.

17. A method implemented by a smear preparing apparatus, the method comprising:
receiving, by a controller of a smear preparing apparatus, a selection of a mode at least from a first mode and a second mode;
under the first mode, smearing a sample on a glass slide, processing the glass slide and transporting the glass slide via a staining station where the sample on the glass slide is stained to a first outlet where the glass slide is accessible by a user to remove; and
under the second mode, processing a glass slide with no sample smeared and transporting the glass slide to a second outlet, which is provided separately from the first outlet, where the glass slide which is processed is accessible by a user to remove.

18. The method of claim 17, wherein
the glass slide is transported, in sequence, to a smearing station where a sample is smeared on a glass slide, a processing station where the glass slide is processed, the staining station and the first outlet in the first mode; and
the glass slide is transported to the processing smearing station and to the second outlet in the second mode.

19. The method of claim 18, wherein
a time required for a glass slide traveling from the processing station to the second outlet in the second mode is shorter than the time required for a glass slide traveling from the processing station to the first outlet in the first mode.

20. The method of claim 17, wherein the glass slide is printed at a processing station.

* * * * *